United States Patent
Bristol et al.

(10) Patent No.: US 11,542,510 B2
(45) Date of Patent: *Jan. 3, 2023

(54) E. COLI-BASED PRODUCTION OF BETA-LACTAMASE

(71) Applicant: Synthetic Biologics, Inc., Rockville, MD (US)

(72) Inventors: Andrew Bristol, Rockville, MD (US); Michael Kaleko, Rockville, MD (US); Steven Hubert, Rockville, MD (US)

(73) Assignee: Synthetic Biologics, Inc., Rockville, MD (US)

( * ) Notice: Subject to any disclaimer, the term of this patent is extended or adjusted under 35 U.S.C. 154(b) by 63 days.

This patent is subject to a terminal disclaimer.

(21) Appl. No.: 17/314,583

(22) Filed: May 7, 2021

(65) Prior Publication Data

US 2021/0332373 A1 Oct. 28, 2021

Related U.S. Application Data

(63) Continuation of application No. 15/506,342, filed as application No. PCT/US2015/047187 on Aug. 27, 2015, now Pat. No. 11,034,966.

(60) Provisional application No. 62/043,360, filed on Aug. 28, 2014.

(51) Int. Cl.
| | |
|---|---|
| *C12N 15/70* | (2006.01) |
| *C12P 21/02* | (2006.01) |
| *C12N 9/86* | (2006.01) |
| *C12N 15/67* | (2006.01) |
| *C12N 15/09* | (2006.01) |
| *C12N 15/75* | (2006.01) |

(52) U.S. Cl.
CPC ............ *C12N 15/70* (2013.01); *C12N 9/86* (2013.01); *C12N 15/67* (2013.01); *C12P 21/02* (2013.01); *C12Y 305/02006* (2013.01); *C12N 15/09* (2013.01); *C12N 15/75* (2013.01)

(58) Field of Classification Search
None
See application file for complete search history.

(56) References Cited

U.S. PATENT DOCUMENTS

| | | | |
|---|---|---|---|
| 2,890,986 A | 6/1959 | Kraut et al. | |
| 2,941,995 A | 6/1960 | Doyle et al. | |
| 2,982,696 A | 5/1961 | Puetzer et al. | |
| 3,070,511 A | 12/1962 | Weitnauer | |
| 3,150,059 A | 9/1964 | Kleinschmidt et al. | |
| 3,239,394 A | 3/1966 | Walton | |
| 3,488,729 A | 1/1970 | Chauvette et al. | |
| 3,499,909 A | 3/1970 | Weissenburger et al. | |
| 4,962,055 A | 10/1990 | Horikoshi et al. | |
| 5,190,874 A | 3/1993 | Horikoshi | |
| 5,607,671 A | 3/1997 | Heino | |
| 6,180,367 B1 | 1/2001 | Leung et al. | |
| 7,319,030 B2 | 1/2008 | Koski et al. | |
| 7,745,193 B2 | 6/2010 | Giannotta et al. | |
| 7,811,786 B1 | 10/2010 | Lee et al. | |
| 7,989,192 B2 | 8/2011 | Kaariainen et al. | |
| 8,894,994 B2 | 11/2014 | Koski et al. | |
| 2004/0248279 A1 | 12/2004 | Sawada et al. | |
| 2005/0158843 A1 | 7/2005 | Koski et al. | |
| 2005/0249716 A1 | 11/2005 | Bourgeois et al. | |
| 2009/0181004 A1 | 7/2009 | Kaariainen et al. | |
| 2009/0311234 A1 | 12/2009 | Koski et al. | |
| 2013/0216622 A1 | 8/2013 | Koski et al. | |

FOREIGN PATENT DOCUMENTS

| | | |
|---|---|---|
| EP | 0384559 A1 | 8/1990 |
| EP | 0420600 A2 | 4/1991 |
| EP | 0420600 A3 | 11/1992 |
| EP | 1564286 A1 | 8/2005 |
| FI | 59265 B | 3/1981 |
| FI | 880017 A | 7/1988 |
| GB | 1241844 A | 8/1971 |
| GB | 1463513 A | 2/1977 |
| GB | 2199582 A | 7/1988 |
| WO | 1988/07865 A | 10/1988 |
| WO | 1993/13795 A1 | 7/1993 |
| WO | 1997/03185 A1 | 1/1997 |
| WO | 2003/040352 A1 | 5/2003 |
| WO | 2004/016248 A2 | 2/2004 |
| WO | 2005/078075 A2 | 8/2005 |
| WO | 2006/122835 A1 | 11/2006 |
| WO | WO 2007/011077 A1 | 1/2007 |
| WO | 2007/147945 A1 | 12/2007 |
| WO | 2008/065247 A1 | 6/2008 |
| WO | 2011148041 A1 | 12/2011 |
| WO | 2016/057744 A1 | 4/2016 |

OTHER PUBLICATIONS

Altschul et al., "Gapped BLAST and PSI-BLAST: A New Generation of Protein Database Search Programs," Nucleic Acids Research, 1997, vol. 25, No. 17, pp. 3389-3402.
Ambler et al., "A Standard Numbering Scheme for the Class A Beta-Lactamases," Biochem. J., 1991, 276, pp. 269-270.
Ambler, "the structure of β-lactamases," Phil. Trans. R. Soc. Lond. B 289: 321-331 (1980).
Bonnet, "Growing Group of Extended-Spectrum β-Lactamases: the CTX-M Enzymes," Antimicrob. Agents Chemother. 48(1):1-14 (2004).
Bonomo et al., "β-Lactamase mutations far from the active site influence inhibitor binding," Biochim. Biophys. Acta 1247:121-125 (1995).
Brogard et al., "Biliary Elimination of Ticarcillin Plus Clavulanic Acid (Ciaventin®)," Experimental and Clinical Study, International Journal of Clinical Pharmacology, Therapy and Toxicology, 1989, vol. 27, No. 3, pp. 135-144.

(Continued)

*Primary Examiner* — Suzanne M Noakes
(74) *Attorney, Agent, or Firm* — Morgan, Lewis & Bockius LLP

(57) ABSTRACT

The invention relates to, in part, improved methods for the production of beta-lactamase using *Escherichia coli* (*E. coli*) cells. High yield production of beta-lactamase is achieved using methods of the invention.

14 Claims, 19 Drawing Sheets

Specification includes a Sequence Listing.

(56) References Cited

OTHER PUBLICATIONS

Braun et al., "Catalytic plasticity of fatty acid modification enzymes underlying chemical diversity of plant lipids," Science 1998, vol. 282: 1315-1317.

Bush et al., "A Functional Classification Scheme for β-Lactamases and Its Correlation with Molecular Structure," Antimicrobial Agents and Chemotherapy, Jun. 1995, vol. 39, No. 6, pp. 1211-1233.

Bush, "Metallo-β-Lactamases: A Class Apart," Clinical Infectious Diseases, 1998; 27(Suppl 1):S48-53.

Canica et al., "Phenotypic Study of Resistance of β-Lactamase-Inhibito-Resistant TEM Enzymes Which Differ by Naturally Occurring Variations and by Site-Directed Substitution at Asp276," Antimicrob. Agents Chemother. 42(6):1323-1328 (1998).

Carfi et al., "1.85 Å Resolution Structure of the Zinc II β-Lactamase from Bacillus cereus," Acta Cryst. (1998) D54: 313-323.

Carfi et al., "The 3-D structure of a zinc metallo-β-lactamase from Bacillus cereus reveals a new type of protein fold," The EMBO Journal, 1995, vol. 14 No. 20: 4914-4921.

Carfi et al., "X-ray Structure of the Zn11 β-Lactamase from Bacteroides fragilis in an Orthorhombic Crystal Form," Acta. Cryst. (1998) D54: 47-57.

Chambliss, "The forgotten dosage form: enteric coated tablets," (1983) Pharm Technol 7, 124-140.

Chen et al.,"β-Lactamase Genes of the Penicillin-Susceptible Bacillus anthracis Sterne Strain," J. Bacteriol. 185(3):823-830 (2003).

Chica et al., "Semi-rational approaches to engineering enzyme activity: combining the benefits of directed evolution and rational design," Curr. Opin. Biotechnol., 2005, vol. 16: 378-384.

Cole, "Hydrolysis of Penicillins and Related Compounds by the Cell-Bound Penicillin Acylase of *Escherichia coli*," (1969) Biochem. J. 115, 733-739.

Colombo et al., "The ybxI Gene of Bacillus Subtilis 168 Encodes a Class D β-Lactamase of Low Activity," Antimicrobial Agents and Chemotherapy, Feb. 2004, vol. 48, No. 2, pp. 484-490.

Concha et al., "Crystal Structure of the IMP-1 Metallo β-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.

Crawford, et al., "Over-expression, purification, and characterization of metallo-β-lactamase ImiS from Aeromonas veronii bv. sobria," Protein Expression and Purification 36 (2004) 272-279.

Database UniProtKB/Swiss-Prot: P00808 (BLAC_BACLI), 1986.

Davies and Abraham, "Separation, Purification and Properties of β-Lactamase I and β-Lactamase II from Bacillus cereus 569/H/9," (1974) Biochem. J. 143:115-127.

Delmas et al., "Structural Insights into Substrate Recognition and Product Expulsion in CTX-M Enzymes," J. Mol. Biol. 400:108-120 (2010).

Devos et al., "Practical limits of function prediction," Proteins: Structure, Function, and Genetics. 2000, vol. 41: 98-107.

Donskey, "Antibiotic Regimens and Intestinal Colonization with Antibiotic-Resistant Gram-Negative Bacilli," Clinical Infectious Diseases, 2006, 43 Suppl 2, pp. S62-S69.

Drawz et al., "The Role of a Second-Shell Residue in Modifying Substrate and Inhibitor Interactions in the SHV β-Lactamase: A Study of Ambler Position Asn276," Biochem. 48(21):4557-4566 (2009).

Drawz, et al., "Three Decades of β-Lactamase Inhibitors," Clin Microbiol Rev., 2010, vol. 23, No. 1, pp. 160-201.

Fey et al., Cetriaxone-Resistant *Salmonella* Infection Acquired by a Child from Cattle, New England J. Med., 2000, 342,1242-1249.

Fonze et al., "Crystal Structures of the Bacillus Licheniformis BS3 Class A β-Lactamase and of the Acyl-Enzyme Adduct Formed with Cefoxitin," Biochemistry, 2002, 41, 1877-1885.

Galleni et al., "Standard Numbering Scheme for Class B β-Lactamases," Antimicrobial Agents and Chemotherapy, Mar. 2001, vol. 45, No. 3, pp. 660-663.

Garau et al., "Update of the Standard Numbering Scheme for Class B β-Lactamases," Guest Commentary, Antimicrobial Agents and Chemotherapy, Jul. 2004, pp. 2347-2349, vol. 48, No. 7.

Garau et al., "A Metallo-β-lactamase Enzyme in Action: Crystal Structures of the Monozinc Carbapenemase CphA and its Complex with Biapenem," J. Mol. Biol. (2005) 345, 785-795.

Gazouli et al., "Effect of substitution of Asn for Arg-276 in the cefotaxime-hydrolyzing class A β-lactamase CTX-M-4," FEMS Microbiol. Lett. 168:289-293 (1998).

Gebhard et al., "Mapping the Distribution of Conformational Information Throughout a Protein Sequence," J. Mol. Biol., 2006, 358, pp. 280-288.

Gerrits et al., Helicobacter Ppylori and Antimicrobial Resistance: Molecular Mechanism and Clinical Implications. The Lancet Infectious Disease, 2006, vol. 6, pp. 699-709.

Giakkoupi et al., "Aspartic acid for asparagine substitution at position 276 reduces susceptibility to mechanism-based inhibitors in SHV-1 and SHV-5 β-lactamases," J. Antimicrobial. Chemother. 43:23-29 (1999).

Girlich et al., "Value of the Modified Hodge Test for Detection o Emerging Carbapenemases in Enterobacteriaceae", Journal of Clinical Microbiology, 2012, vol. 50, No. 2, pp. 477-479.

Harmoinen et al., "Enzymic Degradation of a β-Lactam Antibiotic, Ampicillin, in the Gut: A Novel Treatment Modality," Journal of Antimicrobial Chemotherapy, 2003,51, pp. 361-365.

Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.

Hata et al., "Substrate Deacylation Mechanisms of Serine-β-lactamases," Biol. Pharm. Bull. 29:2151-2159 (2006).

Herzberg, "Refined Crystal Structure of β-Lactamase from *Staphylococcus aureus* PC1 at 2.0 Å Resolution," J. Mol. Biol. 217:701-719 (1991).

Higgins et al., "In Vitro Activities of the β-Lactamase Inhibitors Clavulanic Acid, Sulbactam, and Tazobactam Alone or in Combination with β-Lactams against Epidemiologically Characterized Multidrug-Resistant Acinetobacter baumannii Strains," Antimicrobial Agents and Chemotherapy, May 2004, vol. 48, No. 5, pp. 1586-1592.

Hirschi A et al. (Abstract) "Campylobacter pylori, Gastritis and Ulcus pepticum," Wien. Klin. Wsch. 14:493-497 (1987).

Horton et al., "Engineering hybrid genes without the use of restriction enzymes: gene splicing by overlap extension," 1989, Gene 77:61-68 (1989).

Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.

Hyman, "Anaphylactic Shock After Therapy With Penicillinase," (1959) JAMA 169, 593-594.

Illing et al., "Use of integrational plasmid excision to identify cellular localization of gene expression during sporulation n Bacillus subtilis," J. Bacteriol. 172(12):6937-6941 (1990).

Iserhard et al., "Epidemiology and Treatment of Gastric Campylobacter pylori Infection: more Questions than Answers," (1990) Hepato-Gastroenterol 37, 38-44.

Izui et al., "Large Exopenicillinase, Initial Extracellular Form Detected in Cultures of Bacillus licheniformis," Biochemistry, 1980, 19, pp. 1882-1886.

Materon, et al., "Biochemical Characterization of Lactamases Bla1 and Bla2 from Bacillus antracis," Antimicrobial Agents and Chemotheraply, vol. 47, No. 6, pp. 2040-2042, Jun. 1, 2003.

Perilli, et al., "Overexpression system and biochemical profile of CTX-M-3 extended-spectrum β-lactamase expressed in *Escherichia coli*," FEMS Microbiology Letters, vol. 241, pp. 229-232, 2004.

Shaw, et al., "Hyperexpression in *Eccherichia coli*, Purification, and Characterization of the Metallo-β-lactamase of *Bacillus cererus* 5/B/6," Protein Expression and Purification, vol. 2, pp. 151-157, 1991.

International Search Report and Written Opinion for PCT Application No. PCT/US15/47187, dated Dec. 7, 2015, 9 pages.

(56) References Cited

OTHER PUBLICATIONS

U.S. Appl. No. 12/304,874, U.S. Pat. No. 7,989,192, filed Dec. 15, 2008.
U.S. Appl. No. 13/699,434, U.S. Pat. No. 9,034,602, filed Nov. 21, 2012.
U.S. Appl. No. 14/047,882, U.S. Pat. No. 8,894,994, filed Oct. 7, 2013.
U.S. Appl. No. 14/517,539, U.S. Pat. No. 9,301,995, filed Oct. 17, 2014.
U.S. Appl. No. 14/676,559, U.S. Pat. No. 9,301,996, filed Apr. 1, 2015.
U.S. Appl. No. 15/054,292, U.S. Pat. No. 9,587,234, filed Feb. 26, 2016.
U.S. Appl. No. 15/138,767, U.S. Pat. No. 9,765,320, filed Apr. 26, 2016.
Therapeutic Drugs (1991), Dollery C, ed. Edinburgh: Churchill Livingstone, "Ceftriaxone (sodium)," c 127-c133.
Tranier et al., "The High Resolution Crystal Structure for Class A β-Lactamase PER-1 Reveals the Bases for Its Increase in Breadth of Activity," J. Biol. Chem. 275:28075-28082 (2000).
Walsh et al., "Metallo-β-Lactamases: the Quiet before the Storm?" Clinical Microbiology Reviews (Apr. 2005) vol. 18 No 2: 306-325.
Walther-Rasmussen et al., "Terminal truncations in Amp C β-lactamase from a clinical isolate of Pseudomonas aeruginosa," Eur. J. Biochem. (1999) 263: 478-485.
Westphal et al., "Assessment of Biliary Excretion of Piperacilin-Tazobactam in Humans," Antimicrobial Agents and Chemotherapy, Aug. 1997, vol. 41, No. 8, pp. 1636-1640.
Whisstock et al., "Prediction of protein function from protein sequence," Q. Rev. Biophysics., 2003, vol. 36 (3): 307-340.
Wildfeuer et al., "Pharmacokinetics of Sulbactam and Ampicillin Intravenously Applied in Combination to Healthy Volunteers and Patients", Arzneimittei-Forschung, 1988, vol. 38, No. 11, pp. 1640-1643.
Wishart et al., "A single mutation converts a novel phosphotyrosine binding domain into a dual-specificity phosphatase," J. Biol. Chem., 1995, vol. 270(45): 26782-26785.
Witkowski et al., "Conversion of β-ketoacyl synthase to a Malonyl Decarboxylase by replacement of the active cysteine with glutamine," Biochemistry, 1999, vol. 38: 11643-11650.
Jones et al., Cefoperazone: A Review of its Antimicrobial Spectrum, β-Lactamase Stability, Enzyme Inhibition, and Other in Vitro Characteristics, 1983, Rev. Infectious Disease 5 S108-S126.
Kaleko, et al., "SYN-004, a Class A β-Lactamase Therapy for the Prevention of Antibiotic-Induced Disruption of Intestinal Microflora", Open Forum Infect Dis, Oct. 9, 2014, I (suppl 1): SI15-SI16.
Kato et al., "Nucleotide Sequence of the β-Lactamase Gene of Alkalophilic Bacillus sp. Strain 170," J. Gen. Microbiol. 131:3317-3324 (1985).
Katz, "Probiotics for the Prevention of Antibiotic-associated Diarrhea and Clostridium difficile Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, "β-Lactamase of Bacillus licheniformis 749/C: Refinement at 2 Å Resolution and Analysis of Hydration," J. Mol. Biol., 1991, 220, pp. 435-455.
Knox, "Extended-spectrum and inhibitor-resistant TEM-Type β-lactamases: Mutations, Specificity, and Three-Dimensional Structure," Antimicrob Agents Chemother, 1995, 39, 2593-2601.
Korhonen et al., "Milk Immunoglobulins and Complement Factors," British Journal of Nutrition, 2000, 84 Suppl 1, pp. S75-S80.

Kropp et al., "Metabolism of Thienamycin and Related Carbapenem Antibiotics by the Renal Dipeptidase, Dehydropeptidase-I," (1982) Antimicrob Agents Chemother 22, 62-70.
Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 β-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, "β-Lactamase I from Bacillus cereus," Biochem. J. 248(3):657-662 (1987).
Madonna et al., "Nucleotide sequence of the β-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman and Gilman's, The Pharmacological Basis of Therapeutics, 8th Edition New York: Pergamon Press, 1065-1097.
Marciano et al., "Analysis of the plasticity of location of the Arg244 positive charge within the active site of the TEM-1 β-lactamase," Prot. Sci. 18:2080-2089 (2009).
Marmur, "A Procedure for the Isolation of Deoxyribonucleic Acid from Micro-organisms," J. Mol. Biol. (1961) 3: 208-218.
Matagne et al., "Catalytic properties of class A β-lactamases: efficiency and diversity," Biochem. J. 330:581-598 (1998).
Matagne et al., "Ragged N-termini and other Variants of Class A β-Lactamases Analysed by Chromatofocusing," Biochem. J., 1991, 273, pp. 503-510.
Mentula et al., "Inhibition of ampicillin-induced emergence of resistance in intestinal coliforms by targeted recombinant β-lactamase," International Journal of Antimicrobial Agents, (2004)24:555-561.
Mezes, et al., "Construction of penP delta 1, Bacillus licheniformis 749/C β-Lactamase Lacking Site for Lipoprotein Modification," The Journal of Biological Chemistry, 1993, vol. 258, No. 18, pp. 11211-11218.
O'Callaghan et al., "Novel Method for Detection of β-Lactamases by Using a Chromogenic Cephalosporin Substrate," Antimicrobial Agents and Chemotherapy, Apr. 1972, vol. 1, No. 4, pp. 283-288.
Patel et al., "Status Report on Carbapenemases: Challenges and Prospects", Expert review of Anti-Infective Therapy, 2011, vol. 9, No. 5, pp. 555-570.
Pedraza-Reyes et al., "Temporal Regulation and Forespore-Specific Expression of the Spore Photoproduct Lyase Gene by Sigma-G RNA Polymerase during Bacillus subtilis Sporulation," J. Bacteriol. 176(13): 3983-3991. 1994.
Perez-Llarena et al., "Structure-function studies of arginine at position 276 in CTX-M β-lactamases," J. Antimicrob. Chemother. 61(4):792-797 (2008).
Pitout, (Abstract) "IPSAT P1A, a class A beta-lactamase therapy for the prevention of penicillin-induced disruption to the intestinal microflora," Current Opinion in investigational drugs (London, England: 2000) 10.8 (2009): 838-844.
Pluckthun and Knowles, "The consequence of of stepwise deletions from the signal-processing site of β-lactamase," J. Biol.Chem., 1987, vol. 262 (9): 3951-3957.
Rauws and Tytgat, "Cure of duodenal ulcer associated with eradication of Helicobacter pylori," (1990) Lancet 335, 1233-1235.
Rauws et al., "Campylobacter pyloridis-Associated Chronic Active Antral Gastritis," (1988) Gastroenterol 94, 33-40.
Rice et al., "β-Lactam Antibiotics and Gastrointestinal Colonization with Vancomycin-Resistant Enterococci," J. Infect. Dis., 2004, 189, pp. 1113-1118.
Sambrook and Russell. Molecular Cloning: A Laboratory Manual. "In vitro Amplification of DNA by the Polymerase Chain Reaction," vol. 2, Ch. 8, pp. 8.1-8.126. 2001.

(56) References Cited

OTHER PUBLICATIONS

Sande et al., "Chapter 44. Antimicrobial Agents," (1990) In: Goodman and Gilman's, The Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged β-Lactamase," Biochemistry, 2004, 43, pp. 1715-1723.
Saunders et al., "Use of Chromosomal Integration in the Establishment and Expression of blaZ, a *Staphylococcus aureus* β-lactamase Gene, in Bacillus subtilis," J. Bacteriol. 157(3): 718-726. 1984.
Saves et al., "The Asparagine to Aspartic Acid Substitution at Position 276 of TEM-35 and TEM-36 Is Involved in the β-Lactamase Resistance to Clavulanic Acid," J. Biol. Chem. 270:18240-18245 (1995).
Sawa et al., (Abstract) "The Effect of Cefixime on Bacterial Flora in the Intestinal Tracts of Healthy Male Volunteers," (1985) Chemotherapy (Tokyo) 33, Suppl. 6, 169-180.
Sen et al., "Developments in directed evolution for improving enzyme functions," Appl. Biochem. Biotechnol., Aug. 18, 2007, vol. 143: 212-223.
Shimooka et al, (Abstract) "Absorption, Distribution, and Excretion of Sulbactam and Ampilcillin after Intravenous Administration in Rats and Dogs," Chemotherapy (Tokyo), 1988, 36 Suppl 8, pp. 66-80.
Simm et al., "Characterization of Monomeric L1 Metallo-β-lactamase and the Role of the N-terminal Extension in Negative Cooperativity and Antibiotic Hydrolysis," The Journal of Biological Chemistry (Jul. 2002) vol. 277 No. 27: 24744-24752.
Sjolund et al., "Long-Term Persistence of Resistant Enterococcus Species after Antibiotics To Eradicate Helicobacter pylori," Ann. Intern. Med. 139:483-487 (2003).
Stiefel et al., "Oral Administration of β-Lactamase Preserves Colonization Resistance of Piperacillin-Treated Mice," J. Infect. Dis., 2003, 188, pp. 1605-1609.
Stiefel et al., "Orally Administered Recombinant Metallo-β-Lactamase Preserves Colonization Resistance of Piperacillin-Tazobactam-Treated Mice," Antimicrobial Agents and Chemotherapy, Dec. 2005, vol. 49, No. 12, pp. 5190-5191.
Stiefel, et al. "Gastrointestinal Colonization with a Cephalosporinase-Producing Bacteroides Species Preserves Colonization Resistance against Vancomycin-Resistant Enterococcus and Clostridium difficile in Cephalosporin-Treated Mice." Antimicrobial Agents and Chemotherapy, 2014, vol. 58, No. 8, pp. 4535-4542.
Sullivan et al., "Effect of Antimicrobial Agents on the Ecological Balance of Human Microflora," Lancet Infect. Dis., 2001, vol. 1, pp. 101-114.
Tarkkanen et al., "P1A Recombinant β-Lactamase Prevents Emergence of Antimicrobial Resistance in Gut Microflora of Healthy Subjects during Intravenous Administration of Ampicillin," Antimicrob. Agents Chemother. 53:2455-2462 (2009).
U.S. Appl. No. 15/417,501, U.S. Pat. No. 10,041,056, filed Jan. 27, 2017.
U.S. Appl. No. 15/661,416, U.S. Pat. No. 10,253,306, filed Jun. 27, 2017.
U.S. Appl. No. 14/878,155, U.S. Pat. No. 10,105,322, filed Oct. 8, 2015.
U.S. Appl. No. 14/757,522, U.S. Pat. No. 9,744,221, filed Dec. 23, 2015.
U.S. Appl. No. 15/062,559, U.S. Pat. No. 10,709,773, filed Mar. 7, 2016.

E. COLI-BASED PRODUCTION OF BETA-LACTAMASE

CROSS-REFERENCE TO RELATED APPLICATIONS

This application is a continuation of U.S. patent application Ser. No. 15/506,342, filed Feb. 24, 2017, which is a national stage of International Patent Application No. PCT/US2015/47187, filed Aug. 27, 2015, which claims the benefit of U.S. Provisional Patent Application No. 62/043,360, filed Aug. 28, 2014, the entire contents of which are herein incorporated by reference.

FIELD OF THE INVENTION

The invention relates to, in part, improved methods for the production of beta-lactamases using *Escherichia coli* (*E. coli*) cells. High yield production of beta-lactamase, including those suitable for pharmaceutical formulations, is achieved using methods of the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SYN-005PC-SequenceListing.txt; date recorded: Aug. 20, 2015; file size: 19 KB).

BACKGROUND

Beta-lactam antibiotics are characterized by a beta-lactam ring in their molecular structure. The integrity of the beta-lactam ring is essential for the biological activity, which results in the inactivation of a set of transpeptidases that catalyze the final cross-linking reactions of peptidoglycan synthesis. Members of the beta-lactam antibiotics family include penicillins, cephalosporins, clavams (or oxapenams), cephamycins and carbapenems.

Beta-lactamases are bacterial defensive enzymes that hydrolyze beta-lactam antibiotics. Gram-negative bacteria produce beta-lactamases to achieve resistance to beta-lactam antibiotics. Particularly, beta-lactamases are able to efficiently catalyze the irreversible hydrolysis of the amide bond of the beta-lactam ring resulting in biologically inactive product(s).

Humans may be considered to be a "superorganism" which is a conglomerate of mammalian and microbial cells, with the latter estimated to outnumber the former by ten to one. This microbial component, and its microbial genetic repertoire, the microbiome, is roughly 100-times greater than that of the human host. Strikingly, despite this enormous diversity of foreign organisms, the human immune system generally maintains a state of synergy. This is particularly true of the distal GI tract, which houses up to 1000 distinct bacterial species and an estimated excess of $1 \times 10^{14}$ microorganisms, and appears to be central in defining human host health status. Loss of the careful balance in the microbiome, especially in the GI tract, can lead to various diseases.

Antibiotic medical treatments, which are needed to treat certain aspects of disease, can induce disruption in the microbiome, including in the GI tract, and lead to further disease. For instance, certain parentally administered beta-lactams like ampicillin, ceftriaxone, cefoperazone, and piperacillin are, in part, eliminated via biliary excretion into the proximal part of the small intestine (duodenum). Residual unabsorbed beta-lactams in the intestinal tract may cause an undesirable effect on the ecological balance of normal intestinal microbiota resulting in, for example, *Clostridium difficile* infection (CDI), antibiotic-associated diarrhea, overgrowth of pathogenic bacteria such as vancomycin resistant enterococci (VRE), extended-spectrum beta-lactamase producing Gram-negative bacilli (ESBL), and fungi, and selection of antibiotic-resistance strains among both normal intestinal microbiota and potential pathogen bacteria.

One approach for avoiding or rebalancing the ecological balance of normal intestinal microbiota is the therapeutic use of beta-lactamases, for example, by inactivating excreted or unabsorbed antibiotics in the GI tract, thereby maintaining a normal intestinal microbiota and preventing its overgrowth with potentially pathogenic microorganisms.

Accordingly, there is remains a need for efficient methods of producing beta-lactamases at a commercial scale for use in therapeutic intervention.

SUMMARY OF THE INVENTION

The present invention provides an improved method for the production of a beta-lactamase polypeptide in *Escherichia coli* (*E. coli*) cells. The method includes providing a host *E. coli* cell transformed with a vector comprising a sequence encoding the beta-lactamase polypeptide. The *E. coli* cell is cultured to induce expression of the beta-lactamase in the cytoplasm. Soluble fractions are subsequently prepared from the *E. coli* cell to recover the beta-lactase polypeptide.

The methods of the invention allows for production of beta-lactamases at a high yield. In an embodiment, the method yields at least 10 grams of the beta-lactamase polypeptide per liter of culture. In another embodiment, the method yields at least 15 grams of the beta-lactamase polypeptide per liter of culture.

Various strains of *E. coli* cells may be employed for the instant invention. For example, the *E. coli* cell may be selected from BL21 (DE3) or W3110. The beta-lactamase polypeptide is predominantly expressed in the cytoplasm of the *E. coli* cell. In certain embodiments, expression of the polypeptide is induced by adding isopropylthiogalactoside (IPTG) to the culture.

The disclosed method may be utilized to produce beta-lactamases and derivatives thereof. In one embodiment, the beta-lactamase polypeptide comprises a sequence having at least 60% identity with P1A. In another embodiment, the beta-lactamase polypeptide comprises a sequence having at least 60% identity with P2A. In yet another embodiment, the beta-lactamase polypeptide comprises a sequence having at least 60% identity with P3A. In a further embodiment, the beta-lactamase polypeptide comprises a sequence having at least 60% identity with P4A. In various embodiments, the present methods are used to produce beta-lactamases useful for microbiome-protecting therapy.

DETAILED DESCRIPTION

Figure 1:
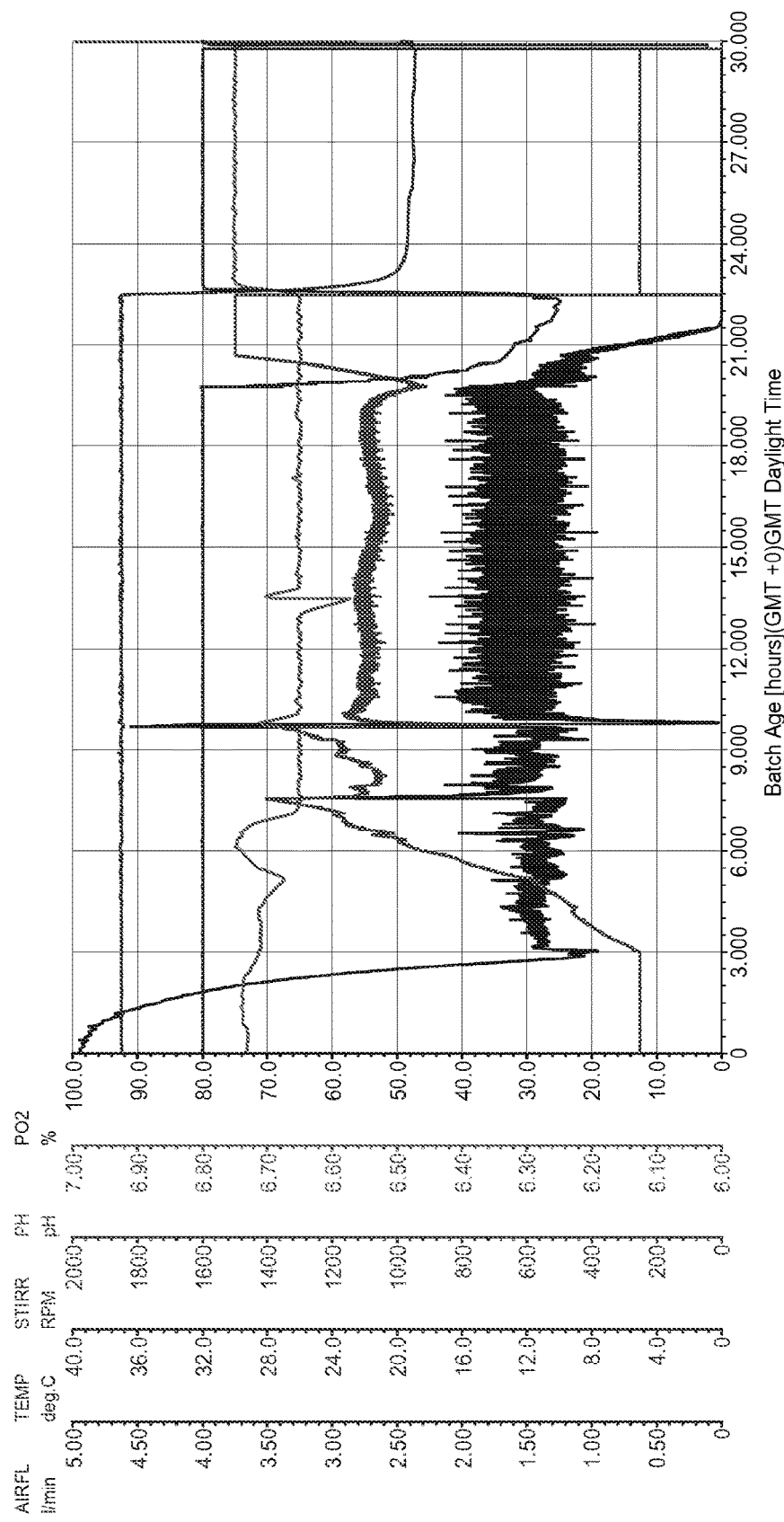
FIG. 1 shows a multi-fermenter computer system (MFCS) CLD977 fermentation plot of batch age (hours) vs. airflow (AIRFL (l/min), second line from top), temperature (TEMP (° C.), top line), stirring rate (STIRR (RPM), second line from the bottom), pH (third line), and percent oxygen ($PO_2$, bottom line).

The present invention is based, in part, on the surprising discovery that a beta-lactamase polypeptide can be overproduced in high yields in E. coli cells. Specifically, high yield production is achieved by expressing the polypeptide in the cytoplasm of E. coli cells and subsequently recovering the polypeptide from soluble fractions prepared from the cells.

Prior to the present invention, it was well established that beta-lactamases, such as the beta-lactamase from Bacillus licheniformis, are mostly found in the cell envelope and periplasmic fractions of E. coli cells. See Mezes, et al., J Biol Chem (1983), 258(18): 11211-11218. Particularly, beta-lactamase from Bacillus licheniformis is found to be completely absent in the cytoplasm. Id.

Further still, production of beta-lactamases from E. coli cells has generally been inefficient leading to an overall yield on the scale of milligrams of the enzyme per liter of culture. See, for example, Shaw et al., Protein Expr Purif. (1991), 2(2-3): 151-157. Given that the beta-lactamses are from Bacillus licheniformis, it is expected that production of these enzymes in Bacillus strains may provide a higher yield. However, studies shown herein demonstrate that even when produced in Bacillus subtilis cells, the yield of beta-lactamases is low. Accordingly, it is surprising that the present invention achieves an overall yield of beta-lactamases on the scale of grams per liter of culture.

Accordingly, the present invention provides an improved method for the production of a beta-lactamase polypeptide in Escherichia coli (E. coli) cells. The method includes providing a host E. coli cell transformed with a vector comprising a sequence encoding the beta-lactamase polypeptide. The E. coli cell is cultured to induce expression of the beta-lactamase in the cytoplasm. Soluble fractions are subsequently prepared from the E. coli cell for recovery of the beta-lactase polypeptide.

The present invention allows for high-yield production of a beta-lactamase polypeptide in E. coli cells. In various embodiments, methods of the present invention provides a yield of at least about 1 gram, about 2 grams, about 3 grams, about 4 grams, about 5 grams, about 6 grams, about 7 grams, about 8 grams, about 9 grams, about 10 grams, about 11 grams, about 12 grams, about 13 grams, about 14 grams, about 15 grams, about 16 grams, about 17 grams, about 18 grams, about 19 grams, about 20 grams, about 22 grams, about 24 grams, about 26 grams, about 28 grams, about 30 grams, about 35 grams, about 40 grams, about 45 grams, or about 50 grams of the beta-lactamase polypeptide per liter of culture. In one embodiment, at least about 10 grams of the beta-lactase polypeptide per liter of culture is recovered. In another embodiment, about at least 15 grams of the beta-lactase polypeptide per liter of culture is recovered. In a further embodiment, at least about 18 grams of the beta-lactase polypeptide per liter of culture is recovered.

In various embodiments, the present methods provide one or more of greater yield and improved purity as compared to a *Bacillus*-based expression system such as, for example, those described in U.S. Pat. No. 7,319,030, the entire contents of which are hereby incorporated by reference. In various embodiments, the present methods provide one or more of greater yield and improved purity as compared to a method for producing a desired polypeptide product using a non-sporulating *Bacillus subtilis* strain, in which a deletion region of at least 150 nucleotides has been deleted from its sigG gene, the method involving transforming the strain with a polynucleotide construct encoding a recombinant polypeptide, expressing the polynucleotide construct, and recovering the recombinant polypeptide. In some embodiments the method comprises deleting at least part of either of the two functional regions of the sigG gene (i.e. the regions which code for amino acids 67 to 80 or 229 to 248).

In various embodiments, the present methods provide about a 5-fold, or about a 7.5-fold, or about a 10-fold, or about a 15-fold improvement in yield in *E. coli* versus a *Bacillus*-based expression system such as, for example, those described in U.S. Pat. No. 7,319,030.

Various *E. coli* cell can be used with the present invention. Illustrative *E. coli* cells include, but are not limited to, BL21 (DES), W3110, DH5α, HMS174, and derivatives thereof. In one embodiment, the *E. coli* cell is the BL21 (DES) strain. In another embodiment, the *E. coli* cell is W3110 strain. The genotype of W3110 is *E. coli* K12 F-, λ-, IN (mD-mE)1, rph-1. It is a Gram negative, rod-shaped, facultative anaerobe, and its genealogy is well described (Bachmann, B J 1972. Pedigrees of some mutant strains of *Escherichia coli* K-12. Bacteriol. Rev. 36(4):525-57). There have been no modifications of this strain prior to transformation with the B3214 plasmid.

The present invention is used to produce beta-lactamase polypeptides at a high yield. In various aspects, the beta-lactamases polypeptide has the sequence of SEQ ID NO: 1 (*Bacillus licheniformis* PenP, i.e., P1A) or is derived by one or more mutations of SEQ ID NO: 1. Provided herein is the 263 amino acid sequence of the P1A enzyme (after removal of a 31 amino acid signal sequence and the QASKT (Gln-Ala-Ser-Lys-Thr) (SEQ ID NO: 11) pentapeptide at the N terminus, see SEQ ID NO: 3). As described herein, mutations may be made to this sequence to generate beta-lactamase derivatives that may be produced by methods of the invention.

SEQ ID NO: 1
EMKDDFAKLEEQFDAKLGIFALDTGTNRTVAYRPDERFAFASTIKALTVGV

LLQQKSIEDLNQRITYTRDDLVNYNPITEKHVDTGMTLKELADASLRYSDN

AAQNLILKQIGGPESLKKELRKIGDEVTNPERFEPELNEVNPGETQDTSTA

RALVTSLRAFALEDKLPSEKRELLIDWMKRNTTGDALIRAGVPDGWEVADK

TGAASYGTRNDIAIIWPPKGDPVVLAVLSSRDKKDAKYDDKLIAEATKVVM

KALNMNGK.

In some embodiments, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1.

In some embodiments, SEQ ID NO: 1 may have a Met and/or Thr preceding the first residue of the sequence. In various embodiments, the Met may be cleaved. As described herein, mutations may be made to the sequence comprising the Met and/or Thr preceding the first residue to generate beta-lactamase derivatives.

Also provided herein is the 299 amino acid sequence of the P1A enzyme before removal of a 31 amino acid signal sequence and the QASKT (Gln-Ala-Ser-Lys-Thr) (SEQ ID NO: 11) pentapeptide at the N terminus as SEQ ID NO: 3:

SEQ ID NO: 3
MIQKRKRTVSFRLVLMCTLLFVSLPITKTSAQASKTEMKDDFAKLEEQFDA

KLGIFALDTGTNRTVAYRPDERFAFASTIKALTVGVLLQQKSIEDLNQRIT

YTRDDLVNYNPITEKHVDTGMTLKELADASLRYSDNAAQNLILKQIGGPES

LKKELRKIGDEVTNPERFEPELNEVNPGETQDTSTARALVTSLRAFALEDK

LPSEKRELLIDWMKRNTTGDALIRAGVPDGWEVADKTGAASYGTRNDIAII

WPPKGDPVVLAVLSSRDKKDAKYDDKLIAEATKVVMKALNMNGK

In some embodiments, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 3.

Further, the beta-lactamase polypeptide may include additional upstream residues from the first residue of SEQ ID NO: 1 (see, e.g., *JBC* 258 (18): 11211, 1983, the contents of which are hereby incorporated by reference-including the exo-large and exo-small versions of penP and penP1). Further, the beta-lactamase polypeptide may also include additional downstream residues from the last residue of SEQ ID NO: 1.

The polynucleotide sequence of P1A (after removal of a 31 amino acid signal sequence and the QAKST (SEQ ID NO: 12) pentapeptide at the N terminus) is provided as SEQ ID NO: 2. As described herein, mutations may be made to this sequence to generate the beta-lactamase derivatives (including, taking into account degeneracy of the genetic code).

SEQ ID NO: 2
gagatgaaagatgattttgcaaaacttgaggaacaatttgatgcaaaactc gggatctttgcattggatacaggtacaaaccggacggtagcgtatcggccg -continued gatgagcgttttgcttttgcttcgacgattaaggctttaactgtaggcgtg cttttgcaacagaaatcaatagaagatctgaaccagagaataacatataca cgtgatgatcttgtaaactacaacccgattacggaaaagcacgttgatacg ggaatgacgctcaaagagcttgcggatgcttcgcttcgatatagtgacaat gcggcacagaatctcattcttaaacaaattggcggacctgaaagtttgaaa aaggaactgaggaagattggtgatgaggttacaaatcccgaacgattcgaa ccagagttaaatgaagtgaatccgggtgaaactcaggataccagtacagca agagcacttgtcacaagccttcgagcctttgctcttgaagataaacttcca agtgaaaaacgcgagcttttaatcgattggatgaaacgaaataccactgga gacgccttaatccgtgccggtgtgccggacggttgggaagtggctgataaa actggagcggcatcatatggaacccggaatgacattgccatcatttggccg ccaaaaggagatcctgtcgttcttgcagtattatccagcagggataaaaag gacgccaagtatgatgataaacttattgcagaggcaacaaaggtggtaatg aaagccttaaacatgaacggcaaataa In some embodiments, the polynucleotide of the present invention has at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 2.

Also provided is the polynucleotide sequence of P1A before the removal of a 31 amino acid signal sequence and the QASKT (SEQ ID NO: 11) pentapeptide at the N terminus as SEQ ID NO: 4. As described herein, mutations may be made to this sequence to generate beta-lactamase derivatives (including, taking into account degeneracy of the genetic code).

SEQ ID NO: 4
atgattcaaaaacgaaagcggacagtttcgttcagacttgtgcttatgtgc acgctgttatttgtcagtttgccgattacaaaaacatcagcgcaagcttcc aagacggagatgaaagatgattttgcaaaacttgaggaacaatttgatgca aaactcgggatctttgcattggatacaggtacaaaccggacggtagcgtat cggccggatgagcgttttgcttttgcttcgacgattaaggctttaactgta ggcgtgcttttgcaacagaaatcaatagaagatctgaaccagagaataaca tatacacgtgatgatcttgtaaactacaacccgattacggaaaagcacgtt gatacgggaatgacgctcaaagagcttgcggatgcttcgcttcgatatagt gacaatgcggcacagaatctcattcttaaacaaattggcggacctgaagt ttgaaaaaggaactgaggaagattggtgatgaggttacaaatcccgaacga ttcgaaccagagttaaatgaagtgaatccgggtgaaactcaggataccagt acagcaagagcacttgtcacaagccttcgagcctttgctcttgaagataaa cttccaagtgaaaaacgcgagcttttaatcgattggatgaaacgaaatacc actggagacgccttaatccgtgccggtgtgccggacggttgggaagtggct gataaaactggagcggcatcatatggaacccggaatgacattgccatcatt tggccgccaaaaggagatcctgtcgttcttgcagtattatccagcagggat aaaaaggacgccaagtatgatgataaacttattgcagaggcaacaaaggtg gtaatgaaagccttaaacatgaacggcaaataa In some embodiments, the polynucleotide of the present invention has at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 4.

In some embodiments, mutagenesis of a beta-lactamase (e.g. a class A beta-lactamase) is performed to derive advantageous enzymes (e.g. those that can target a broad spectra of antibiotics). In some embodiments, beta-lactamases derivatives are obtained by site-directed mutagenesis, random mutagenesis, and/or directed evolution approaches. In some embodiments, mutation design is based on, inter alia, structural data (e.g. crystal structure data, homolog models, etc.) of the following: P1A crystal structure (Knox and Moews, J. Mol Biol., 220, 435-455 (1991)), CTX-M-44 (1BZA (Ibuka et al. *Journal of Molecular Biology* Volume 285, Issue 5 2079-2087 (1999), 1IYS (Ibuka et al. *Biochemistry*, 2003, 42 (36): 10634-43), 1IYO, 1IYP and 1IYQ (Shimamura et al. 2002 *J. Biol. Chem.* 277:46601-08), *Proteus vulgaris* K1 (1HZO, Nugaka et al. *J Mol Biol.* 2002 Mar. 15; 317(1):109-17) and *Proteus penneri* HugA (Liassine et al. *Antimicrob Agents Chemother.* 2002 January; 46(1):216-9. 2002), and reviewed in Bonnet, *Antimicrob. Agents Chemother* 48(1): 1-14 (2004) (for CTM-X), the contents of all of these documents are hereby incorporated by reference in their entirety). In some embodiments, the present mutations are informed by analysis of structural data (e.g. crystal structure data, homolog models, etc.) of any one of the following beta-lactamases: P1A (see, e.g. U.S. Pat. No. 5,607,671, the contents of which are hereby incorporated by reference), P2A (see, e.g., WO 2007/147945, the contents of which are hereby incorporated by reference), P3A (see, e.g., WO 2011/148041, the contents of which are hereby incorporated by reference), CTX-M-3, CTX-M-4, CTX-M-5, CTX-M-9, CTX-M-10, CTX-M-14, CTX-M-15, CTX-M-16, CTX-M-18, CTX-M-19, CTX-M-25, CTX-M-26, CTX-M-27, CTX-M-32, CTX-M-44, CTX-M-45, and CTX-M-54. Such information is available to one skilled in the art at known databases, for example, Swiss-Prot Protein Sequence Data Bank, NCBI, and PDB.

In some embodiments, the beta-lactamase polypeptide produced by methods of the invention includes one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) mutations relative to SEQ ID NO: 1 or SEQ ID NO: 3 or a sequence with at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 1 or SEQ ID NO: 3 (or about 60%, about 65%, about 70%, or about 75%, or about 80%, or about 85%, or about 90, or about 95%, or about 96%, or about 97%, or about 98%, or about 99% identity to SEQ ID NO: 1 or SEQ ID NO: 3). In various embodiments, one or more amino acid of SEQ ID NO: 1 or SEQ ID NO: 3 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In illustrative embodiments, inventive mutations include, but are not limited to one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) of the following mutations to SEQ ID NO: 1 or SEQ ID NO: 3 or a sequence with at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 1 or SEQ ID NO: 3 (or about 70%, or about 75%, or about 80%, or about 85%, or about 90, or about 95%, or about 96%, or about 97%, or about 98%, or about 99% identity to SEQ ID NO: 1 or SEQ ID NO: 3): Glu1Ala; Glu1Cys; Glu1Asp; Glu1Phe; Glu1Gly; Glu1 His; Glu1Ile; Met1Lys; Glu1Leu; Glu1Met; Glu1Asn; Glu1Pro; Glu1Gln; Glu1Arg; Glu1Ser; Glu1Thr; Glu1Val; Glu1Trp; Glu1Tyr; Met2Ala; Met2Cys; Met2Asp; Met2Glu; Met2Phe; Met2Gly; Met2His; Met2Ile; Met1Lys; Met2Leu; Met2Asn; Met2Pro; Met2Gln; Met2Arg; Met2Ser; Met2Thr; Met2Val; Met2Trp; Met2Tyr; Lys3Ala; Lys3Cys; Lys3Asp; Lys3Glu; Lys3Phe; Lys3Gly; Lys3His; Lys3Ile; Lys3Leu; Lys3Met; Lys3Asn; Lys3Pro; Lys3Gln; Lys3Arg; Lys3Ser; Lys3Thr; Lys3Val; Lys3Trp; Lys3Tyr; Asp4Ala; Asp4Cys; Asp4Glu; Asp4Phe; Asp4Gly; Asp4His; Asp4Ile; Asp4Lys; Asp4Leu; Asp4Met; Asp4Asn; Asp4Pro; Asp4Gln; Asp4Arg; Asp4Ser; Asp4Thr; Asp4Val; Asp4Trp; Asp4Tyr; Asp5Ala; Asp5Cys; Asp5Glu; Asp5Phe; Asp5Gly; Asp5His; Asp5Ile; Asp5Lys; Asp5Leu; Asp5Met; Asp5Asn; Asp5Pro; Asp5Gln; Asp5Arg; Asp5Ser; Asp5Thr; Asp5Val; Asp5Trp; Asp5Tyr; Phe6Ala; Phe6Cys; Phe6Asp; Phe6Glu; Phe6Gly; Phe6His; Phe6Ile; Phe6Lys; Phe6Leu; Phe6Met; Phe6Asn; Phe6Pro; Phe6Gln; Phe6Arg; Phe6Ser; Phe6Thr; Phe6Val; Phe6Trp; Phe6Tyr; Ala7Cys; Ala7Asp; Ala7Glu; Ala7Phe; Ala7Gly; Ala7His; Ala7Ile; Ala7Lys; Ala7Leu; Ala7Met; Ala7Asn; Ala7Pro; Ala7Gln; Ala7Arg; Ala7Ser; Ala7Thr; Ala7Val; Ala7Trp; Ala7Tyr; Lys8Ala; Lys8Cys; Lys8Asp; Lys8Glu; Lys8Phe; Lys8Gly; Lys8His; Lys8Ile; Lys8Leu; Lys8Met; Lys8Asn; Lys8Pro; Lys8Gln; Lys8Arg; Lys8Ser; Lys8Thr; Lys8Val; Lys8Trp; Lys8Tyr; Leu9Ala; Leu9Cys; Leu9Asp; Leu9Glu; Leu9Phe; Leu9Gly; Leu9His; Leu9Ile; Leu9Lys; Leu9Met; Leu9Asn; Leu9Pro; Leu9Gln; Leu9Arg; Leu9Ser; Leu9Thr; Leu9Val; Leu9Trp; Leu9Tyr; Glu10Ala; Glu10Cys; Glu10Asp; Glu10Phe; Glu10Gly; Glu10His; Glu10Ile; Glu10Lys; Glu10Leu; Glu10Met; Glu10Asn; Glu10Pro; Glu10Gln; Glu10Arg; Glu10Ser; Glu10Thr; Glu10Val; Glu10Trp; Glu10Tyr; Glu11Ala; Glu11Cys; Glu11Asp; Glu11Phe; Glu11Gly; Glu11His; Glu11Ile; Glu11Lys; Glu11Leu; Glu11Met; Glu11Asn; Glu11Gln; Glu11Gln; Glu11Arg; Glu11Ser; Glu11Thr; Glu11Val; Glu11Trp; Glu11Tyr; Gln12Ala; Gln12Cys; Gln12Asp; Gln12Glu; Gln12Phe; Gln12Gly; Gln12His; Gln12Ile; Gln12Lys; Gln12Leu; Gln12Met; Gln12Asn; Gln12Pro; Gln12Arg; Gln12Ser; Gln12Thr; Gln12Val; Gln12Trp; Gln12Tyr; Phe13Ala; Phe13Cys; Phe13Asp; Phe13Glu; Phe13Gly; Phe13His; Phe13Ile; Phe13Lys; Phe13Leu; Phe13Met; Phe13Asn; Phe13Pro; Phe13Gln; Phe13Arg; Phe13Ser; Phe13Thr; Phe13Val; Phe13Trp; Phe13Tyr; Asp14Ala; Asp14Cys; Asp14Glu; Asp14Phe; Asp14Gly; Asp14His; Asp14Ile; Asp14Lys; Asp14Leu; Asp14Met; Asp14Asn; Asp14Pro; Asp14Gln; Asp14Arg; Asp14Ser; Asp14Thr; Asp14Val; Asp14Trp; Asp14Tyr; Ala15Cys; Ala15Asp; Ala15Glu; Ala15Phe; Ala15Gly; Ala15His; Ala15Ile; Ala15Lys; Ala15Leu; Ala15Met; Ala15Asn; Ala15Pro; Ala15Gln; Ala15Arg; Ala15Ser; Ala15Thr; Ala15Val; Ala15Trp; Ala15Tyr; Lys16Ala; Lys16Cys; Lys16Asp; Lys16Glu; Lys16Phe; Lys16Gly; Lys16His; Lys16Ile; Lys16Leu; Lys16Met; Lys16Asn; Lys16Pro; Lys16Gln; Lys16Arg; Lys16Ser; Lys16Thr; Lys16Val; Lys16Trp; Lys16Tyr; Leu17Ala; Leu17Cys; Leu17Asp; Leu17Glu; Leu17Phe; Leu17Gly; Leu17His; Leu17Ile; Leu17Lys; Leu17Met; Leu17Asn; Leu17Pro; Leu17Gln; Leu17Arg; Leu17Ser; Leu17Thr; Leu17Val; Leu17Trp; Leu17Tyr; Gly18Ala; Gly18Cys; Gly18Asp; Gly18Glu; Gly18Phe; Gly18His; Gly18Ile; Gly18Lys; Gly18Leu; Gly18Met; Gly18Asn; Gly18Pro; Gly18Gln; Gly18Arg; Gly18Ser; Gly18Thr; Gly18Val; Gly18Trp; Gly18Tyr; Ile19Ala; Ile19Cys; Ile19Asp; Ile19Glu; Ile19Phe; Ile19Gly; Ile19His; Ile19Lys; Ile19Leu; Ile19Met; Ile19Asn; Ile19Pro; Ile19Gln; Ile19Arg; Ile19Ser; Ile19Thr; Ile19Val; Ile19Trp; Ile19Tyr; Phe20Ala; Phe20Cys; Phe20Asp; Phe20Glu; Phe20Gly; Phe20His; Phe20Ile; Phe20Lys; Phe20Leu; Phe20Met; Phe20Asn; Phe20Pro; Phe20Gln; Phe20Arg; Phe20Ser; Phe20Thr; Phe20Val; Phe20Trp; Phe20Tyr; Ala21Cys; Ala21Asp; Ala21Glu; Ala21Phe; Ala21Gly; Ala21His; Ala21Ile; Ala21Lys; Ala21Leu; Ala21Met; Ala21Asn; Ala21Pro; Ala21Gln; Ala21Arg; Ala21Ser; Ala21Thr; Ala21Val; Ala21Trp; Ala21Tyr; Leu22Ala; Leu22Cys; Leu22Asp; Leu22Glu; Leu22Phe; Leu22Gly; Leu22His; Leu22Ile; Leu22Lys; Leu22Met; Leu22Asn; Leu22Pro; Leu22Gln; Leu22Arg; Leu22Ser; Leu22Thr; Leu22Val; Leu22Trp; Leu22Tyr; Asp23Ala; Asp23Cys; Asp23Glu; Asp23Phe; Asp23Gly; Asp23His; Asp23Ile; Asp23Lys; Asp23Leu;

Asp23Met; Asp23Asn; Asp23Pro; Asp23Gln; Asp23Arg; Asp23Ser; Asp23Thr; Asp23Val; Asp23Trp; Asp23Tyr; Thr24Ala; Thr24Cys; Thr24Asp; Thr24Glu; Thr24Phe; Thr24Gly; Thr24His; Thr24Ile; Thr24Lys; Thr24Leu; Thr24Met; Thr24Asn; Thr24Pro; Thr24Gln; Thr24Arg; Thr24Ser; Thr24Val; Thr24Trp; Thr24Tyr; Gly25Ala; Gly25Cys; Gly25Asp; Gly25Glu; Gly25Phe; Gly25His; Gly25Ile; Gly25Lys; Gly25Leu; Gly25Met; Gly25Asn; Gly25Pro; Gly25Gln; Gly25Arg; Gly25Ser; Gly25Thr; Gly25Val; Gly25Trp; Gly25Tyr; Thr26Ala; Thr26Cys; Thr26Asp; Thr26Glu; Thr26Phe; Thr26Gly; Thr26His; Thr26Ile; Thr26Lys; Thr26Leu; Thr26Met; Thr26Asn; Thr26Pro; Thr26Gln; Thr26Arg; Thr26Ser; Thr26Val; Thr26Trp; Thr26Tyr; Asn27Ala; Asn27Cys; Asn27Asp; Asn27Glu; Asn27Phe; Asn27Gly; Asn27His; Asn27Ile; Asn27Lys; Asn27Leu; Asn27Met; Asn27Pro; Asn27Gln; Asn27Arg; Asn27Ser; Asn27Thr; Asn27Val; Asn27Trp; Asn27Tyr; Arg28Ala; Arg28Cys; Arg28Asp; Arg28Glu; Arg28Phe; Arg28Gly; Arg28His; Arg28Ile; Arg28Lys; Arg28Leu; Arg28Met; Arg28Asn; Arg28Pro; Arg28Gln; Arg28Ser; Arg28Thr; Arg28Val; Arg28Trp; Arg28Tyr; Thr29Ala; Thr29Cys; Thr29Asp; Thr29Glu; Thr29Phe; Thr29Gly; Thr29His; Thr29Ile; Thr29Lys; Thr29Leu; Thr29Met; Thr29Asn; Thr29Pro; Thr29Gln; Thr29Arg; Thr29Ser; Thr29Val; Thr29Trp; Thr29Tyr; Val30Ala; Val30Cys; Val30Asp; Val30Glu; Val30Phe; Val30Gly; Val30His; Val30Ile; Val30Lys; Val30Leu; Val30Met; Val30Asn; Val30Pro; Val30Gln; Val30Arg; Val30Ser; Val30Thr; Val30Trp; Val30Tyr; Ala31Ala; Ala31Cys; Ala31Asp; Ala31Glu; Ala31Phe; Ala31Gly; Ala31His; Ala31Ile; Ala31Lys; Ala31Leu; Ala31Met; Ala31Asn; Ala31Pro; Ala31Gln; Ala31Arg; Ala31Ser; Ala31Thr; Ala31Val; Ala31Trp; Ala31Tyr; Tyr32Ala; Tyr32Cys; Tyr32Asp; Tyr32Glu; Tyr32Phe; Tyr32Gly; Tyr32His; Tyr32Ile; Tyr32Lys; Tyr32Leu; Tyr32Met; Tyr32Asn; Tyr32Pro; Tyr32Gln; Tyr32Arg; Tyr32Ser; Tyr32Thr; Tyr32Val; Tyr32Trp; Arg33Ala; Arg33Cys; Arg33Asp; Arg33Glu; Arg33Phe; Arg33Gly; Arg33His; Arg33Ile; Arg33Lys; Arg33Leu; Arg33Met; Arg33Asn; Arg33Pro; Arg33Gln; Arg33Ser; Arg33Thr; Arg33Val; Arg33Trp; Arg33Tyr; Pro34Ala; Pro34Cys; Pro34Asp; Pro34Glu; Pro34Phe; Pro34Gly; Pro34His; Pro34Ile; Pro34Lys; Pro34Leu; Pro34Met; Pro34Asn; Pro34Gln; Pro34Arg; Pro34Ser; Pro34Thr; Pro34Val; Pro34Trp; Pro34Tyr; Asp35Ala; Asp35Cys; Asp35Glu; Asp35Phe; Asp35Gly; Asp35His; Asp35Ile; Asp35Lys; Asp35Leu; Asp35Met; Asp35Asn; Asp35Pro; Asp35Gln; Asp35Arg; Asp35Ser; Asp35Thr; Asp35Val; Asp35Trp; Asp35Tyr; Glu36Ala; Glu36Cys; Glu36Asp; Glu36Phe; Glu36Gly; Glu36His; Glu36Ile; Glu36Lys; Glu36Leu; Glu36Met; Glu36Asn; Glu36Pro; Glu36Gln; Glu36Arg; Glu36Ser; Glu36Thr; Glu36Val; Glu36Trp; Glu36Tyr; Arg37Ala; Arg37Cys; Arg37Asp; Arg37Glu; Arg37Phe; Arg37Gly; Arg37His; Arg37Ile; Arg37Lys; Arg37Leu; Arg37Met; Arg37Asn; Arg37Pro; Arg37Gln; Arg37Ser; Arg37Thr; Arg37Val; Arg37Trp; Arg37Tyr; Phe38Ala; Phe38Cys; Phe38Asp; Phe38Glu; Phe38Gly; Phe38His; Phe38Ile; Phe38Lys; Phe38Leu; Phe38Met; Phe38Asn; Phe38Pro; Phe38Gln; Phe38Arg; Phe38Ser; Phe38Thr; Phe38Val; Phe38Trp; Phe38Tyr; Ala39Cys; Ala39Asp; Ala39Glu; Ala39Phe; Ala39Gly; Ala39His; Ala39Ile; Ala39Lys; Ala39Leu; Ala39Met; Ala39Asn; Ala39Pro; Ala39Gln; Ala39Arg; Ala39Ser; Ala39Thr; Ala39Val; Ala39Trp; Ala39Tyr; Phe40Ala; Phe40Cys; Phe40Asp; Phe40Glu; Phe40Gly; Phe40His; Phe40Ile; Phe40Lys; Phe40Leu; Phe40Met; Phe40Asn; Phe40Pro; Phe40Gln; Phe40Arg; Phe40Ser; Phe40Thr; Phe40Val; Phe40Trp; Phe40Tyr; Ala41Cys; Ala41Asp; Ala41Glu; Ala41Phe; Ala41Gly; Ala41His; Ala41Ile; Ala41Lys; Ala41Leu; Ala41Met; Ala41Asn; Ala41Pro; Ala41Gln; Ala41Arg; Ala41Ser; Ala41Thr; Ala41Val; Ala41Trp; Ala41Tyr; Ser42Ala; Ser42Cys; Ser42Asp; Ser42Glu; Ser42Phe; Ser42Gly; Ser42His; Ser42Ile; Ser42Lys; Ser42Leu; Ser42Met; Ser42Asn; Ser42Pro; Ser42Gln; Ser42Arg; Ser42Thr; Ser42Val; Ser42Trp; Ser42Tyr; Thr43Ala; Thr43Cys; Thr43Asp; Thr43Glu; Thr43Phe; Thr43Gly; Thr43His; Thr43Ile; Thr43Lys; Thr43Leu; Thr43Met; Thr43Asn; Thr43Pro; Thr43Gln; Thr43Arg; Thr43Ser; Thr43Val; Thr43Trp; Thr43Tyr; Ile44Ala; Ile44Cys; Ile44Asp; Ile44Glu; Ile44Phe; Ile44Gly; Ile44His; Ile44Lys; Ile44Leu; Ile44Met; Ile44Asn; Ile44Pro; Ile44Gln; Ile44Arg; Ile44Ser; Ile44Thr; Ile44Val; Ile44Trp; Ile44Tyr; Lys45Ala; Lys45Cys; Lys45Asp; Lys45Glu; Lys45Phe; Lys45Gly; Lys45His; Lys45Ile; Lys45Leu; Lys45Met; Lys45Asn; Lys45Pro; Lys45Gln; Lys45Arg; Lys45Ser; Lys45Thr; Lys45Val; Lys45Trp; Lys45Tyr; Ala46Cys; Ala46Asp; Ala46Glu; Ala46Phe; Ala46Gly; Ala46His; Ala46Ile; Ala46Lys; Ala46Leu; Ala46Met; Ala46Asn; Ala46Pro; Ala46Gln; Ala46Arg; Ala46Ser; Ala46Thr; Ala46Val; Ala46Trp; Ala46Tyr; Leu47Ala; Leu47Cys; Leu47Asp; Leu47Glu; Leu47Phe; Leu47Gly; Leu47His; Leu47Ile; Leu47Lys; Leu47Met; Leu47Asn; Leu47Pro; Leu47Gln; Leu47Arg; Leu47Ser; Leu47Thr; Leu47Val; Leu47Trp; Leu47Tyr; Thr48Ala; Thr48Cys; Thr48Asp; Thr48Glu; Thr48Phe; Thr48Gly; Thr48His; Thr48Ile; Thr48Lys; Thr48Leu; Thr48Met; Thr48Asn; Thr48Pro; Thr48Gln; Thr48Arg; Thr48Ser; Thr48Val; Thr48Trp; Thr48Tyr; Val49Ala; Val49Cys; Val49Asp; Val49Glu; Val49Phe; Val49Gly; Val49His; Val49Ile; Val49Lys; Val49Leu; Val49Met; Val49Asn; Val49Pro; Val49Gln; Val49Arg; Val49Ser; Val49Thr; Val49Trp; Val49Tyr; Gly50Ala; Gly50Cys; Gly50Asp; Gly50Glu; Gly50Phe; Gly50His; Gly50Ile; Gly50Lys; Gly50Leu; Gly50Met; Gly50Asn; Gly50Pro; Gly50Gln; Gly50Arg; Gly50Ser; Gly50Thr; Gly50Val; Gly50Trp; Gly50Tyr; Val51Ala; Val51Cys; Val51Asp; Val51Glu; Val51Phe; Val51Gly; Val51His; Val51Ile; Val51Lys; Val51Leu; Val51Met; Val51Asn; Val51Pro; Val51Gln; Val51Arg; Val51Ser; Val51Thr; Val51Trp; Val51Tyr; Leu52Ala; Leu52Cys; Leu52Asp; Leu52Glu; Leu52Phe; Leu52Gly; Leu52His; Leu52Ile; Leu52Lys; Leu52Met; Leu52Asn; Leu52Pro; Leu52Gln; Leu52Arg; Leu52Ser; Leu52Thr; Leu52Val; Leu52Trp; Leu52Tyr; Leu53Ala; Leu53Cys; Leu53Asp; Leu53Glu; Leu53Phe; Leu53Gly; Leu53His; Leu53Ile; Leu53Lys; Leu53Met; Leu53Asn; Leu53Pro; Leu53Gln; Leu53Arg; Leu53Ser; Leu53Thr; Leu53Val; Leu53Trp; Leu53Tyr; Gln54Ala; Gln54Cys; Gln54Asp; Gln54Glu; Gln54Phe; Gln54Gly; Gln54His; Gln54Ile; Gln54Lys; Gln54Leu; Gln54Met; Gln54Asn; Gln54Pro; Gln54Arg; Gln54Ser; Gln54Thr; Gln54Val; Gln54Trp; Gln54Tyr; Gln55Ala; Gln55Cys; Gln55Asp; Gln55Glu; Gln55Phe; Gln55Gly; Gln55His; Gln55Ile; Gln55Lys; Gln55Leu; Gln55Met; Gln55Asn; Gln55Pro; Gln55Arg; Gln55Ser; Gln55Thr; Gln55Val; Gln55Trp; Gln55Tyr; Lys56Ala; Lys56Cys; Lys56Asp; Lys56Glu; Lys56Phe; Lys56Gly; Lys56His; Lys56Ile; Lys56Leu; Lys56Met; Lys56Asn; Lys56Pro; Lys56Gln; Lys56Arg; Lys56Ser; Lys56Thr; Lys56Val; Lys56Trp; Lys56Tyr; Ser57Ala; Ser57Cys; Ser57Asp; Ser57Glu; Ser57Phe; Ser57Gly; Ser57His; Ser57Ile; Ser57Lys; Ser57Leu; Ser57Met; Ser57Asn; Ser57Pro; Ser57Gln; Ser57Arg; Ser57Thr; Ser57Val; Ser57Trp; Ser57Tyr; Ile58Ala; Ile58Cys; Ile58Asp; Ile58Glu; Ile58Phe; Ile58Gly; Ile58His; Ile58Lys; Ile58Leu; Ile58

Ile58Val; Ile58Trp; Ile58Tyr; Glu59Ala; Glu59Cys; Glu59Asp; Glu59Phe; Glu59Gly; Glu59His; Glu59Ile; Glu59Lys; Glu59Leu; Glu59Met; Glu59Asn; Glu59Pro; Glu59Gln; Glu59Ser; Glu59Thr; Glu59Val; Glu59Trp; Glu59Tyr; Asp60Ala; Asp60Cys; Asp60Glu; Asp60Phe; Asp60Gly; Asp60His; Asp60Ile; Asp60Lys; Asp60Leu; Asp60Met; Asp60Asn; Asp60Pro; Asp60Gln; Asp60Arg; Asp60Ser; Asp60Thr; Asp60Val; Asp60Trp; Asp60Tyr; Leu61Ala; Leu61Cys; Leu61Asp; Leu61Glu; Leu61Phe; Leu61Gly; Leu61His; Leu61Ile; Leu61Lys; Leu61Met; Leu61Asn; Leu61Pro; Leu61Gln; Leu61Arg; Leu61Ser; Leu61Thr; Leu61Val; Leu61Trp; Leu61Tyr; Asn62Ala; Asn62Cys; Asn62Asp; Asn62Glu; Asn62Phe; Asn62Gly; Asn62His; Asn62Ile; Asn62Lys; Asn62Leu; Asn62Met; Asn62Pro; Asn62Gln; Asn62Arg; Asn62Ser; Asn62Thr; Asn62Val; Asn62Trp; Asn62Tyr; Gln63Ala; Gln63Cys; Gln63Asp; Gln63Glu; Gln63Phe; Gln63Gly; Gln63His; Gln63Ile; Gln63Lys; Gln63Leu; Gln63Met; Gln63Asn; Gln63Pro; Gln63Arg; Gln63Ser; Gln63Thr; Gln63Val; Gln63Trp; Gln63Tyr; Arg64Ala; Arg64Cys; Arg64Asp; Arg64Glu; Arg64Phe; Arg64Gly; Arg64His; Arg64Ile; Arg64Lys; Arg64Leu; Arg64Met; Arg64Asn; Arg64Pro; Arg64Gln; Arg64Ser; Arg64Thr; Arg64Val; Arg64Trp; Arg64Tyr; Ile65Ala; Ile65Cys; Ile65Asp; Ile65Glu; Ile65Phe; Ile65Gly; Ile65His; Ile65Lys; Ile65Leu; Ile65Met; Ile65Asn; Ile65Pro; Ile65Gln; Ile65Arg; Ile65Ser; Ile65Thr; Ile65Val; Ile65Trp; Ile65Tyr; Thr66Ala; Thr66Cys; Thr66Asp; Thr66Glu; Thr66Phe; Thr66Gly; Thr66His; Thr66Ile; Thr66Lys; Thr66Leu; Thr66Met; Thr66Asn; Thr66Pro; Thr66Gln; Thr66Arg; Thr66Ser; Thr66Val; Thr66Trp; Thr66Tyr; Tyr67Ala; Tyr67Cys; Tyr67Asp; Tyr67Glu; Tyr67Phe; Tyr67Gly; Tyr67His; Tyr67Ile; Tyr67Lys; Tyr67Leu; Tyr67Met; Tyr67Asn; Tyr67Pro; Tyr67Gln; Tyr67Arg; Tyr67Ser; Tyr67Thr; Tyr67Val; Tyr67Trp; Thr68Ala; Thr68Cys; Thr68Asp; Thr68Glu; Thr68Phe; Thr68Gly; Thr68His; Thr68Ile; Thr68Lys; Thr68Leu; Thr68Met; Thr68Asn; Thr68Pro; Thr68Gln; Thr68Arg; Thr68Ser; Thr68Val; Thr68Trp; Thr68Tyr; Arg69Ala; Arg69Cys; Arg69Asp; Arg69Glu; Arg69Phe; Arg69Gly; Arg69His; Arg69Ile; Arg69Lys; Arg69Leu; Arg69Met; Arg69Asn; Arg69Pro; Arg69Gln; Arg69Ser; Arg69Thr; Arg69Val; Arg69Trp; Arg69Tyr; Asp70Ala; Asp70Cys; Asp70Glu; Asp70Phe; Asp70Gly; Asp70His; Asp70Ile; Asp70Lys; Asp70Leu; Asp70Met; Asp70Asn; Asp70Pro; Asp70Gln; Asp70Arg; Asp70Ser; Asp70Thr; Asp70Val; Asp70Trp; Asp70Tyr; Asp71Ala; Asp71Cys; Asp71Glu; Asp71Phe; Asp71Gly; Asp71His; Asp71Ile; Asp71Lys; Asp71Leu; Asp71Met; Asp71Asn; Asp71Pro; Asp71Gln; Asp71Arg; Asp71Ser; Asp71Thr; Asp71Val; Asp71Trp; Asp71Tyr; Leu72Ala; Leu72Cys; Leu72Asp; Leu72Glu; Leu72Phe; Leu72Gly; Leu72His; Leu72Ile; Leu72Lys; Leu72Met; Leu72Asn; Leu72Pro; Leu72Gln; Leu72Arg; Leu72Ser; Leu72Thr; Leu72Val; Leu72Trp; Leu72Tyr; Val73Ala; Val73Cys; Val73Asp; Val73Glu; Val73Phe; Val73Gly; Val73His; Val73Ile; Val73Lys; Val73Leu; Val73Met; Val73Asn; Val73Pro; Val73Gln; Val73Arg; Val73Ser; Val73Thr; Val73Trp; Val73Tyr; Asn74Ala; Asn74Cys; Asn74Asp; Asn74Glu; Asn74Phe; Asn74Gly; Asn74His; Asn74Ile; Asn74Lys; Asn74Leu; Asn74Met; Asn74Pro; Asn74Gln; Asn74Arg; Asn74Ser; Asn74Thr; Asn74Val; Asn74Trp; Asn74Tyr; Tyr75Ala; Tyr75Cys; Tyr75Asp; Tyr75Glu; Tyr75Phe; Tyr75Gly; Tyr75His; Tyr75Ile; Tyr75Lys; Tyr75Leu; Tyr75Met; Tyr75Asn; Tyr75Pro; Tyr75Gln; Tyr75Arg; Tyr75Ser; Tyr75Thr; Tyr75Val; Tyr75Trp; Asn76Ala; Asn76Cys; Asn76Asp; Asn76Glu; Asn76Phe; Asn76Gly; Asn76His; Asn76Ile; Asn76Lys; Asn76Leu; Asn76Met; Asn76Pro; Asn76Gln; Asn76Arg; Asn76Ser; Asn76Thr; Asn76Val; Asn76Trp; Asn76Tyr; Pro77Ala; Pro77Cys; Pro77Asp; Pro77Glu; Pro77Phe; Pro77Gly; Pro77His; Pro77Ile; Pro77Leu; Pro77Lys; Pro77Met; Pro77Asn; Pro77Gln; Pro77Arg; Pro77Ser; Pro77Thr; Pro77Val; Pro77Trp; Pro77Tyr; Ile78Ala; Ile78Cys; Ile78Asp; Ile78Glu; Ile78Phe; Ile78Gly; Ile78His; Ile78Lys; Ile78Leu; Ile78Met; Ile78Asn; Ile78Pro; Ile78Gln; Ile78Arg; Ile78Ser; Ile78Thr; Ile78Val; Ile78Trp; Ile78Tyr; Thr79Ala; Thr79Cys; Thr79Asp; Thr79Glu; Thr79Phe; Thr79Gly; Thr79His; Thr79Ile; Thr79Lys; Thr79Leu; Thr79Met; Thr79Asn; Thr79Pro; Thr79Gln; Thr79Arg; Thr79Ser; Thr79Val; Thr79Trp; Thr79Tyr; Glu80Ala; Glu80Cys; Glu80Asp; Glu80Phe; Glu80Gly; Glu80His; Glu80Ile; Glu80Lys; Glu80Leu; Glu80Met; Glu80Asn; Glu80Pro; Glu80Gln; Glu80Arg; Glu80Ser; Glu80Thr; Glu80Val; Glu80Trp; Glu80Tyr; Lys81Ala; Lys81Cys; Lys81Asp; Lys81Glu; Lys81Phe; Lys81Gly; Lys81His; Lys81Ile; Lys81Leu; Lys81Met; Lys81Asn; Lys81Pro; Lys81Gln; Lys81Arg; Lys81Ser; Lys81Thr; Lys81Val; Lys81Trp; Lys81Tyr; His82Ala; His82Cys; His82Asp; His82Glu; His82Phe; His82Gly; His82Ile; His82Lys; His82Leu; His82Met; His82Asn; His82Pro; His82Gln; His82Arg; His82Ser; His82Thr; His82Val; His82Trp; His82Tyr; Val83Ala; Val83Cys; Val83Asp; Val83Glu; Val83Phe; Val83Gly; Val83His; Val83Ile; Val83Lys; Val83Leu; Val83Met; Val83Asn; Val83Pro; Val83Gln; Val83Arg; Val83Ser; Val83Thr; Val83Trp; Val83Tyr; Asp84Ala; Asp84Cys; Asp84Glu; Asp84Phe; Asp84Gly; Asp84His; Asp84Ile; Asp84Lys; Asp84Leu; Asp84Met; Asp84Asn; Asp84Pro; Asp84Gln; Asp84Arg; Asp84Ser; Asp84Thr; Asp84Val; Asp84Trp; Asp84Tyr; Thr85Ala; Thr85Cys; Thr85Asp; Thr85Glu; Thr85Phe; Thr85Gly; Thr85His; Thr85Ile; Thr85Lys; Thr85Leu; Thr85Met; Thr85Asn; Thr85Pro; Thr85Gln; Thr85Arg; Thr85Ser; Thr85Val; Thr85Trp; Thr85Tyr; Gly86Ala; Gly86Cys; Gly86Asp; Gly86Glu; Gly86Phe; Gly86His; Gly86Ile; Gly86Lys; Gly86Leu; Gly86Met; Gly86Asn; Gly86Pro; Gly86Gln; Gly86Arg; Gly86Ser; Gly86Thr; Gly86Val; Gly86Trp; Gly86Tyr; Met87Ala; Met87Cys; Met87Asp; Met87Glu; Met87Phe; Met87Gly; Met87His; Met87Ile; Met87Lys; Met87Leu; Met87Asn; Met87Pro; Met87Gln; Met87Arg; Met87Ser; Met87Thr; Met87Val; Met87Trp; Met87Tyr; Thr88Ala; Thr88Cys; Thr88Asp; Thr88Glu; Thr88Phe; Thr88Gly; Thr88His; Thr88Ile; Thr88Lys; Thr88Leu; Thr88Met; Thr88Asn; Thr88Pro; Thr88Gln; Thr88Arg; Thr88Ser; Thr88Val; Thr88Trp; Thr88Tyr; Leu89Ala; Leu89Cys; Leu89Asp; Leu89Glu; Leu89Phe; Leu89Gly; Leu89His; Leu89Ile; Leu89Lys; Leu89Met; Leu89Asn; Leu89Pro; Leu89Gln; Leu89Arg; Leu89Ser; Leu89Thr; Leu89Val; Leu89Trp; Leu89Tyr; Lys90Ala; Lys90Cys; Lys90Asp; Lys90Glu; Lys90Phe; Lys90Gly; Lys90His; Lys90Ile; Lys90Leu; Lys90Met; Lys90Asn; Lys90Pro; Lys90Gln; Lys90Arg; Lys90Ser; Lys90Thr; Lys90Val; Lys90Trp; Lys90Tyr; Glu91Ala; Glu91Cys; Glu91Asp; Glu91Phe; Glu91Gly; Glu91His; Glu91Ile; Glu91Lys; Glu91Leu; Glu91Met; Glu91Asn; Glu91Pro; Glu91Gln; Glu91Arg; Glu91Ser; Glu91Thr; Glu91Val; Glu91Trp; Glu91Tyr; Leu92Ala; Leu92Cys; Leu92Asp; Leu92Glu; Leu92Phe; Leu92Gly; Leu92His; Leu92Ile; Leu92Lys; Leu92Met; Leu92Asn; Leu92Pro; Leu92Gln; Leu92Arg; Leu92Ser; Leu92Thr; Leu92Val; Leu92Trp; Leu92Tyr; Ala93Cys; Ala93Asp; Ala93Glu; Ala93Phe; Ala93Gly; Ala93His; Ala93Ile; Ala93Lys; Ala93Leu; Ala93Met; Ala93Asn; Ala93Pro; Ala93Gln; Ala93Arg; Ala93Ser; Ala93Thr; Ala93Val; Ala93Trp; Ala93Tyr; Asp94Ala; Asp94Cys; Asp94Glu; Asp94Phe; Asp94Gly; Asp94His;

Asp94Ile; Asp94Lys; Asp94Leu; Asp94Met; Asp94Asn; Asp94Pro; Asp94Gln; Asp94Arg; Asp94Ser; Asp94Thr; Asp94Val; Asp94Trp; Asp94Tyr; Ala95Cys; Ala95Asp; Ala95Glu; Ala95Phe; Ala95Gly; Ala95His; Ala95Ile; Ala95Lys; Ala95Leu; Ala95Met; Ala95Asn; Ala95Pro; Ala95Gln; Ala95Arg; Ala95Ser; Ala95Thr; Ala95Val; Ala95Trp; Ala95Tyr; Ser96Ala; Ser96Cys; Ser96Asp; Ser96Glu; Ser96Phe; Ser96Gly; Ser96His; Ser96Ile; Ser96Lys; Ser96Leu; Ser96Met; Ser96Asn; Ser96Pro; Ser96Gln; Ser96Arg; Ser96Thr; Ser96Val; Ser96Trp; Ser96Tyr; Leu97Ala; Leu97Cys; Leu97Asp; Leu97Glu; Leu97Phe; Leu97Gly; Leu97His; Leu97Ile; Leu97Lys; Leu97Met; Leu97Asn; Leu97Pro; Leu97Gln; Leu97Arg; Leu97Ser; Leu97Thr; Leu97Val; Leu97Trp; Leu97Tyr; Arg98Ala; Arg98Cys; Arg98Asp; Arg98Glu; Arg98Phe; Arg98Gly; Arg98His; Arg98Ile; Arg98Lys; Arg98Leu; Arg98Met; Arg98Asn; Arg98Pro; Arg98Gln; Arg98Ser; Arg98Thr; Arg98Val; Arg98Trp; Arg98Tyr; Tyr99Ala; Tyr99Cys; Tyr99Asp; Tyr99Glu; Tyr99Phe; Tyr99Gly; Tyr99His; Tyr99Ile; Tyr99Lys; Tyr99Leu; Tyr99Met; Tyr99Asn; Tyr99Pro; Tyr99Gln; Tyr99Arg; Tyr99Ser; Tyr99Thr; Tyr99Val; Tyr99Trp; Ser100Ala; Ser100Cys; Ser100Asp; Ser100Glu; Ser100Phe; Ser100Gly; Ser100His; Ser100Ile; Ser100Lys; Ser100Leu; Ser100Met; Ser100Asn; Ser100Pro; Ser100Gln; Ser100Arg; Ser100Thr; Ser100Val; Ser100Trp; Ser100Tyr; Asp101Ala; Asp101Cys; Asp101Glu; Asp101Phe; Asp101Gly; Asp101His; Asp101Ile; Asp101Lys; Asp101Leu; Asp101Met; Asp101Asn; Asp101Pro; Asp101Gln; Asp101Arg; Asp101Ser; Asp101Thr; Asp101Val; Asp101Trp; Asp101Tyr; Asn102Ala; Asn102Cys; Asn102Asp; Asn102Glu; Asn102Phe; Asn102Gly; Asn102His; Asn102Ile; Asn102Lys; Asn102Leu; Asn102Met; Asn102Pro; Asn102Gln; Asn102Arg; Asn102Ser; Asn102Thr; Asn102Val; Asn102Trp; Asn102Tyr; Ala103Cys; Ala103Asp; Ala103Glu; Ala103Phe; Ala103Gly; Ala103His; Ala103Ile; Ala103Lys; Ala103Leu; Ala103Met; Ala103Asn; Ala103Pro; Ala103Gln; Ala103Arg; Ala103Ser; Ala103Thr; Ala103Val; Ala103Trp; Ala103Tyr; Ala104Cys; Ala104Asp; Ala104Glu; Ala104Phe; Ala104Gly; Ala104His; Ala104Ile; Ala104Lys; Ala104Leu; Ala104Met; Ala104Asn; Ala104Pro; Ala104Gln; Ala104Arg; Ala104Ser; Ala104Thr; Ala104Val; Ala104Trp; Ala104Tyr; Gln105Ala; Gln105Cys; Gln105Asp; Gln105Glu; Gln105Phe; Gln105Gly; Gln105His; Gln105Ile; Gln105Lys; Gln105Leu; Gln105Met; Gln105Asn; Gln105Pro; Gln105Arg; Gln105Ser; Gln105Thr; Gln105Val; Gln105Trp; Gln105Tyr; Asn106Ala; Asn106Cys; Asn106Asp; Asn106Glu; Asn106Phe; Asn106Gly; Asn106His; Asn106Ile; Asn106Lys; Asn106Leu; Asn106Met; Asn106Pro; Asn106Gln; Asn106Arg; Asn106Ser; Asn106Thr; Asn106Val; Asn106Trp; Asn106Tyr; Leu107Ala; Leu107Cys; Leu107Asp; Leu107Glu; Leu107Phe; Leu107Gly; Leu107His; Leu107Ile; Leu107Lys; Leu107Met; Leu107Asn; Leu107Pro; Leu107Gln; Leu107Arg; Leu107Ser; Leu107Thr; Leu107Val; Leu107Trp; Leu107Tyr; Ile108Ala; Ile108Cys; Ile108Asp; Ile108Glu; Ile108Phe; Ile108Gly; Ile108His; Ile108Lys; Ile108Leu; Ile108Met; Ile108Asn; Ile108Pro; Ile108Gln; Ile108Arg; Ile108Ser; Ile108Thr; Ile108Val; Ile108Trp; Ile108Tyr; Leu109Ala; Leu109Cys; Leu109Asp; Leu109Glu; Leu109Phe; Leu109Gly; Leu109His; Leu109Ile; Leu109Lys; Leu109Met; Leu109Asn; Leu109Pro; Leu109Gln; Leu109Arg; Leu109Ser; Leu109Thr; Leu109Val; Leu109Trp; Leu109Tyr; Lys110Ala; Lys110Cys; Lys110Asp; Lys110Glu; Lys110Phe; Lys110Gly; Lys110His; Lys110Ile; Lys110Leu; Lys110Met; Lys110Asn; Lys110Pro; Lys110Gln; Lys110Arg; Lys110Ser; Lys110Thr; Lys110Val; Lys110Trp; Lys110Tyr; Gln111Ala; Gln111Cys; Gln111Glu; Gln111Phe; Gln111Gly; Gln111His; Gln111Ile; Gln111Lys; Gln111Leu; Gln111Met; Gln111Asn; Gln111Pro; Gln111Arg; Gln111Ser; Gln111Thr; Gln111Val; Gln111Trp; Gln111Tyr; Ile112Ala; Ile112Cys; Ile112Asp; Ile112Glu; Ile112Phe; Ile112Gly; Ile112His; Ile112Lys; Ile112Leu; Ile112Met; Ile112Asn; Ile112Pro; Ile112Gln; Ile112Arg; Ile112Ser; Ile112Thr; Ile112Val; Ile112Trp; Ile112Tyr; Gly113Ala; Gly113Cys; Gly113Asp; Gly113Glu; Gly113Phe; Gly113His; Gly113Ile; Gly113Lys; Gly113Leu; Gly113Met; Gly113Asn; Gly113Pro; Gly113Gln; Gly113Arg; Gly113Ser; Gly113Thr; Gly113Val; Gly113Trp; Gly113Tyr; Gly114Ala; Gly114Cys; Gly114Asp; Gly114Glu; Gly114Phe; Gly114His; Gly114Ile; Gly114Lys; Gly114Leu; Gly114Met; Gly114Asn; Gly114Pro; Gly114Gln; Gly114Arg; Gly114Ser; Gly114Thr; Gly114Val; Gly114Trp; Gly114Tyr; Pro115Ala; Pro115Cys; Pro115Asp; Pro115Glu; Pro115Phe; Pro115Gly; Pro115His; Pro115Ile; Pro115Lys; Pro115Leu; Pro115Met; Pro115Asn; Pro115Gln; Pro115Arg; Pro115Ser; Pro115Thr; Pro115Val; Pro115Trp; Pro115Tyr; Glu116Ala; Glu116Cys; Glu116Asp; Glu116Phe; Glu116Gly; Glu116His; Glu116Ile; Glu116Lys; Glu116Leu; Glu116Met; Glu116Asn; Glu116Pro; Glu116Gln; Glu116Arg; Glu116Ser; Glu116Thr; Glu116Val; Glu116Trp; Glu116Tyr; Ser117Ala; Ser117Cys; Ser117Asp; Ser117Glu; Ser117Phe; Ser117Gly; Ser117His; Ser117Ile; Ser117Lys; Ser117Leu; Ser117Met; Ser117Asn; Ser117Pro; Ser117Gln; Ser117Arg; Ser117Thr; Ser117Val; Ser117Trp; Ser117Tyr; Leu118Ala; Leu118Cys; Leu118Asp; Leu118Glu; Leu118Phe; Leu118Gly; Leu118His; Leu118Ile; Leu118Lys; Leu118Met; Leu118Asn; Leu118Pro; Leu118Gln; Leu118Arg; Leu118Ser; Leu118Thr; Leu118Val; Leu118Trp; Leu118Tyr; Lys119Ala; Lys119Cys; Lys119Asp; Lys119Glu; Lys119Phe; Lys119Gly; Lys119His; Lys119Ile; Lys119Leu; Lys119Met; Lys119Asn; Lys119Pro; Lys119Gln; Lys119Arg; Lys119Ser; Lys119Thr; Lys119Val; Lys119Trp; Lys119Tyr; Lys120Ala; Lys120Cys; Lys120Asp; Lys120Glu; Lys120Phe; Lys120Gly; Lys120His; Lys120Ile; Lys120Leu; Lys120Met; Lys120Asn; Lys120Pro; Lys120Gln; Lys120Arg; Lys120Ser; Lys120Thr; Lys120Val; Lys120Trp; Lys120Tyr; Glu121Ala; Glu121Cys; Glu121Asp; Glu121Phe; Glu121Gly; Glu121His; Glu121Ile; Glu121Lys; Glu121Leu; Glu121Met; Glu121Asn; Glu121Pro; Glu121Gln; Glu121Arg; Glu121Ser; Glu121Thr; Glu121Val; Glu121Trp; Glu121Tyr; Leu122Ala; Leu122Cys; Leu122Asp; Leu122Glu; Leu122Phe; Leu122Gly; Leu122His; Leu122Ile; Leu122Lys; Leu122Met; Leu122Asn; Leu122Pro; Leu122Gln; Leu122Arg; Leu122Ser; Leu122Thr; Leu122Val; Leu122Trp; Leu122Tyr; Arg123Ala; Arg123Cys; Arg123Asp; Arg123Glu; Arg123Phe; Arg123Gly; Arg123His; Arg123Ile; Arg123Lys; Arg123Leu; Arg123Met; Arg123Asn; Arg123Pro; Arg123Gln; Arg123Ser; Arg123Thr; Arg123Val; Arg123Trp; Arg123Tyr; Lys124Ala; Lys124Cys; Lys124Asp; Lys124Glu; Lys124Phe; Lys124Gly; Lys124His; Lys124Ile; Lys124Leu; Lys124Met; Lys124Asn; Lys124Pro; Lys124Gln; Lys124Arg; Lys124Ser; Lys124Thr; Lys124Val; Lys124Trp; Lys124Tyr; Ile125Ala; Ile125Asp; Ile125Glu; Ile125Phe; Ile125Gly; Ile125His; Ile125Lys; Ile125Leu; Ile125Met; Ile125Asn; Ile125Pro;

Ile125Gln; Ile125Arg; Ile125Ser; Ile125Thr; Ile125Val; Ile125Trp; Ile125Tyr; Gly126Ala; Gly126Cys; Gly126Asp; Gly126Glu; Gly126Phe; Gly126His; Gly126Ile; Gly126Lys; Gly126Leu; Gly126Met; Gly126Asn; Gly126Pro; Gly126Gln; Gly126Arg; Gly126Ser; Gly126Thr; Gly126Val; Gly126Trp; Gly126Tyr; Asp127Ala; Asp127Cys; Asp127Glu; Asp127Phe; Asp127Gly; Asp127His; Asp127Ile; Asp127Lys; Asp127Leu; Asp127Met; Asp127Asn; Asp127Pro; Asp127Gln; Asp127Arg; Asp127Ser; Asp127Thr; Asp127Val; Asp127Trp; Asp127Tyr; Glu128Ala; Glu128Cys; Glu128Asp; Glu128Phe; Glu128Gly; Glu128His; Glu128Ile; Glu128Lys; Glu128Leu; Glu128Met; Glu128Asn; Glu128Pro; Glu128Gln; Glu128Arg; Glu128Ser; Glu128Thr; Glu128Val; Glu128Trp; Glu128Tyr; Val129Ala; Val129Cys; Val129Asp; Val129Glu; Val129Phe; Val129Gly; Val129His; Val129Ile; Val129Lys; Val129Leu; Val129Met; Val129Asn; Val129Pro; Val129Gln; Val129Arg; Val129Ser; Val129Thr; Val129Trp; Val129Tyr; Thr130Ala; Thr130Cys; Thr130Asp; Thr130Glu; Thr130Phe; Thr130Gly; Thr130His; Thr130Ile; Thr130Lys; Thr130Leu; Thr130Met; Thr130Asn; Thr130Pro; Thr130Gln; Thr130Arg; Thr130Ser; Thr130Val; Thr130Trp; Thr130Tyr; Asn131Ala; Asn131Cys; Asn131Asp; Asn131Glu; Asn131Phe; Asn131Gly; Asn131His; Asn131Ile; Asn131Lys; Asn131Leu; Asn131Met; Asn131Pro; Asn131Gln; Asn131Arg; Asn131Ser; Asn131Thr; Asn131Val; Asn131Trp; Asn131Tyr; Pro132Ala; Pro132Cys; Pro132Asp; Pro132Glu; Pro132Phe; Pro132Gly; Pro132His; Pro132Ile; Pro132Lys; Pro132Leu; Pro132Met; Pro132Asn; Pro132Gln; Pro132Arg; Pro132Ser; Pro132Thr; Pro132Val; Pro132Trp; Pro132Tyr; Glu133Ala; Glu133Cys; Glu133Asp; Glu133Phe; Glu133Gly; Glu133His; Glu133Ile; Glu133Lys; Glu133Leu; Glu133Met; Glu133Asn; Glu133Pro; Glu133Gln; Glu133Arg; Glu133Ser; Glu133Thr; Glu133Val; Glu133Trp; Glu133Tyr; Arg134Ala; Arg134Cys; Arg134Asp; Arg134Glu; Arg134Phe; Arg134Gly; Arg134His; Arg134Ile; Arg134Lys; Arg134Leu; Arg134Met; Arg134Asn; Arg134Pro; Arg134Gln; Arg134Ser; Arg134Thr; Arg134Val; Arg134Trp; Arg134Tyr; Phe135Ala; Phe135Cys; Phe135Asp; Phe135Glu; Phe135Gly; Phe135His; Phe135Ile; Phe135Lys; Phe135Leu; Phe135Met; Phe135Asn; Phe135Pro; Phe135Gln; Phe135Arg; Phe135Ser; Phe135Thr; Phe135Val; Phe135Trp; Phe135Tyr; Glu136Ala; Glu136Cys; Glu136Asp; Glu136Phe; Glu136Gly; Glu136His; Glu136Ile; Glu136Lys; Glu136Leu; Glu136Met; Glu136Asn; Glu136Pro; Glu136Gln; Glu136Arg; Glu136Ser; Glu136Thr; Glu136Val; Glu136Trp; Glu136Tyr; Pro137Ala; Pro137Cys; Pro137Asp; Pro137Glu; Pro137Phe; Pro137Gly; Pro137His; Pro137Ile; Pro137Lys; Pro137Leu; Pro137Met; Pro137Asn; Pro137Gln; Pro137Arg; Pro137Ser; Pro137Thr; Pro137Val; Pro137Trp; Pro137Tyr; Glu138Ala; Glu138Cys; Glu138Asp; Glu138Phe; Glu138Gly; Glu138His; Glu138Ile; Glu138Lys; Glu138Leu; Glu138Met; Glu138Asn; Glu138Pro; Glu138Gln; Glu138Arg; Glu138Ser; Glu138Thr; Glu138Val; Glu138Trp; Glu138Tyr; Leu139Ala; Leu139Cys; Leu139Asp; Leu139Glu; Leu139Phe; Leu139Gly; Leu139His; Leu139Ile; Leu139Lys; Leu139Met; Leu139Asn; Leu139Pro; Leu139Gln; Leu139Arg; Leu139Ser; Leu139Thr; Leu139Val; Leu139Trp; Leu139Tyr; Asn140Ala; Asn140Cys; Asn140Asp; Asn140Glu; Asn140Phe; Asn140Gly; Asn140His; Asn140Ile; Asn140Lys; Asn140Leu; Asn140Met; Asn140Pro; Asn140Gln; Asn140Arg; Asn140Ser; Asn140Thr; Asn140Val; Asn140Trp; Asn140Tyr; Glu141Ala; Glu141Cys; Glu141Asp; Glu141Phe; Glu141Gly; Glu141His; Glu141Ile; Glu141Lys; Glu141Leu; Glu141Met; Glu141Asn; Glu141Pro; Glu141Gln; Glu141Arg; Glu141Ser; Glu141Thr; Glu141Val; Glu141Trp; Glu141Tyr; Val142Ala; Val142Cys; Val142Asp; Val142Glu; Val142Phe; Val142Gly; Val142His; Val142Ile; Val142Lys; Val142Leu; Val142Met; Val142Asn; Val142Pro; Val142Gln; Val142Arg; Val142Ser; Val142Thr; Val142Trp; Val142Tyr; Asn143Ala; Asn143Cys; Asn143Asp; Asn143Glu; Asn143Phe; Asn143Gly; Asn143His; Asn143Ile; Asn143Lys; Asn143Leu; Asn143Met; Asn143Pro; Asn143Gln; Asn143Arg; Asn143Ser; Asn143Thr; Asn143Val; Asn143Trp; Asn143Tyr; Pro144Ala; Pro144Cys; Pro144Asp; Pro144Glu; Pro144Phe; Pro144Gly; Pro144His; Pro144Ile; Pro144Lys; Pro144Leu; Pro144Met; Pro144Asn; Pro144Gln; Pro144Arg; Pro144Ser; Pro144Thr; Pro144Val; Pro144Trp; Pro144Tyr; Gly145Ala; Gly145Cys; Gly145Asp; Gly145Glu; Gly145Phe; Gly145His; Gly145Ile; Gly145Lys; Gly145Leu; Gly145Met; Gly145Asn; Gly145Pro; Gly145Gln; Gly145Arg; Gly145Ser; Gly145Thr; Gly145Val; Gly145Trp; Gly145Tyr; Glu146Ala; Glu146Cys; Glu146Asp; Glu146Phe; Glu146Gly; Glu146His; Glu146Ile; Glu146Lys; Glu146Leu; Glu146Met; Glu146Asn; Glu146Pro; Glu146Gln; Glu146Arg; Glu146Ser; Glu146Thr; Glu146Val; Glu146Trp; Glu146Tyr; Thr147Ala; Thr147Cys; Thr147Asp; Thr147Glu; Thr147Phe; Thr147Gly; Thr147His; Thr147Ile; Thr147Lys; Thr147Leu; Thr147Met; Thr147Asn; Thr147Pro; Thr147Gln; Thr147Arg; Thr147Ser; Thr147Val; Thr147Trp; Thr147Tyr; Gln148Ala; Gln148Cys; Gln148Asp; Gln148Glu; Gln148Phe; Gln148Gly; Gln148His; Gln148Ile; Gln148Lys; Gln148Leu; Gln148Met; Gln148Asn; Gln148Pro; Gln148Arg; Gln148Ser; Gln148Thr; Gln148Val; Gln148Trp; Gln148Tyr; Asp149Ala; Asp149Cys; Asp149Glu; Asp149Phe; Asp149Gly; Asp149His; Asp149Ile; Asp149Lys; Asp149Leu; Asp149Met; Asp149Asn; Asp149Pro; Asp149Gln; Asp149Arg; Asp149Ser; Asp149Thr; Asp149Val; Asp149Trp; Asp149Tyr; Thr150Ala; Thr150Cys; Thr150Asp; Thr150Phe; Thr150Gly; Thr150His; Thr150Ile; Thr150Lys; Thr150Leu; Thr150Met; Thr150Asn; Thr150Pro; Thr150Gln; Thr150Arg; Thr150Ser; Thr150Val; Thr150Trp; Thr150Tyr; Ser151Ala; Ser151Cys; Ser151Asp; Ser151Glu; Ser151Phe; Ser151Gly; Ser151His; Ser151He; Ser151Lys; Ser151Leu; Ser151Met; Ser151Asn; Ser151Pro; Ser151Gln; Ser151Arg; Ser151Thr; Ser151Val; Ser151Trp; Ser151Tyr; Thr152Ala; Thr152Cys; Thr152Asp; Thr152Glu; Thr152Phe; Thr152Gly; Thr152His; Thr152Ile; Thr152Lys; Thr152Leu; Thr152Met; Thr152Asn; Thr152Pro; Thr152Gln; Thr152Arg; Thr152Ser; Thr152Val; Thr152Trp; Thr152Tyr; Ala153Cys; Ala153Asp; Ala153Glu; Ala153Phe; Ala153Gly; Ala153His; Ala153Ile; Ala153Lys; Ala153Leu; Ala153Met; Ala153Asn; Ala153Pro; Ala153Gln; Ala153Arg; Ala153Ser; Ala153Thr; Ala153Val; Ala153Trp; Ala153Tyr; Arg154Ala; Arg154Cys; Arg154Asp; Arg154Glu; Arg154Phe; Arg154Gly; Arg154His; Arg154Ile; Arg154Lys; Arg154Leu; Arg154Met; Arg154Asn; Arg154Pro; Arg154Gln; Arg154Ser; Arg154Thr; Arg154Val; Arg154Trp; Arg154Tyr; Ala155Cys; Ala155Asp; Ala155Glu; Ala155Phe; Ala155Gly; Ala155His; Ala155Ile; Ala155Lys;

Ala155Leu; Ala155Met; Ala155Asn; Ala155Pro; Ala155Gln; Ala155Arg; Ala155Ser; Ala155Thr; Ala155Val; Ala155Trp; Ala155Tyr; Leu156Ala; Leu156Cys; Leu156Asp; Leu156Glu; Leu156Phe; Leu156Gly; Leu156His; Leu156Ile; Leu156Lys; Leu156Met; Leu156Asn; Leu156Pro; Leu156Gln; Leu156Arg; Leu156Ser; Leu156Thr; Leu156Val; Leu156Trp; Leu156Tyr; Val157Ala; Val157Cys; Val157Asp; Val157Glu; Val157Phe; Val157Gly; Val157His; Val157Ile; Val157Lys; Val157Leu; Val157Met; Val157Asn; Val157Pro; Val157Gln; Val157Arg; Val157Ser; Val157Thr; Val157Trp; Val157Tyr; Thr158Ala; Thr158Cys; Thr158Asp; Thr158Glu; Thr158Phe; Thr158Gly; Thr158His; Thr158Ile; Thr158Lys; Thr158Leu; Thr158Met; Thr158Asn; Thr158Pro; Thr158Gln; Thr158Arg; Thr158Ser; Thr158Val; Thr158Trp; Thr158Tyr; Ser159Ala; Ser159Cys; Ser159Asp; Ser159Glu; Ser159Phe; Ser159Gly; Ser159His; Ser159Ile; Ser159Lys; Ser159Leu; Ser159Met; Ser159Asn; Ser159Pro; Ser159Gln; Ser159Arg; Ser159Thr; Ser159Val; Ser159Trp; Ser159Tyr; Leu160Ala; Leu160Cys; Leu160Asp; Leu160Glu; Leu160Phe; Leu160Gly; Leu160His; Leu160Ile; Leu160Lys; Leu160Met; Leu160Asn; Leu160Pro; Leu160Gln; Leu160Arg; Leu160Ser; Leu160Thr; Leu160Val; Leu160Trp; Leu160Tyr; Arg161Ala; Arg161Cys; Arg161Asp; Arg161Glu; Arg161Phe; Arg161Gly; Arg161His; Arg161Ile; Arg161Lys; Arg161Leu; Arg161Met; Arg161Asn; Arg161Pro; Arg161Gln; Arg161Ser; Arg161Thr; Arg161Val; Arg161Trp; Arg161Tyr; Ala162Cys; Ala162Asp; Ala162Glu; Ala162Phe; Ala162Gly; Ala162His; Ala162Ile; Ala162Lys; Ala162Leu; Ala162Met; Ala162Asn; Ala162Pro; Ala162Gln; Ala162Arg; Ala162Ser; Ala162Thr; Ala162Val; Ala162Trp; Ala162Tyr; Phe163Ala; Phe163Cys; Phe163Asp; Phe163Glu; Phe163Gly; Phe163His; Phe163Ile; Phe163Lys; Phe163Leu; Phe163Met; Phe163Asn; Phe163Pro; Phe163Gln; Phe163Arg; Phe163Ser; Phe163Thr; Phe163Val; Phe163Trp; Phe163Tyr; Ala164Cys; Ala164Asp; Ala164Glu; Ala164Phe; Ala164Gly; Ala164His; Ala164Ile; Ala164Lys; Ala164Leu; Ala164Met; Ala164Asn; Ala164Pro; Ala164Gln; Ala164Arg; Ala164Ser; Ala164Thr; Ala164Val; Ala164Trp; Ala164Tyr; Leu165Ala; Leu165Cys; Leu165Asp; Leu165Glu; Leu165Phe; Leu165Gly; Leu165His; Leu165Ile; Leu165Lys; Leu165Met; Leu165Asn; Leu165Pro; Leu165Gln; Leu165Arg; Leu165Ser; Leu165Thr; Leu165Val; Leu165Trp; Leu165Tyr; Glu166Ala; Glu166Cys; Glu166Asp; Glu166Phe; Glu166Gly; Glu166His; Glu166Ile; Glu166Lys; Glu166Leu; Glu166Met; Glu166Asn; Glu166Pro; Glu166Gln; Glu166Arg; Glu166Ser; Glu166Thr; Glu166Val; Glu166Trp; Glu166Tyr; Asp167Ala; Asp167Cys; Asp167Glu; Asp167Phe; Asp167Gly; Asp167His; Asp167Ile; Asp167Lys; Asp167Leu; Asp167Met; Asp167Asn; Asp167Pro; Asp167Gln; Asp167Arg; Asp167Ser; Asp167Thr; Asp167Val; Asp167Trp; Asp167Tyr; Lys168Ala; Lys168Cys; Lys168Asp; Lys168Glu; Lys168Phe; Lys168Gly; Lys168His; Lys168Ile; Lys168Leu; Lys168Met; Lys168Asn; Lys168Pro; Lys168Gln; Lys168Arg; Lys168Ser; Lys168Thr; Lys168Val; Lys168Trp; Lys168Tyr; Leu169Ala; Leu169Cys; Leu169Asp; Leu169Glu; Leu169Phe; Leu169Gly; Leu169His; Leu169Ile; Leu169Lys; Leu169Met; Leu169Asn; Leu169Pro; Leu169Gln; Leu169Arg; Leu169Ser; Leu169Thr; Leu169Val; Leu169Trp; Leu169Tyr; Pro170Ala; Pro170Cys; Pro170Asp; Pro170Glu; Pro170Phe; Pro170Gly; Pro170His; Pro170Ile; Pro170Lys; Pro170Leu; Pro170Met; Pro170Asn; Pro170Gln; Pro170Arg; Pro170Ser; Pro170Thr; Pro170Val; Pro170Trp; Pro170Tyr; Ser171Ala; Ser171Cys; Ser171Asp; Ser171Glu; Ser171Phe; Ser171Gly; Ser171His; Ser171Ile; Ser171Lys; Ser171Leu; Ser171Met; Ser171Asn; Ser171Pro; Ser171Gln; Ser171Arg; Ser171Thr; Ser171Val; Ser171Trp; Ser171Tyr; Glu172Ala; Glu172Cys; Glu172Asp; Glu172Phe; Glu172Gly; Glu172His; Glu172Ile; Glu172Lys; Glu172Leu; Glu172Met; Glu172Asn; Glu172Pro; Glu172Gln; Glu172Arg; Glu172Ser; Glu172Thr; Glu172Val; Glu172Trp; Glu172Tyr; Lys173Ala; Lys173Cys; Lys173Asp; Lys173Glu; Lys173Phe; Lys173Gly; Lys173His; Lys173Ile; Lys173Leu; Lys173Met; Lys173Asn; Lys173Pro; Lys173Gln; Lys173Arg; Lys173Ser; Lys173Thr; Lys173Val; Lys173Trp; Lys173Tyr; Arg174Ala; Arg174Cys; Arg174Asp; Arg174Glu; Arg174Phe; Arg174Gly; Arg174His; Arg174Ile; Arg174Lys; Arg174Leu; Arg174Met; Arg174Asn; Arg174Pro; Arg174Gln; Arg174Ser; Arg174Thr; Arg174Val; Arg174Trp; Arg174Tyr; Glu175Ala; Glu175Cys; Glu175Asp; Glu175Phe; Glu175Gly; Glu175His; Glu175Ile; Glu175Lys; Glu175Leu; Glu175Met; Glu175Asn; Glu175Pro; Glu175Gln; Glu175Arg; Glu175Ser; Glu175Thr; Glu175Val; Glu175Trp; Glu175Tyr; Leu176Ala; Leu176Cys; Leu176Asp; Leu176Glu; Leu176Phe; Leu176Gly; Leu176His; Leu176Ile; Leu176Lys; Leu176Met; Leu176Asn; Leu176Pro; Leu176Gln; Leu176Arg; Leu176Ser; Leu176Thr; Leu176Val; Leu176Trp; Leu176Tyr; Leu177Ala; Leu177Cys; Leu177Asp; Leu177Glu; Leu177Phe; Leu177Gly; Leu177His; Leu177Ile; Leu177Lys; Leu177Met; Leu177Asn; Leu177Pro; Leu177Gln; Leu177Arg; Leu177Ser; Leu177Thr; Leu177Val; Leu177Trp; Leu177Tyr; Ile178Ala; Ile178Cys; Ile178Asp; Ile178Glu; Ile178Phe; Ile178Gly; Ile178His; Ile178Lys; Ile178Leu; Ile178Met; Ile178Asn; Ile178Pro; Ile178Gln; Ile178Arg; Ile178Ser; Ile178Thr; Ile178Val; Ile178Trp; Ile178Tyr; Asp179Ala; Asp179Cys; Asp179Glu; Asp179Phe; Asp179Gly; Asp179His; Asp179Ile; Asp179Lys; Asp179Leu; Asp179Met; Asp179Asn; Asp179Pro; Asp179Gln; Asp179Arg; Asp179Ser; Asp179Thr; Asp179Val; Asp179Trp; Asp179Tyr; Trp180Ala; Trp180Cys; Trp180Asp; Trp180Glu; Trp180Phe; Trp180Gly; Trp180His; Trp180Ile; Trp180Lys; Trp180Leu; Trp180Met; Trp180Asn; Trp180Pro; Trp180Gln; Trp180Arg; Trp180Ser; Trp180Thr; Trp180Val; Trp180Tyr; Met181Ala; Met181Cys; Met181Asp; Met181Glu; Met181Phe; Met181Gly; Met181His; Met181Ile; Met181Lys; Met181Leu; Met181Asn; Met181Pro; Met181Gln; Met181Arg; Met181Ser; Met181Thr; Met181Val; Met181Trp; Met181Tyr; Lys182Ala; Lys182Cys; Lys182Asp; Lys182Glu; Lys182Phe; Lys182Gly; Lys182His; Lys182Ile; Lys182Leu; Lys182Met; Lys182Asn; Lys182Pro; Lys182Gln; Lys182Arg; Lys182Ser; Lys182Thr; Lys182Val; Lys182Trp; Lys182Tyr; Arg183Ala; Arg183Cys; Arg183Asp; Arg183Glu; Arg183Phe; Arg183Gly; Arg183His; Arg183Ile; Arg183Lys; Arg183Leu; Arg183Met; Arg183Asn; Arg183Pro; Arg183Gln; Arg183Ser; Arg183Thr; Arg183Val; Arg183Trp; Arg183Tyr; Asn184Ala; Asn184Cys; Asn184Asp; Asn184Glu; Asn184Phe; Asn184Gly; Asn184His; Asn184Ile; Asn184Lys; Asn184Leu; Asn184Met; Asn184Pro; Asn184Gln; Asn184Arg; Asn184Ser; Asn184Thr; Asn184Val; Asn184Trp; Asn184Tyr; Thr185Ala; Thr185Cys; Thr185Asp;

Thr185Glu; Thr185Phe; Thr185Gly; Thr185His; Thr185Ile; Thr185Lys; Thr185Leu; Thr185Met; Thr185Asn; Thr185Pro; Thr185Gln; Thr185Arg; Thr185Ser; Thr185Val; Thr185Trp; Thr185Tyr; Thr186Ala; Thr186Cys; Thr186Asp; Thr186Glu; Thr186Phe; Thr186Gly; Thr186His; Thr186Ile; Thr186Lys; Thr186Leu; Thr186Met; Thr186Asn; Thr186Pro; Thr186Gln; Thr186Arg; Thr186Ser; Thr186Val; Thr186Trp; Thr186Tyr; Gly187Ala; Gly187Cys; Gly187Asp; Gly187Glu; Gly187Phe; Gly187His; Gly187Ile; Gly187Lys; Gly187Leu; Gly187Met; Gly187Asn; Gly187Pro; Gly187Gln; Gly187Arg; Gly187Ser; Gly187Thr; Gly187Val; Gly187Trp; Gly187Tyr; Asp188Ala; Asp188Cys; Asp188Glu; Asp188Phe; Asp188Gly; Asp188His; Asp188Ile; Asp188Lys; Asp188Leu; Asp188Met; Asp188Asn; Asp188Pro; Asp188Gln; Asp188Arg; Asp188Ser; Asp188Thr; Asp188Val; Asp188Trp; Asp188Tyr; Ala189Cys; Ala189Asp; Ala189Glu; Ala189Phe; Ala189Gly; Ala189His; Ala189Ile; Ala189Lys; Ala189Leu; Ala189Met; Ala189Asn; Ala189Pro; Ala189Gln; Ala189Arg; Ala189Ser; Ala189Thr; Ala189Val; Ala189Trp; Ala189Tyr; Leu190Ala; Leu190Cys; Leu190Asp; Leu190Glu; Leu190Phe; Leu190Gly; Leu190His; Leu190Ile; Leu190Lys; Leu190Met; Leu190Asn; Leu190Pro; Leu190Gln; Leu190Arg; Leu190Ser; Leu190Thr; Leu190Val; Leu190Trp; Leu190Tyr; Ile191Ala; Ile191Cys; Ile191Asp; Ile191Glu; Ile191Phe; Ile191Gly; Ile191His; Ile191Lys; Ile191Leu; Ile191Met; Ile191Asn; Ile191Pro; Ile191Gln; Ile191Arg; Ile191Ser; Ile191Thr; Ile191Val; Ile191Trp; Ile191Tyr; Arg192Ala; Arg192Cys; Arg192Asp; Arg192Glu; Arg192Phe; Arg192Gly; Arg192His; Arg192Ile; Arg192Lys; Arg192Leu; Arg192Met; Arg192Asn; Arg192Pro; Arg192Gln; Arg192Ser; Arg192Thr; Arg192Val; Arg192Trp; Arg192Tyr; Ala193Cys; Ala193Asp; Ala193Glu; Ala193Phe; Ala193Gly; Ala193His; Ala193Ile; Ala193Lys; Ala193Leu; Ala193Met; Ala193Asn; Ala193Pro; Ala193Gln; Ala193Arg; Ala193Ser; Ala193Thr; Ala193Val; Ala193Trp; Ala193Tyr; Gly194Ala; Gly194Cys; Gly194Asp; Gly194Glu; Gly194Phe; Gly194His; Gly194Ile; Gly194Lys; Gly194Leu; Gly194Met; Gly194Asn; Gly194Pro; Gly194Gln; Gly194Arg; Gly194Ser; Gly194Thr; Gly194Val; Gly194Trp; Gly194Tyr;Val195Ala; Val195Cys; Val195Asp; Val195Glu; Val195Phe; Val195Gly; Val195His; Val195Ile; Val195Lys; Val195Leu; Val195Met; Val195Asn; Val195Pro; Val195Gln; Val195Arg; Val195Ser; Val195Thr; Val195Trp; Val195Tyr; Pro196Ala; Pro196Cys; Pro196Asp; Pro196Glu; Pro196Phe; Pro196Gly; Pro196His; Pro196Ile; Pro196Lys; Pro196Leu; Pro196Met; Pro196Asn; Pro196Gln; Pro196Arg; Pro196Ser; Pro196Thr; Pro196Val; Pro196Trp; Pro196Tyr; Asp197Ala; Asp197Cys; Asp197Glu; Asp197Phe; Asp197Gly; Asp197His; Asp197Ile; Asp197Lys; Asp197Leu; Asp197Met; Asp197Asn; Asp197Pro; Asp197Gln; Asp197Arg; Asp197Ser; Asp197Thr; Asp197Val; Asp197Trp; Asp197Tyr; Gly198Ala; Gly198Cys; Gly198Asp; Gly198Glu; Gly198Phe; Gly198His; Gly198Ile; Gly198Lys; Gly198Leu; Gly198Met; Gly198Asn; Gly198Pro; Gly198Gln; Gly198Arg; Gly198Ser; Gly198Thr; Gly198Val; Gly198Trp; Gly198Tyr; Trp199Ala; Trp199Cys; Trp199Asp; Trp199Glu; Trp199Phe; Trp199Gly; Trp199His; Trp199Ile; Trp199Lys; Trp199Leu; Trp199Met; Trp199Asn; Trp199Pro; Trp199Gln; Trp199Arg; Trp199Ser; Trp199Thr; Trp199Val; Trp199Tyr; Glu200Ala; Glu200Cys; Glu200Asp; Glu200Phe; Glu200Gly; Glu200His; Glu200Ile; Glu200Lys; Glu200Leu; Glu200Met; Glu200Asn; Glu200Pro; Glu200Gln; Glu200Arg; Glu200Ser; Glu200Thr; Glu200Val; Glu200Trp; Glu200Tyr; Val201Ala; Val201Cys; Val201Asp; Val201Glu; Val201Phe; Val201Gly; Val201His; Val201Ile; Val201Lys; Val201Leu; Val201Met; Val201Asn; Val201Pro; Val201Gln; Val201Arg; Val201Ser; Val201Thr; Val201Trp; Val201Tyr; Ala202Cys; Ala202Asp; Ala202Glu; Ala202Phe; Ala202Gly; Ala202His; Ala202Ile; Ala202Lys; Ala202Leu; Ala202Met; Ala202Asn; Ala202Pro; Ala202Gln; Ala202Arg; Ala202Ser; Ala202Thr; Ala202Val; Ala202Trp; Ala202Tyr; Asp203Ala; Asp203Cys; Asp203Glu; Asp203Phe; Asp203Gly; Asp203His; Asp203Ile; Asp203Lys; Asp203Leu; Asp203Met; Asp203Asn; Asp203Pro; Asp203Gln; Asp203Arg; Asp203Ser; Asp203Thr; Asp203Val; Asp203Trp; Asp203Tyr; Lys204Ala; Lys204Cys; Lys204Asp; Lys204Glu; Lys204Phe; Lys204Gly; Lys204His; Lys204Ile; Lys204Leu; Lys204Met; Lys204Asn; Lys204Pro; Lys204Gln; Lys204Arg; Lys204Ser; Lys204Thr; Lys204Val; Lys204Trp; Lys204Tyr; Thr205Ala; Thr205Cys; Thr205Asp; Thr205Glu; Thr205Phe; Thr205Gly; Thr205His; Thr205Ile; Thr205Lys; Thr205Leu; Thr205Met; Thr205Asn; Thr205Pro; Thr205Gln; Thr205Arg; Thr205Ser; Thr205Val; Thr205Trp; Thr205Tyr; Gly206Ala; Gly206Cys; Gly206Asp; Gly206Glu; Gly206Phe; Gly206His; Gly206Ile; Gly206Lys; Gly206Leu; Gly206Met; Gly206Asn; Gly206Pro; Gly206Gln; Gly206Arg; Gly206Ser; Gly206Thr; Gly206Val; Gly206Trp; Gly206Tyr; Ala207Cys; Ala207Asp; Ala207Glu; Ala207Phe; Ala207Gly; Ala207His; Ala207Ile; Ala207Lys; Ala207Leu; Ala207Met; Ala207Asn; Ala207Pro; Ala207Gln; Ala207Arg; Ala207Ser; Ala207Thr; Ala207Val; Ala207Trp; Ala207Tyr; Ala208Cys; Ala208Asp; Ala208Glu; Ala208Phe; Ala208Gly; Ala208His; Ala208Ile; Ala208Lys; Ala208Leu; Ala208Met; Ala208Asn; Ala208Pro; Ala208Gln; Ala208Arg; Ala208Ser; Ala208Thr; Ala208Val; Ala208Trp; Ala208Tyr; Ser209Ala; Ser209Cys; Ser209Asp; Ser209Glu; Ser209Phe; Ser209Gly; Ser209His; Ser209Ile; Ser209Lys; Ser209Leu; Ser209Met; Ser209Asn; Ser209Pro; Ser209Gln; Ser209Arg; Ser209Thr; Ser209Val; Ser209Trp; Ser209Tyr; Tyr210Ala; Tyr210Cys; Tyr210Asp; Tyr210Glu; Tyr210Phe; Tyr210Gly; Tyr210His; Tyr210Ile; Tyr210Lys; Tyr210Leu; Tyr210Met; Tyr210Asn; Tyr210Pro; Tyr210Gln; Tyr210Arg; Tyr210Ser; Tyr210Thr; Tyr210Val; Tyr210Trp; Gly211Ala; Gly211Cys; Gly211Asp; Gly211Glu; Gly211Phe; Gly211His; Gly211Ile; Gly211Lys; Gly211Leu; Gly211Met; Gly211Asn; Gly211Pro; Gly211Gln; Gly211Arg; Gly211Ser; Gly211Thr; Gly211Val; Gly211Trp; Gly211Tyr; Thr212Ala; Thr212Cys; Thr212Asp; Thr212Glu; Thr212Phe; Thr212Gly; Thr212His; Thr212Ile; Thr212Lys; Thr212Leu; Thr212Met; Thr212Asn; Thr212Pro; Thr212Gln; Thr212Arg; Thr212Ser; Thr212Val; Thr212Trp; Thr212Tyr; Arg213Ala; Arg213Cys; Arg213Asp; Arg213Glu; Arg213Phe; Arg213Gly; Arg213His; Arg213Ile; Arg213Lys; Arg213Leu; Arg213Met; Arg213Asn; Arg213Pro; Arg213Gln; Arg213Ser; Arg213Thr; Arg213Val; Arg213Trp; Arg213Tyr; Asn214Ala; Asn214Cys; Asn214Asp; Asn214Glu; Asn214Phe; Asn214Gly; Asn214His; Asn214Ile; Asn214Lys; Asn214Leu; Asn214Met; Asn214Pro; Asn214Gln; Asn214Arg; Asn214Ser; Asn214Thr; Asn214Val; Asn214Trp; Asn214Tyr; Asp215Ala; Asp215Cys; Asp215Glu; Asp215Phe; Asp215Gly; Asp215His; Asp215Ile; Asp215Lys; Asp215Leu; Asp215Met; Asp215Asn; Asp215Pro; Asp215Gln;

Asp215Arg; Asp215Ser; Asp215Thr; Asp215Val; Asp215Trp; Asp215Tyr; Ile216Ala; Ile216Cys; Ile216Asp; Ile216Glu; Ile216Phe; Ile216Gly; Ile216His; Ile216Lys; Ile216Leu; Ile216Met; Ile216Asn; Ile216Pro; Ile216Gln; Ile216Arg; Ile216Ser; Ile216Thr; Ile216Val; Ile216Trp; Ile216Tyr; Ala217Cys; Ala217Asp; Ala217Glu; Ala217Phe; Ala217Gly; Ala217His; Ala217Ile; Ala217Lys; Ala217Leu; Ala217Met; Ala217Asn; Ala217Pro; Ala217Gln; Ala217Arg; Ala217Ser; Ala217Thr; Ala217Val; Ala217Trp; Ala217Tyr; Ile218Ala; Ile218Cys; Ile218Asp; Ile218Glu; Ile218Phe; Ile218Gly; Ile218His; Ile218Lys; Ile218Leu; Ile218Met; Ile218Asn; Ile218Pro; Ile218Gln; Ile218Arg; Ile218Ser; Ile218Thr; Ile218Val; Ile218Trp; Ile218Tyr; Ile219Ala; Ile219Cys; Ile219Asp; Ile219Glu; Ile219Phe; Ile219Gly; Ile219His; Ile219Lys; Ile219Leu; Ile219Met; Ile219Asn; Ile219Pro; Ile219Gln; Ile219Arg; Ile219Ser; Ile219Thr; Ile219Val; Ile219Trp; Ile219Tyr; Trp220Ala; Trp220Cys; Trp220Asp; Trp220Glu; Trp220Phe; Trp220Gly; Trp220His; Trp220Ile; Trp220Lys; Trp220Leu; Trp220Met; Trp220Asn; Trp220Pro; Trp220Gln; Trp220Arg; Trp220Ser; Trp220Thr; Trp220Val; Trp220Tyr; Pro221Ala; Pro221Cys; Pro221Asp; Pro221Glu; Pro221Phe; Pro221Gly; Pro221His; Pro221Ile; Pro221Lys; Pro221Leu; Pro221Met; Pro221Asn; Pro221Gln; Pro221Arg; Pro221Ser; Pro221Thr; Pro221Val; Pro221Trp; Pro221Tyr; Pro222Ala; Pro222Cys; Pro222Asp; Pro222Glu; Pro222Phe; Pro222Gly; Pro222His; Pro222Ile; Pro222Lys; Pro222Leu; Pro222Met; Pro222Asn; Pro222Gln; Pro222Arg; Pro222Ser; Pro222Thr; Pro222Val; Pro222Trp; Pro222Tyr; Lys223Ala; Lys223Cys; Lys223Asp; Lys223Glu; Lys223Phe; Lys223Gly; Lys223His; Lys223Ile; Lys223Leu; Lys223Met; Lys223Asn; Lys223Pro; Lys223Gln; Lys223Arg; Lys223Ser; Lys223Thr; Lys223Val; Lys223Trp; Lys223Tyr; Gly224Ala; Gly224Cys; Gly224Asp; Gly224Glu; Gly224Phe; Gly224His; Gly224Ile; Gly224Lys; Gly224Leu; Gly224Met; Gly224Asn; Gly224Pro; Gly224Gln; Gly224Arg; Gly224Ser; Gly224Thr; Gly224Val; Gly224Trp; Gly224Tyr; Asp225Ala; Asp225Cys; Asp225Glu; Asp225Phe; Asp225Gly; Asp225His; Asp225Ile; Asp225Lys; Asp225Leu; Asp225Met; Asp225Asn; Asp225Pro; Asp225Gln; Asp225Arg; Asp225Ser; Asp225Thr; Asp225Val; Asp225Trp; Asp225Tyr; Pro226Ala; Pro226Cys; Pro226Asp; Pro226Glu; Pro226Phe; Pro226Gly; Pro226His; Pro226Ile; Pro226Lys; Pro226Leu; Pro226Met; Pro226Asn; Pro226Gln; Pro226Arg; Pro226Ser; Pro226Thr; Pro226Val; Pro226Trp; Pro226Tyr; Val227Ala; Val227Cys; Val227Asp; Val227Glu; Val227Phe; Val227Gly; Val227His; Val227Ile; Val227Lys; Val227Leu; Val227Met; Val227Asn; Val227Pro; Val227Gln; Val227Arg; Val227Ser; Val227Thr; Val227Trp; Val227Tyr; Val228Ala; Val228Cys; Val228Asp; Val228Glu; Val228Phe; Val228Gly; Val228His; Val228Ile; Val228Lys; Val228Leu; Val228Met; Val228Asn; Val228Pro; Val228Gln; Val228Arg; Val228Ser; Val228Thr; Val228Trp; Val228Tyr; Leu229Ala; Leu229Cys; Leu229Asp; Leu229Glu; Leu229Phe; Leu229Gly; Leu229His; Leu229Ile; Leu229Lys; Leu229Met; Leu229Asn; Leu229Pro; Leu229Gln; Leu229Arg; Leu229Ser; Leu229Thr; Leu229Val; Leu229Trp; Leu229Tyr; Ala230Cys; Ala230Asp; Ala230Glu; Ala230Phe; Ala230Gly; Ala230His; Ala230Ile; Ala230Lys; Ala230Leu; Ala230Met; Ala230Asn; Ala230Pro; Ala230Gln; Ala230Arg; Ala230Ser; Ala230Thr; Ala230Val; Ala230Trp; Ala230Tyr; Val231Ala; Val231Cys; Val231Asp; Val231Glu; Val231Phe; Val231Gly; Val231His; Val231Ile; Val231Lys; Val231Leu; Val231Met; Val231Asn; Val231Pro; Val231Gln; Val231Arg; Val231Ser; Val231Thr; Val231Trp; Val231Tyr; Leu232Ala; Leu232Cys; Leu232Asp; Leu232Glu; Leu232Phe; Leu232Gly; Leu232His; Leu232Ile; Leu232Lys; Leu232Met; Leu232Asn; Leu232Pro; Leu232Gln; Leu232Arg; Leu232Ser; Leu232Thr; Leu232Val; Leu232Trp; Leu232Tyr; Ser233Ala; Ser233Cys; Ser233Asp; Ser233Glu; Ser233Phe; Ser233Gly; Ser233His; Ser233Ile; Ser233Lys; Ser233Leu; Ser233Met; Ser233Asn; Ser233Pro; Ser233Gln; Ser233Arg; Ser233Thr; Ser233Val; Ser233Trp; Ser233Tyr; Ser234Ala; Ser234Cys; Ser234Asp; Ser234Glu; Ser234Phe; Ser234Gly; Ser234His; Ser234Ile; Ser234Lys; Ser234Leu; Ser234Met; Ser234Asn; Ser234Pro; Ser234Gln; Ser234Arg; Ser234Thr; Ser234Val; Ser234Trp; Ser234Tyr; Arg235Ala; Arg235Cys; Arg235Asp; Arg235Glu; Arg235Phe; Arg235Gly; Arg235His; Arg235Ile; Arg235Lys; Arg235Leu; Arg235Met; Arg235Asn; Arg235Pro; Arg235Gln; Arg235Ser; Arg235Thr; Arg235Val; Arg235Trp; Arg235Tyr; Asp236Ala; Asp236Cys; Asp236Glu; Asp236Phe; Asp236Gly; Asp236His; Asp236Ile; Asp236Lys; Asp236Leu; Asp236Met; Asp236Asn; Asp236Pro; Asp236Gln; Asp236Arg; Asp236Ser; Asp236Thr; Asp236Val; Asp236Trp; Asp236Tyr; Lys237Ala; Lys237Cys; Lys237Asp; Lys237Glu; Lys237Phe; Lys237Gly; Lys237His; Lys237Ile; Lys237Leu; Lys237Met; Lys237Asn; Lys237Pro; Lys237Gln; Lys237Arg; Lys237Ser; Lys237Thr; Lys237Val; Lys237Trp; Lys237Tyr; Lys238Ala; Lys238Cys; Lys238Asp; Lys238Glu; Lys238Phe; Lys238Gly; Lys238His; Lys238Ile; Lys238Leu; Lys238Met; Lys238Asn; Lys238Pro; Lys238Gln; Lys238Arg; Lys238Ser; Lys238Thr; Lys238Val; Lys238Trp; Lys238Tyr; Asp239Ala; Asp239Cys; Asp239Glu; Asp239Phe; Asp239Gly; Asp239His; Asp239Ile; Asp239Lys; Asp239Leu; Asp239Met; Asp239Asn; Asp239Pro; Asp239Gln; Asp239Arg; Asp239Ser; Asp239Thr; Asp239Val; Asp239Trp; Asp239Tyr; Ala240Cys; Ala240Asp; Ala240Glu; Ala240Phe; Ala240Gly; Ala240His; Ala240Ile; Ala240Lys; Ala240Leu; Ala240Met; Ala240Asn; Ala240Pro; Ala240Gln; Ala240Arg; Ala240Ser; Ala240Thr; Ala240Val; Ala240Trp; Ala240Tyr; Lys241Ala; Lys241Cys; Lys241Asp; Lys241Glu; Lys241Phe; Lys241Gly; Lys241His; Lys241Ile; Lys241Leu; Lys241Met; Lys241Asn; Lys241Pro; Lys241Gln; Lys241Arg; Lys241Ser; Lys241Thr; Lys241Val; Lys241Trp; Lys241Tyr; Tyr242Ala; Tyr242Cys; Tyr242Asp; Tyr242Glu; Tyr242Phe; Tyr242Gly; Tyr242His; Tyr242Ile; Tyr242Lys; Tyr242Leu; Tyr242Met; Tyr242Asn; Tyr242Pro; Tyr242Gln; Tyr242Arg; Tyr242Ser; Tyr242Thr; Tyr242Val; Tyr242Trp; Asp243Ala; Asp243Cys; Asp243Glu; Asp243Phe; Asp243Gly; Asp243His; Asp243Ile; Asp243Lys; Asp243Leu; Asp243Met; Asp243Asn; Asp243Pro; Asp243Gln; Asp243Arg; Asp243Ser; Asp243Thr; Asp243Val; Asp243Trp; Asp243Tyr; Asp244Ala; Asp244Cys; Asp244Glu; Asp244Phe; Asp244Gly; Asp244His; Asp244Ile; Asp244Lys; Asp244Leu; Asp244Met; Asp244Asn; Asp244Pro; Asp244Gln; Asp244Arg; Asp244Ser; Asp244Thr; Asp244Val; Asp244Trp; Asp244Tyr; Lys245Ala; Lys245Cys; Lys245Asp; Lys245Glu; Lys245Phe; Lys245Gly; Lys245His; Lys245Ile; Lys245Leu; Lys245Met; Lys245Asn; Lys245Pro; Lys245Gln; Lys245Arg; Lys245Ser; Lys245Thr; Lys245Val; Lys245Trp; Lys245Tyr; Leu246Ala; Leu246Cys; Leu246Asp; Leu246Glu; Leu246Phe; Leu246Gly; Leu246His; Leu246Ile; Leu246Lys; Leu246Met; Leu246Asn; Leu246Pro; Leu246Gln; Leu246Arg; Leu246Ser;

Leu246Thr; Leu246Val; Leu246Trp; Leu246Tyr; Ile247Ala; Ile247Cys; Ile247Asp; Ile247Glu; Ile247Phe; Ile247Gly; Ile247His; Ile247Lys; Ile247Leu; Ile247Met; Ile247Asn; Ile247Pro; Ile247Gln; Ile247Arg; Ile247Ser; Ile247Thr; Ile247Val; Ile247Trp; Ile247Tyr; Ala248Cys; Ala248Asp; Ala248Glu; Ala248Phe; Ala248Gly; Ala248His; Ala248Ile; Ala248Lys; Ala248Leu; Ala248Met; Ala248Asn; Ala248Pro; Ala248Gln; Ala248Arg; Ala248Ser; Ala248Thr; Ala248Val; Ala248Trp; Ala248Tyr; Glu249Ala; Glu249Cys; Glu249Asp; Glu249Phe; Glu249Gly; Glu249His; Glu249Ile; Glu249Lys; Glu249Leu; Glu249Met; Glu249Asn; Glu249Pro; Glu249Gln; Glu249Arg; Glu249Ser; Glu249Thr; Glu249Val; Glu249Trp; Glu249Tyr; Ala250Cys; Ala250Asp; Ala250Glu; Ala250Phe; Ala250Gly; Ala250His; Ala250Ile; Ala250Lys; Ala250Leu; Ala250Met; Ala250Asn; Ala250Pro; Ala250Gln; Ala250Arg; Ala250Ser; Ala250Thr; Ala250Val; Ala250Trp; Ala250Tyr; Thr251Ala; Thr251Cys; Thr251Asp; Thr251Glu; Thr251Phe; Thr251Gly; Thr251His; Thr251Ile; Thr251Lys; Thr251Leu; Thr251Met; Thr251Asn; Thr251Pro; Thr251Gln; Thr251Arg; Thr251Ser; Thr251Val; Thr251Trp; Thr251Tyr; Lys252Ala; Lys252Cys; Lys252Asp; Lys252Glu; Lys252Phe; Lys252Gly; Lys252His; Lys252Ile; Lys252Leu; Lys252Met; Lys252Asn; Lys252Pro; Lys252Gln; Lys252Arg; Lys252Ser; Lys252Thr; Lys252Val; Lys252Trp; Lys252Tyr; Val253Ala; Val253Cys; Val253Asp; Val253Glu; Val253Phe; Val253Gly; Val253His; Val253Ile; Val253Lys; Val253Leu; Val253Met; Val253Asn; Val253Pro; Val253Gln; Val253Arg; Val253Ser; Val253Thr; Val253Trp; Val253Tyr; Val254Ala; Val254Cys; Val254Asp; Val254Glu; Val254Phe; Val254Gly; Val254His; Val254Ile; Val254Lys; Val254Leu; Val254Met; Val254Asn; Val254Pro; Val254Gln; Val254Arg; Val254Ser; Val254Thr; Val254Trp; Val254Tyr; Met255Ala; Met255Cys; Met255Asp; Met255Glu; Met255Phe; Met255Gly; Met255His; Met255Ile; Met255Lys; Met255Leu; Met255Asn; Met255Pro; Met255Gln; Met255Arg; Met255Ser; Met255Thr; Met255Val; Met255Trp; Met255Tyr; Lys256Ala; Lys256Cys; Lys256Asp; Lys256Glu; Lys256Phe; Lys256Gly; Lys256His; Lys256Ile; Lys256Leu; Lys256Met; Lys256Asn; Lys256Pro; Lys256Gln; Lys256Arg; Lys256Ser; Lys256Thr; Lys256Val; Lys256Trp; Lys256Tyr; Ala257Cys; Ala257Asp; Ala257Glu; Ala257Phe; Ala257Gly; Ala257His; Ala257Ile; Ala257Lys; Ala257Leu; Ala257Met; Ala257Asn; Ala257Pro; Ala257Gln; Ala257Arg; Ala257Ser; Ala257Thr; Ala257Val; Ala257Trp; Ala257Tyr; Leu258Ala; Leu258Cys; Leu258Asp; Leu258Glu; Leu258Phe; Leu258Gly; Leu258His; Leu258Ile; Leu258Lys; Leu258Met; Leu258Asn; Leu258Pro; Leu258Gln; Leu258Arg; Leu258Ser; Leu258Thr; Leu258Val; Leu258Trp; Leu258Tyr; Asn259Ala; Asn259Cys; Asn259Asp; Asn259Glu; Asn259Phe; Asn259Gly; Asn259His; Asn259Ile; Asn259Lys; Asn259Leu; Asn259Met; Asn259Pro; Asn259Gln; Asn259Arg; Asn259Ser; Asn259Thr; Asn259Val; Asn259Trp; Asn259Tyr; Met260Ala; Met260Cys; Met260Asp; Met260Glu; Met260Phe; Met260Gly; Met260His; Met260Ile; Met260Lys; Met260Leu; Met260Asn; Met260Pro; Met260Gln; Met260Arg; Met260Ser; Met260Thr; Met260Val; Met260Trp; Met260Tyr; Asn261Ala; Asn261Cys; Asn261Asp; Asn261Glu; Asn261Phe; Asn261Gly; Asn261His; Asn261Ile; Asn261Lys; Asn261Leu; Asn261Met; Asn261Pro; Asn261Gln; Asn261Arg; Asn261Ser; Asn261Thr; Asn261Val; Asn261Trp; Asn261Tyr; Gly262Ala; Gly262Cys; Gly262Asp; Gly262Glu; Gly262Phe; Gly262His; Gly262Ile; Gly262Lys; Gly262Leu; Gly262Met; Gly262Asn; Gly262Pro; Gly262Gln; Gly262Arg; Gly262Ser; Gly262Thr; Gly262Val; Gly262Trp; Gly262Tyr; Lys263Ala; Lys263Cys; Lys263Asp; Lys263Glu; Lys263Phe; Lys263Gly; Lys263His; Lys263Ile; Lys263Leu; Lys263Met; Lys263Asn; Lys263Pro; Lys263Gln; Lys263Arg; Lys263Ser; Lys263Thr; Lys263Val; Lys263Trp; Lys263Tyr; Met 264Ala; Met 264Cys; Met 264Asp; Met 264Glu; Met 264Phe; Met 264Gly; Met 264His; Met 264Ile; Met 264Lys; Met 264Leu; Met 264Asn; Met 264Pro; Met 264Gln; Met 264Arg; Met 264Ser; Met 264Thr; Met 264Val; Met 264Trp; Met 264Tyr; Asn 265Ala; Asn 265Cys; Asn 265Asp; Asn 265Glu; Asn 265Phe; Asn 265Gly; Asn 265His; Asn 265Ile; Asn 265Lys; Asn 265Leu; Asn 265Met; Asn 265Pro; Asn 265Gln; Asn 265Arg; Asn 265Ser; Asn 265Thr; Asn 265Val; Asn 265Trp; Asn 265Tyr; Gly 266Ala; Gly 266Cys; Gly 266Asp; Gly 266Glu; Gly 266Phe; Gly 266His; Gly 266Ile; Gly 266Lys; Gly 266Leu; Gly 266Met; Gly 266Asn; Gly 266Pro; Gly 266Gln; Gly 266Arg; Gly 266Ser; Gly 266Thr; Gly 266Val; Gly 266Trp; Gly 266Tyr; Lys267Ala; Lys267Cys; Lys267Asp; Lys267Glu; Lys267Phe; Lys267Gly; Lys267His; Lys267Ile; Lys267Leu; Lys267Met; Lys267Asn; Lys267Pro; Lys267Gln; Lys267Arg; Lys267Ser; Lys267Thr; Lys267Val; Lys267Trp; and Lys267Tyr. In some embodiments, SEQ ID NO: 1 may have a Met and/or Thr preceeding the first residue of the sequence. These residues may be similarly mutated as above.

In all of these mutants, the numbering of residues corresponds to SEQ ID NO: 1. These residue numbers may be converted to Ambler numbers (Ambler et al., 1991, A standard numbering scheme for the Class A β-lactamases, *Biochem. J.* 276:269-272, the contents of which are hereby incorporated by reference) through use of any conventional bioinformatic method, for example by using BLAST (Basic Local Alignment Search Tools) or FASTA (FAST-All). For example, residue 244 corresponds to Ambler 276. For example, the following conversions may be used:

| Ambler Classification No. | SEQ ID NO: 1 Residue |
| --- | --- |
| F33 | F6 |
| I72 | I44 |
| Q135 | Q105 |
| G156 | G126 |
| T160 | T130 |
| A232 | A202 |
| A237 | A207 |
| A238 | A208 |
| S240 | S209 |
| T243 | T212 |
| R244 | R213 |
| S266 | S234 |
| D276 | D244 |

Furthermore, percent identity may also be assessed with these conventional bioinformatic methods.

In one aspect, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1 or SEQ ID NO: 3 and one or more of the following mutations of Ambler classification: F33X, Q135X, G156X, A232X, A237X, A238X, S240X, T243X, R244X, S266X, and D276X, wherein X is any naturally-occurring amino acid. In some embodiments, X is a naturally occurring hydrophilic or hydrophobic amino acid residue or a non-classical amino acid.

In another aspect, the beta-lactamase polypeptide produced by methods of the invention comprises an amino acid sequence having at least 60% sequence identity with SEQ ID NO: 1 or SEQ ID NO: 3 and one or more of the following mutations of Ambler classification: a hydrophobic residue other than phenylalanine (F) at position 33; a hydrophobic residue other than glutamine (Q) at position 135; a hydrophilic residue other than glycine (G) at position 156; a hydrophobic residue other than alanine (A) at position 232; a hydrophilic residue other than alanine (A) at position 237; a hydrophobic or hydrophilic residue other than alanine (A) at position 238; a hydrophilic residue other than serine (S) at position 240; a hydrophobic residue other than threonine (T) at position 243; a hydrophobic residue other than arginine (R) at position 244; a hydrophilic residue other than serine (S) at position 266; and a hydrophilic residue other than aspartate (D) at position 276.

As used throughout, a hydrophilic amino acid residue may include a polar and positively charged hydrophilic residue selected from arginine (R) and lysine (K), a polar and neutral of charge hydrophilic residue selected from asparagine (N), glutamine (Q), serine (S), threonine (T), proline (P), and cysteine (C), a polar and negatively charged hydrophilic residue selected from aspartate (D) and glutamate (E), or an aromatic, polar and positively charged hydrophilic including histidine (H). As used throughout, a hydrophobic amino acid residue may include a hydrophobic, aliphatic amino acid selected from glycine (G), alanine (A), leucine (L), isoleucine (I), methionine (M), or valine (V) or a hydrophobic, aromatic amino acid selected from phenylalanine (F), tryptophan (W), or tyrosine (Y).

Mutations may be made to the gene sequence of a beta-lactamase (e.g. SEQ ID NOs: 2 and 4) by reference to the genetic code, including taking into account codon degeneracy.

In some embodiments, the beta-lactamase polypeptide produced by methods of the invention comprises one or more of the following mutations at positions of Ambler classification: F33Y, Q135M, G156R, A232G, A237S, A238G or T, S240P or D, T243I, R244T, S266N, D276N or R or K. In one embodiment, the beta-lactamases and/or pharmaceutical compositions comprise Q135M. In another embodiment, the beta-lactamases and/or pharmaceutical compositions comprise G156R and A238T. In another embodiment, the beta-lactamases and/or pharmaceutical compositions comprise F33Y and D276N. In still another embodiment, the beta-lactamases and/or pharmaceutical compositions comprise F33Y, S240P, and D276N. In one embodiment, the beta-lactamases and/or pharmaceutical compositions comprise F33Y, A238T, and D276N. In another embodiment, the beta-lactamases and/or pharmaceutical compositions comprise A232G, A237S, A238G, and S240D. In a further embodiment, the beta-lactamases and/or pharmaceutical compositions comprise A232G, A237S, A238G, S240D, and R244T. In another embodiment, the beta-lactamases and/or pharmaceutical compositions comprise A232G, A237S, A238G, S240D, and D276R. In one embodiment, the beta-lactamases and/or pharmaceutical compositions comprise A232G, A237S, A238G, S240D, and D276K. In one embodiment, the beta-lactamases and/or pharmaceutical compositions comprise A232G, A237S, A238G, S240D, and Q135M. In one embodiment, the beta-lactamases and/or pharmaceutical compositions comprise A238T. In one embodiment, the beta-lactamases and/or pharmaceutical compositions comprise T243I, S266N, and D276N. In one embodiment, the beta-lactamases and/or pharmaceutical compositions comprise A232G, A237S, A238G, S240D, and D276N.

In various embodiments, the beta-lactamase polypeptide produced by methods of the invention comprises one or more of the following mutations:

| Mutations relative to P1A (based on the Ambler classification) | Name |
| --- | --- |
| Wild type | RS310 (or P1A) |
| D276N | IS118 (or P3A) |
| I72S | IS222 |
| T160F | IS203 |
| R244T | IS217 |
| R244T D276K | IS215 |
| Q135M | IS197 |
| G156R A238T | IS235 |
| F33Y D276N | IS158 |
| F33Y S240P D276N | IS230 (or IS181) |
| F33Y A238T D276N | IS232 (or IS180) |
| I72S Q135M T160F (Block 1 mutants) | IS227 |
| A232G A237S A238G S240D (Block 2 mutants) | IS191 |
| A232G A237S A238G S240D R244T | IS229 |
| A232G A237S A238G S240D D276R | IS219 |
| A232G A237S A238G S240D D276K | IS221 |
| A232G A237S A238G S240D Q135M | IS224 |
| A238T | IS233 |
| T243I S266N D276N | IS234 (or IS176) |
| A232G A237S A238G S240D D276N | IS288 (or P4A) |

In various embodiments, the beta-lactamases and/or pharmaceutical compositions comprise an amino acid sequence having at least 60% sequence identity with one or more of the mutants provided in the table directly above.

In illustrative embodiments, the beta-lactamases and/or pharmaceutical compositions comprise an amino acid sequence having at least 60% sequence identity with SEQ ID NO: 1 or SEQ ID NO: 3 and the following of Ambler classification: a residue other than aspartate (D) at position 276.

In illustrative embodiments, the beta-lactamases and/or pharmaceutical compositions comprise an amino acid sequence having at least 90%, or 95%, or 97%, or 99% sequence identity with SEQ ID NO: 1 and a hydrophilic amino acid residue other than aspartic acid (D) at a position corresponding to position 276 according to Ambler classification, wherein: the hydrophilic amino acid residue is asparagine (N) and the beta-lactamase hydrolyzes ceftriaxone substantially more efficiently than a beta-lactamase of SEQ ID NO: 1 that has an aspartic acid (D) at a position corresponding to position 276 according to Ambler classification.

In illustrative embodiments, the beta-lactamases and/or pharmaceutical compositions comprise an amino acid sequence having at least 90%, or 95%, or 97%, or 99% sequence identity with SEQ ID NO: 1 and a hydrophilic amino acid residue other than aspartic acid (D) at a position corresponding to position 276 according to Ambler classification, wherein: the hydrophilic amino acid residue is arginine (R) and the beta-lactamase hydrolyzes ceftriaxone substantially more efficiently than a beta-lactamase of SEQ ID NO: 1 that has an aspartic acid (D) at a position corresponding to position 276 according to Ambler classification.

In some embodiments, the beta-lactamases and/or pharmaceutical compositions comprise an amino acid sequence having at least 90%, or 95%, or 97%, or 99%, or 100% sequence identity with SEQ ID NO: 5, i.e. P3A:

SEQ ID NO: 5
TEMKDDFAKLEEQFDAKLGIFALDTGTNRTVAYRPDERFAFASTIKALTVG

VLLQQKSIEDLNQRITYTRDDLVNYNPITEKHVDTGMTLKELADASLRYSD

NAAQNLILKQIGGPESLKKELRKIGDEVTNPERFEPELNEVNPGETQDTST

ARALVTSLRAFALEDKLPSEKRELLIDWMKRNTTGDALIRAGVPDGWEVAD

KTGAASYGTRNDIAIIWPPKGDPVVLAVLSSRDKKDAKYDNKLIAEATKVV

MKALNMNGK.

In some embodiments, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 5.

An illustrative polynucleotide of the invention is SEQ ID NO: 6, which is the full nucleotide sequence of P3A:

SEQ ID NO: 6:
atgactgagatgaaagatgattttgcgaagctggaagaacagtttgacgca aaattgggcattttcgcgttggacacgggtacgaatcgtacggttgcctac cgtccggacgagcgcttcgccttcgcgagcacgatcaaagccctgaccgtc ggcgtgctgctccagcaaaagagcatcgaggacctgaaccagcgcattacc tacacccgtgatgatctggtgaactataatccgatcaccgagaaacacgtt gataccggtatgaccctgaaagaactggcagatgcaagcctgcgctacagc gataacgcggctcagaatctgattctgaagcaaatcggtggtccggagagc ttgaagaaagaactgcgtaaaatcggcgatgaagtcactaatccggagcgt tttgagccggagctgaacgaagtgaatccgggtgaaacgcaagacacgagc accgcgcgtgcgcttgtcacctccctgcgcgctttcgcactggaagataag ctgccgtcggagaaacgcgagctgctgatcgactggatgaagcgcaatacg accggcgacgcgctgattcgtgcgggcgttccggacggttgggaagtggct gacaagaccggtgcggcgagctacggcacccgtaacgatatcgcgatcatt tggccacctaaaggtgacccggtcgtgctggccgtactgagcagccgtgac aagaaagacgcaaagtatgataacaagctgattgcagaggcgaccaaagtt gttatgaaggcactgaacatgaatggtaag In some embodiments, the polynucleotide of the present invention has at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 6.

In illustrative embodiments, the beta-lactamases and/or pharmaceutical compositions comprise an amino acid sequence having at least 60% sequence identity with SEQ ID NO: 1 or SEQ ID NO: 3 and the following of Ambler classification: a hydrophobic residue other than alanine (A) at position 232; a hydrophilic residue other than alanine (A) at position 237; a hydrophobic residue other than alanine (A) at position 238; a hydrophilic residue other than serine (S) at position 240; and a hydrophilic residue other than aspartate (D) at position 276. In some embodiments, the hydrophobic residue other than alanine (A) at position 232 is glycine (G). In some embodiments, the hydrophilic residue other than alanine (A) at position 237 is serine (S). In some embodiments, the hydrophobic residue other than alanine (A) at position 238 is glycine (G). In some embodiments, the hydrophilic residue other than serine (S) at position 240 is aspartate (D). In some embodiments, the other than aspartate (D) at position 276 is asparagine (N). In some embodiments, the beta-lactamase and/or pharmaceutical composition comprises one or more of A232G, A237S, A238G, S240D, and D276N. In some embodiments, the beta-lactamase and/or pharmaceutical composition comprises all of A232G, A237S, A238G, S240D, and D276N, the sequence of which is SEQ ID NO: 7, i.e. P4A. In some embodiments, the beta-lactamase and/or pharmaceutical composition comprises an amino acid sequence having at least 90%, or 95%, or 97%, or 99%, or 100% sequence identity with SEQ ID NO: 7.

SEQ ID NO: 7
EMKDDFAKLEEQFDAKLGIFALDTGTNRTVAYRPDERFAFASTIKALTVGV

LLQQKSIEDLNQRITTRDDLVNYNPITEKHVDTGMTLKELADASLRYSDNA

AQNLILKQIGGPESLKKELRKIGDEVTNPERFEPELNEVNPGETQDTSTAR

ALVTSLRAFALEDKLPSEKRELLIDWMKRNTTGDALIRAGVPDGWEVGDKT

GSGDYGTRNDIAIIWPPKGDPVVLAVLSSRDKKDAKYDNKLIAEATKVVMK

ALNMNGK

In some embodiments, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 7.

SEQ ID NO: 8, is derived from SEQ ID NO: 7, and further includes the signal and the addition of the QASKT (SEQ ID NO: 11) amino acids (the coding region is underlined):

MIQKRKRTVSFRLVLMCTLLFVSLPITKTSAQASKT<u>EMKDDFAKLEEQFDA</u>

<u>KLGIFALDTGTNRTVAYRPDERFAFASTIKALTVGVLLQQKSIEDLNQRIT</u>

<u>YTRDDLVNYNPITEKHVDTGMTLKELADASLRYSDNAAQNLILKQIGGPES</u>

<u>LKKELRKIGDEVTNPERFEPELNEVNPGETQDTSTARALVTSLRAFALEDK</u>

<u>LPSEKRELLIDWMKRNTTGDALIRAGVPDGWEVGDKTGSGDYGTRNDIAII</u>

<u>WPPKGDPVVLAVLSSRDKKDAKYDNKLIAEATKVVMKALNMNGK</u>

In some embodiments, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 8.

In some embodiments, the beta-lactamase and/or pharmaceutical composition comprises an amino acid sequence having at least 90%, or 95%, or 97%, or 99%, or 100% sequence identity with SEQ ID NO: 8.

An illustrative polynucleotide of the invention is SEQ ID NO: 9, which is the full nucleotide sequence of A232G, A237S, A238G, S240D, and D276N mutant, Hind III site (AAGCTT—in bold) and additional K and T amino acids. In some embodiments, the underlined portion of SEQ ID NO: 9, is omitted. The leader and additional nucleotides (Hind III site and K and T amino acids—for the addition of the amino acid sequence QASKT (SEQ ID NO: 11)) are underlined.

<u>atgattcaaaaacgaaagcggacagtttcgttcagacttgtgcttatgtgc</u>

<u>acgctgttatttgtcagtttgccgattacaaaaacatcagcgc</u>aagcttcc aagacggagatgaaagatgattttgcaaaacttgaggaacaatttgatgca aaactcgggatcttt gcattggatacaggtacaaaccggacggtagcgtat cggccggatgagcgttttgcttttgcttcgacgattaaggctttaactgta ggcgtgcttttgcaacagaaatcaatagaagatctgaaccagagaataaca tatacacgtgatgatcttgtaaactacaacccgattacggaaaagcacgtt gatacgggaatgacgctcaaagagcttgcggatgcttcgcttcgatatagt gacaatgcggcacagaatctcattcttaaacaaattggcggacctgaaagt ttgaaaaaggaactgaggaagattggtgatgaggttacaaatcccgaacga ttcgaaccagagttaaatgaagtgaatccgggtgaaactcaggataccagt acagcaagagcacttgtcacaagccttcgagcctttgctcttgaagataaa cttccaagtgaaaaacgcgagcttttaatcgattggatgaaacgaaatacc actggagacgccttaatccgtgccggtgtgccggacggtgggaagtgggt gataaaactggaagcggagattatggaacccggaatgacattgccatcatt tggccgccaaaaggagatcctgtcgttcttgcagtattatccagcaggat aaaaaggacgccaagtatgataataaacttattgcagaggcaacaaaggtg gtaatgaaagccttaaacatgaacggcaaataa In some embodiments, the polynucleotide of the present invention has at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 9 (with or without the underlined portion).

In various aspects, the beta-lactamases polypeptide has the sequence of SEQ ID NO: 10 (i.e., P2A) or is derived by one or more mutations of SEQ ID NO: 10:

ETGTISISQLNKNVWVHTELGYFNGEAVPSNGLVLNTSKGLVLVDSSWDNK

LTKELIEMVEKKFQKRVTDVIITHAHADRIGGITALKERGIKAHSTALTAE

LAKNSGYEEPLGDLQTITSLKFGNTKVETFYPGKGHTEDNIVVWLPQYQIL

AGGCLVKSAEAKDLGNVADAYVNEWSTSIENVLKRYGNINSVVPGHGEVGD

KGLLLHTLDLLK.

In some embodiments, the beta-lactamase polypeptide produced by methods of the invention comprises an amino acid sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 10.

In some embodiments, the beta-lactamase and/or pharmaceutical composition comprises an amino acid sequence having at least 90%, or 95%, or 97%, or 99%, or 100% sequence identity with SEQ ID NO: 10.

Additional sequences of beta-lactamases including P1A, P2A, P3A, and P4A and derivatives thereof are described for example, in WO 2011/148041 and PCT/US2015/026457, the entire contents of which are hereby incorporated by reference.

The invention provides for polynucleotides encoding a beta-lactamase polypeptide, including, for example, vectors, comprising such polynucleotides. Such polynucleotides may further comprise, in addition to sequences encoding the beta-lactamases of the invention, one or more expression control elements. For example, the polynucleotide, may comprise one or more promoters or transcriptional enhancers, ribosomal binding sites, transcription termination signals, and polyadenylation signals, as expression control elements. In an embodiment, the polynucleotide includes expression control elements that direct expression of the beta-lactamase in the cytoplasm.

The polynucleotide may be inserted within a suitable vector, which is utilized to transform a suitable host cell such as an *E. coli* cell for expression. The vector may be any self-replicating DNA molecule that can transfer a DNA between host cells, including, for example, a plasmid cloning vector. In some embodiments, the vector can remain episomal or become chromosomally integrated, as long as the insert encoding the therapeutic agent can be transcribed. Vectors can be constructed by standard recombinant DNA technology. Vectors can be, for example, plasmids, phages, cosmids, phagemids, viruses, or any other types known in the art, which are used for replication and expression in prokaryotic or eukaryotic cells (e.g. an adenovirus; a retrovirus; a lentivirus; an scAAV; pGEX vector; pET vector; and pHT vector). Exemplary vectors that may be used include, for example, the pAVE011 vector. Preparations of the pAVE011 vector is described in EP Patent No. 0502637, EP Patent No. 2386642, and U.S. Pat. No. 6,537,779, the entire contents of which are hereby incorporated by reference. It will be appreciated by one of skill in the art that a wide variety of components known in the art (such as expression control elements) may be included in such vectors, including a wide variety of transcription signals, such as promoters and other sequences that regulate the binding of RNA polymerase onto the promoter. Any promoter known to be effective in *E. coli* cells in which the vector will be expressed can be used to initiate expression of the therapeutic agent. In one embodiment, the promoter is effective for directing expression of the beta-lactamase polypeptide in the cytoplasm. Suitable promoters may be inducible or constitutive. Examples of suitable promoters include, for example, the pET system (INVITROGEN), lac promoter, tac, trc, T7, T7A3 promoter, PhoA, Phage lambda pR, lambda pL promoter (see, e.g. *J Ind Microbiol Biotechnol* (2012) 39:383-399; *Curr Opin Biotech* 2001, 12: 195, the contents of which are hereby incorporated by reference), Pspac, PgroES, Pgsi, Plux and amyQ promoter and/or amyQ signal peptide from *Bacillus amyloliquefaciens* (by way of non-limiting example Gen Bank ID No. J01542.1, the contents of which are hereby incorporated by reference). The promoter may be inducible (e.g. via IPTG, metabolites, temperature). In one embodiment, the cytoplasmic expression of the beta-lactamase polypeptide is driven by the IPTG inducible LacI promoter. In one embodiment, cytoplasmic expression of the beta-lactamase polypeptide is induced by adding IPTG to the bacterial culture.

In various embodiments, the transformed *E. coli* cell is grown for a time under conditions sufficient to produce cytoplasmic expression of the beta-lactamase polypeptide. Any type of media that will support growth and reproduction of *E. coli* cell in cultures is useful for practicing the method of the invention. After growth of the cultures, the *E. coli* cell is typically lysed using osmotic shock, sonication or other standard means, and the expressed beta-lactamase polypeptide is isolated from the soluble fraction. Any protein purification method may be employed for this purpose, such as dialysis, gel filtration, ion exchange chromatography, affinity chromatography, electrophoresis, or a combination of steps.

In various embodiments, the beta-lactamases produced by methods of the invention possess functional characteristics that make them desirable for a variety of uses, including therapeutic uses. Methods of characterizing beta-lactamases are known in the art (e.g. nitrocefin assay as described by O'Callaghan, et al. *Antimicrob. Agents Chemother,* 1:283-288; the various methods of Viswanatha et al. *Methods Mol Med.* 2008; 142:239-60).

In one embodiment, the beta-lactamases produced by methods of the invention hydrolyze one or more of penicillins and cephalosporins. As used throughout, penicillins include, for example, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillin G (e.g. PENTIDS or PFIZERPEN); Penicillin V (e.g. VEETIDS (PEN-VEE-K)); Piperacillin (e.g. PIPRACIL); Temocillin (e.g. NEGABAN); and Ticarcillin (e.g. TICAR). As used throughout, cephalosporins include, for example, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). In a specific embodiment, cephalosporins include, for example, cefoperazone, ceftriaxone or cefazolin. In a specific embodiment, the inventive beta-lactamases have improved catalytic efficiency against cephalosporins as compared to SEQ ID NO: 1.

In various embodiments, the beta-lactamases possess desirable enzyme kinetic characteristics. For example, in some embodiments, the beta-lactamases possess a low $K_M$ for at least one cephalosporin, including, for example, a $K_M$ of less than about 500 μM, or about 100 μM, or about 10 μM, or about 1 μM, or about 0.1 μM (100 nM), or about 0.01 μM (10 nM), or about 1 nM. For example, in some embodiments, the beta-lactamases possess a low $K_M$ for at least one penicillin, including, for example, a $K_M$ of less than about 500 μM, or about 100 μM, or about 10 μM, or about 1 μM, or about 0.1 μM (100 nM), or about 0.01 μM (10 nM), or about 1 nM. In various embodiments, the inventive beta-lactamases possess a high $V_{max}$ for at least one cephalosporin, including, for example, $V_{max}$ which is greater than about 100 s-1, or about 1000 s-1, or about 10000 s-1, or about 100000 s-1, or about 1000000 s-1. In various embodiments, the inventive beta-lactamases possess a high $V_{max}$ for at least one penicillin, including, for example, $V_{max}$ which is greater than about 100 s-1, or about 1000 s-1, or about 10000 s-1, or about 100000 s-1, or about 1000000 s-1. In various embodiments, the inventive beta-lactamases possess catalytic efficiency is greater than about $10^6$ $M^{-1}$ $s^{-1}$ for at least one cephalosporin. In various embodiments, the inventive beta-lactamases possess catalytic efficiency is greater than about $10^6$ $M^{-1}$ $s^{-1}$ for at least one penicillin. In various embodiments, the inventive beta-lactamases possess the desirable enzyme kinetic characteristics for at least one of either or both of cephalosporins and penicillins.

In various embodiments, the inventive beta-lactamases are stable and/or active in the GI tract, e.g. in one or more of the mouth, esophagus, stomach, duodenum, small intestine, duodenum, jejunum, ileum, large intestine, colon transversum, colon descendens, colon *ascendens,* colon sigmoidenum, cecum, and rectum. In a specific embodiment, the beta-lactamase is stable in the large intestine, optionally selected from one or more of colon transversum, colon descendens, colon *ascendens*, colon sigmoidenum and cecum. In a specific embodiment, the beta-lactamase is stable in the small intestine, optionally selected from one or more of duodenum, jejunum, and ileum. In some embodiments, the beta-lactamase is resistant to proteases in the GI tract, including for example, the small intestine. In some embodiments, the beta-lactamase is substantially active at a pH of about 6.0 to about 7.5, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5 (including, for example, via formulation, as described herein). In various embodiments, the beta-lactamases of the present invention are resistant to one or more beta-lactamase inhibitors, optionally selected from avibactam, tazobactam, sulbactam, and clavulanic acid. In some embodiments, stable refers to an enzyme that has a long enough half-life and maintains enough activity for therapeutic effectiveness.

This invention is further illustrated by the following non-limiting examples.

EXAMPLES

Example 1: Production of Beta-Lactamases in *Bacillus* Strains

P1A-protein was produced by *Bacillus subtilis* RS310 production strain in approximately 10,000 liter fed-batch fermentation. The *Bacillus subtilis* RS310 strain was asporogenic, tryptophan auxotrophic and secreted P1A-protein into the culture broth. Specifically, cell culturing of the P1A-protein comprised two inoculum (1%) expansion stages in shake flasks (WCB vial→100 mL→2×1200 mL) followed by a seed fermentation stage (220 L, 2.5%). The main fed-batch fermentation was conducted in approximately 10,000 L working volume. The main fermentation was started as batch fermentation with an initial volume of 9,000 L of growth medium. After about 9 hours when most of glucose in the growth medium was consumed, feeding with a feed solution (approx. 1500-2000 L) containing glucose and phosphate was started. In order to keep glucose at adequate levels (0.5-5 mg/mL) during the feeding phase, predefined feeding profile was used, which may be adjusted during the process based on glucose measurements. The P1A protein was constitutively produced and secreted extracellularly into the culture broth.

During fermentation the critical operational parameters were monitored and controlled including glucose concentration, pH (7±0.2), dissolved oxygen level (10-20%), temperature (37±1° C.) and foam level. Stirring rate was controlled starting with gentle mixing and increasing to a maximum of 138-145 rpm. Air flow into the vessel was adjusted to 0.5-1 wm. Progression of fermentation was monitored by P1A content (enzyme activity measurement) and cell density measurements (OD 600 nm). The main fermentation achieved a P1A titer of about 1-1.2 mg/mL (by HPLC) typically after 16-22 hours. The final cell density was typically approximately OD 50 (d.w. 16-17 g/L). After completion of cultivation, the content of fermenter was cooled down to 11±3 00.

After fermentation the cells were removed from P1A-protein containing broth by continuous centrifugation followed by microfiltration. P1A containing filtrate was concentrated by ultrafiltration and P1A concentrate was further diafiltered, conditioned and passed through a disposable anion exchange filter cartridge in flow-through mode after which the filtrate was further diafiltered to remove NaCl. This prepared the solution for the following two stage P1A-protein crystallisation including; crystallisation, crystal harvesting, washing and dissolution. Finally, after the second crystallisation step, P1A-protein crystals were suspended in water and dissolved and final concentration of P1A-protein solution was adjusted. The protein solution was filtered (0.2 um) to reduce bioburden and finally dispensed into sterile plastic containers, frozen and stored at −70° C.

Example 2: Intracellular Gene Design for the Expression of P3A β-Lactamase

The purpose of this study was to improve β-lactamase expression. To do so, the pAVEway™ advance protein expression system was employed in *E. coli*. P3A was used throughout this study for testing β-lactamase expression. The gene sequence for directing the intracellular expression of P3A is SEQ ID NO: 6.

The P3A gene was cloned into the pAVEway™ intercellular (cytoplasmic) construct, pAVE011, and the plasmid was verified with PCR and DNA sequencing. The designed P3A expression construct provided a relatively homogeneous N-terminus with the N-terminal methionine removed about 95% of the time.

Following construction of the intercellular expression plasmid, the construct was transformed in the following *E. coli* strains: CLD977 (W3110 *E. coli* host) and CLD990 (BL21 *E. coli* host). After construction of the β-lactamase intracellular expression strains, P3A was expressed and characterized as further described in Examples 2 and 3, respectively.

Additionally, the P3A gene was cloned into the pAVEway™ periplasmic construct, pAVE029+gene 1 or gene 7 (gene 1 and gene 7 are different secretion leaders). Again, the plasmid was verified with PCR and DNA sequencing.

Following construction of the periplasmic expression plasmid, the construct was transformed in the following *E. coli* strains: CLD981 (gene 1 leader, W3110 *E. coli* host) and CLD982 (gene 7 leader, BL21 *E. coli* host). After construction of the periplasmic β-lactamase expression strains, P3A was expressed and characterized as further described in Examples 2 and 3, respectively.

Example 3: P3A β-lactamase Fermentation

Duplicate fermentations were performed using intracellular expression strains CLD977 and CLD990, and periplasmic strains CLD981 and CLD982. Specifically, the fermentation analysis was carried out in 3 stages: Shake flask (SF) seed stage, Fermenter stage, and SDS-PAGE analysis stage. To carry out the SF seed stage, RCB vials were inoculated into duplicate shake flasks with standard media and incubated at 37° C., 200 rpm for approximately 10 hours. Next, purity and $OD_{600}$ of the samples was determined (summarized in Table 1). Finally, the *E. coli* material was transferred from SF to a fermentation vessel.

TABLE 1

Results from the shake flask seed stage for intracellular
strains CLD977 and CLD990. SF1 and SF2 correspond to duplicate
reactions for CLD977 and CLD990, respectively.

| SF | RCB vial | Incubation time | Final OD600 | Purity | OD600 values | Transfer to |
|---|---|---|---|---|---|---|
| SF1 | CLD977 | 9.97 h | 3.60 | Pure | 3.60 | |
| SF2 | NBJ1605-04 B3214 (P3A) | 9.97 h | 3.61 | Pure | 3.61 | C3 |
| SF1 | CLD990 | 9.97 h | 1.37 | Pure | 1.37 | |
| SF2 | NBJ1605-07 B3214 (P3A) | 9.97 h | 1.55 | Pure | 1.55 | C4 |

The fermenter stage was conducted using the standard pAVEway™ intracellular protocol. Specifically, cultures were induced using 0.5 mM IPTG when $OD_{600}$=50±5. After induction, fermentation continued for an additional 12 hours before shutdown. Purity of the samples was confirmed at both pre-induction and shutdown.

For CLD977, the fermentation control parameter steps were: i) Oxygen supplementation at 7.33 hours; ii) End of batch phase at 9.46 hours when feed started; iii) Induction at 10.27 hours when $OD_{600}$=50.1; iv) Fermentation continued for a further 12 hours before shutdown.

As shown in FIG. 1 (a multi-fermenter computer system (MFCS) plot of CLD977 fermentation), at approximately 20 hours, the airflow began to fail, which was suspected to be due to pressure in the vessel. Also, shown in FIG. 1, pO2 fell below 20% at approximately 21 hours and 1.5 hours prior to shut down.

For CLD990, the fermentation control parameter steps were: i) Oxygen supplementation at 10.95 hours; ii) End of batch phase at 12.27 hours when feed started; iii) Induction at 13.14 hours when $OD_{600}$=50.1; iv) Fermentation continued for a further 12 hours before shutdown.

Figure 2:
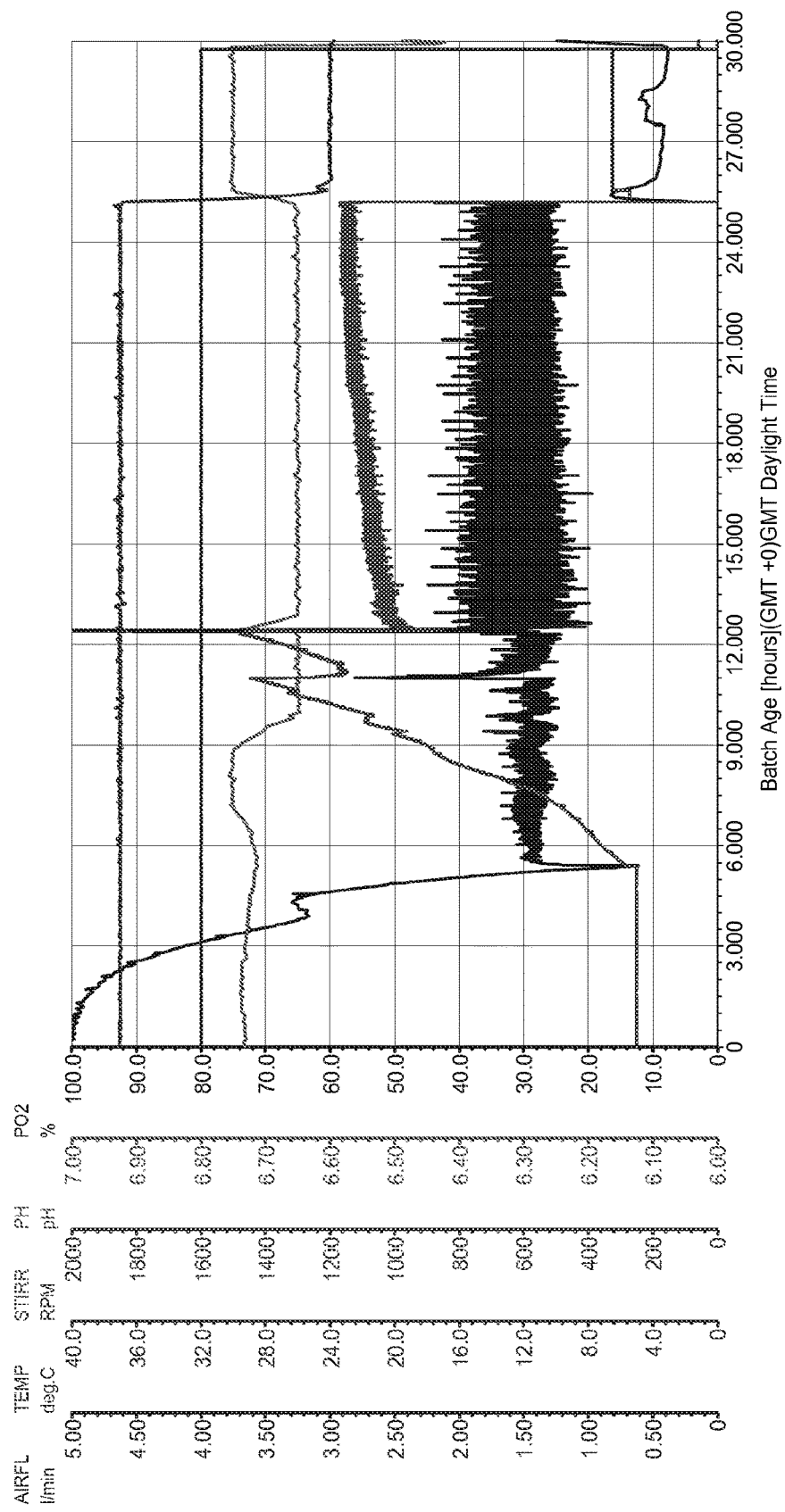
FIG. 2 shows a MFCS CLD990 fermentation plot of batch age (hours) vs. airflow (AIRFL (l/min), second line from top), temperature (TEMP (° C.), top line), stirring rate (STIRR (RPM), second line from the bottom), pH (third line), and percent oxygen ($PO_2$, bottom line).

A MFCS plot of CLD990 fermentation is shown in FIG. 2.

Figure 3:
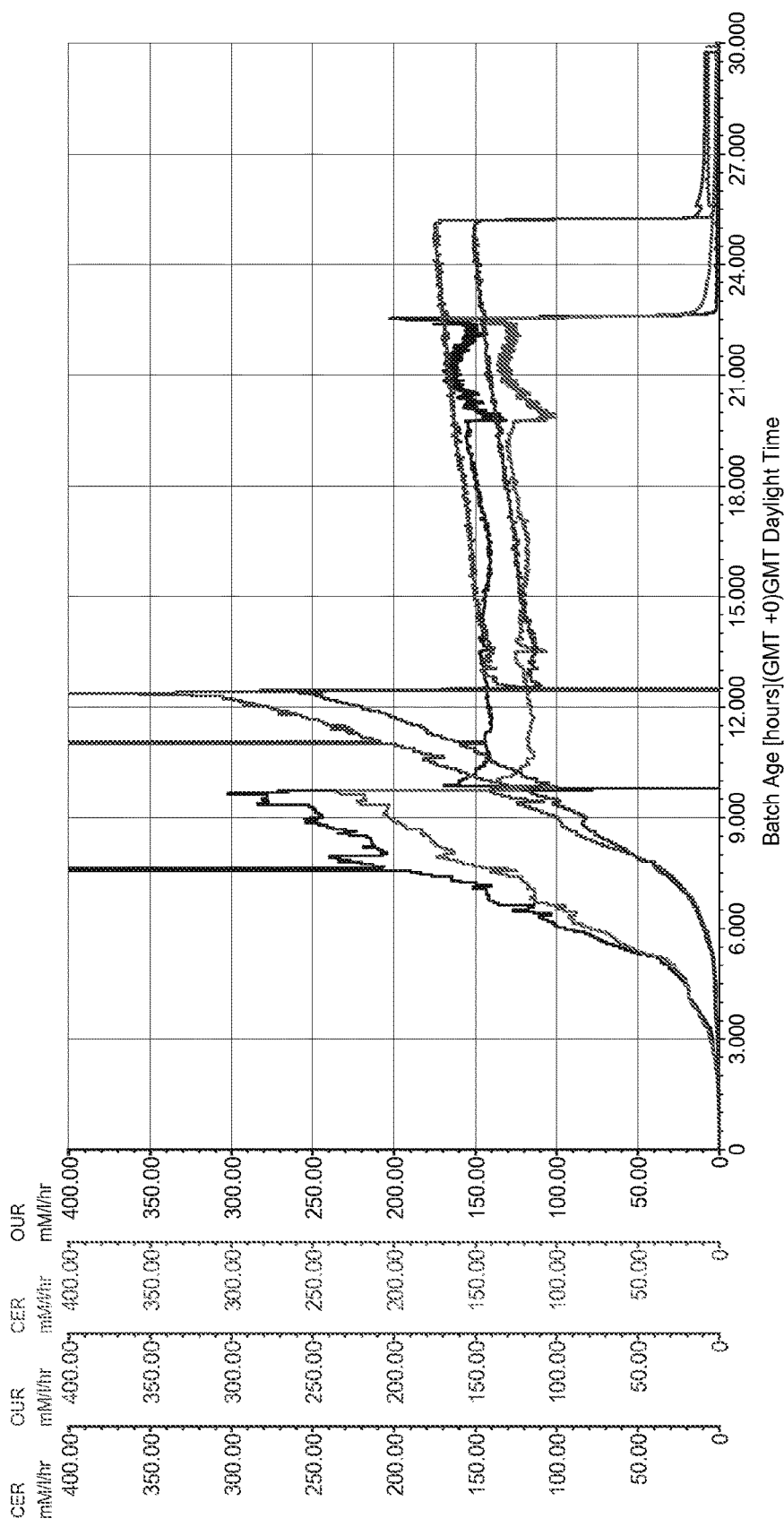
FIG. 3 shows a MFCS fermentation exit gas analysis plot of batch age (hours) vs. CLD977 (3/13C039) and CLD990 (4/13C040) oxygen uptake rate (OUR) and carbon dioxide evolution rate (CER) (mM/l/hr). Labeled from left to right, the first line corresponds to CLD977 OUR, the second line corresponds to CLD977 CER, the third line corresponds to CLD990 OUR and the fourth line corresponds to CLD990 CER.

A MFCS plot of exit gas analysis of oxygen uptake rate (OUR) and carbon dioxide evolution rate (CER) for CLD977 and CLD990 fermentation is shown in FIG. 3. Similar profiles were observed for both strains with the delay seen on the CLD990 strain due to an observed longer batch phase. Profile at the end of CLD977 fermentation, without wishing to be bound by theory, was probably related to a reduced airflow in the vessel (exit filter blocked).

Figure 4:
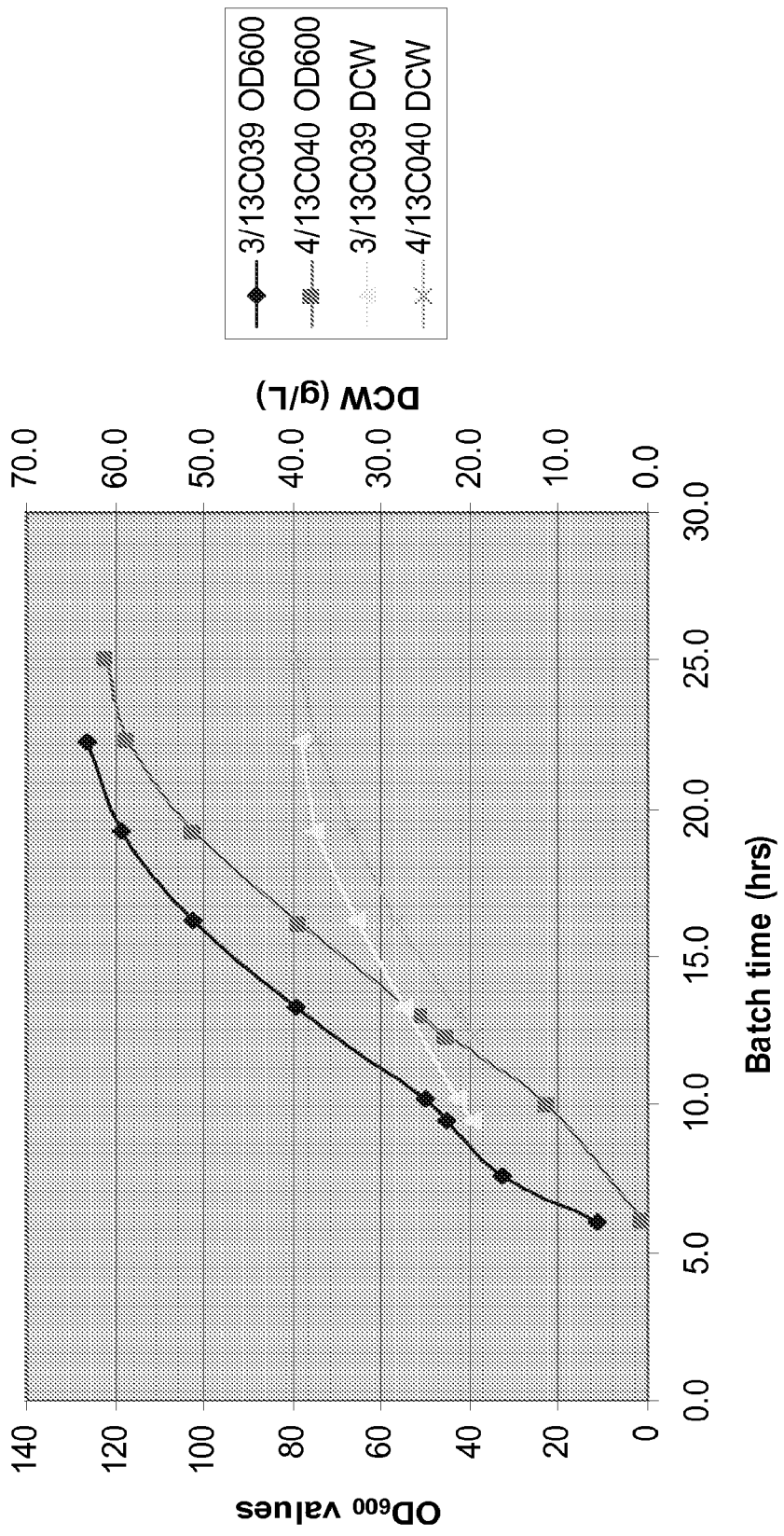
FIG. 4 shows a biomass plot for CLD977 (3/13C039) and CLD990 (4/13C040) of batch time (hours) vs. $OD_{600}$ and dry cell weight (DCW (g/L)). CLD977 $OD_{600}$ and DCW lines correspond to the top line and second from bottom line, respectively. CLD990 $OD_{600}$ and DCW lines correspond to the second from top line and bottom line, respectively.

Biomass profiles for both strains were similar up to 12 hours post induction although the CLD990 strain was delayed due to the extended batch phase (see FIG. 4). This delay, without wishing to be bound by theory, may have been due to the lower SF $OD_{600}$ or a reduced initial growth rate.

Figure 5:
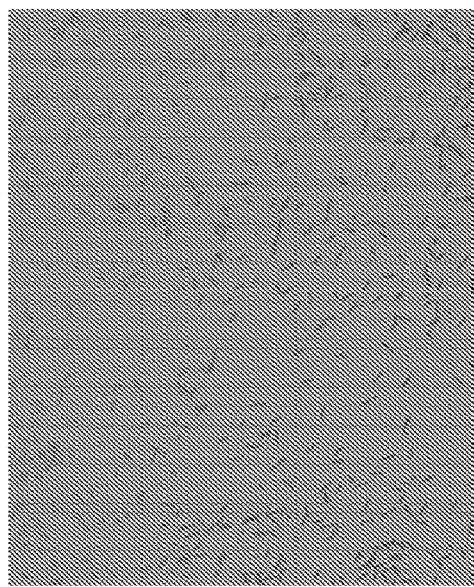
FIG. 5 shows bacterial gram stains for CLD977 and CLD990 at the end of batch phase and after fermentation is complete (final sample).
Figure 5:
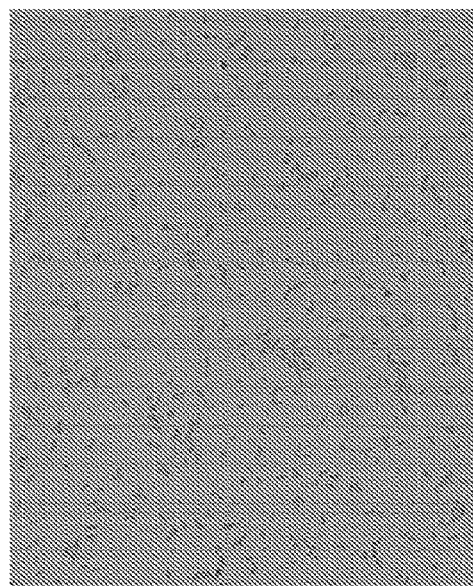
Figure 5:
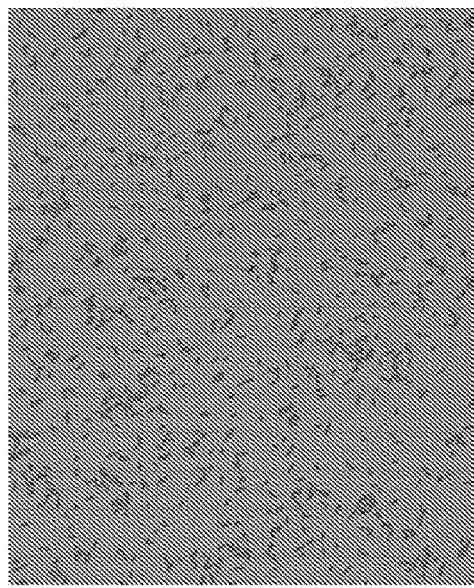

Gram staining was also performed for CLD977 and CLD990 at the end of batch phase and after fermentation was complete (see FIG. 5). Results indicate that the culture was pure and homogenous at the end of the culturing.

Figure 6:
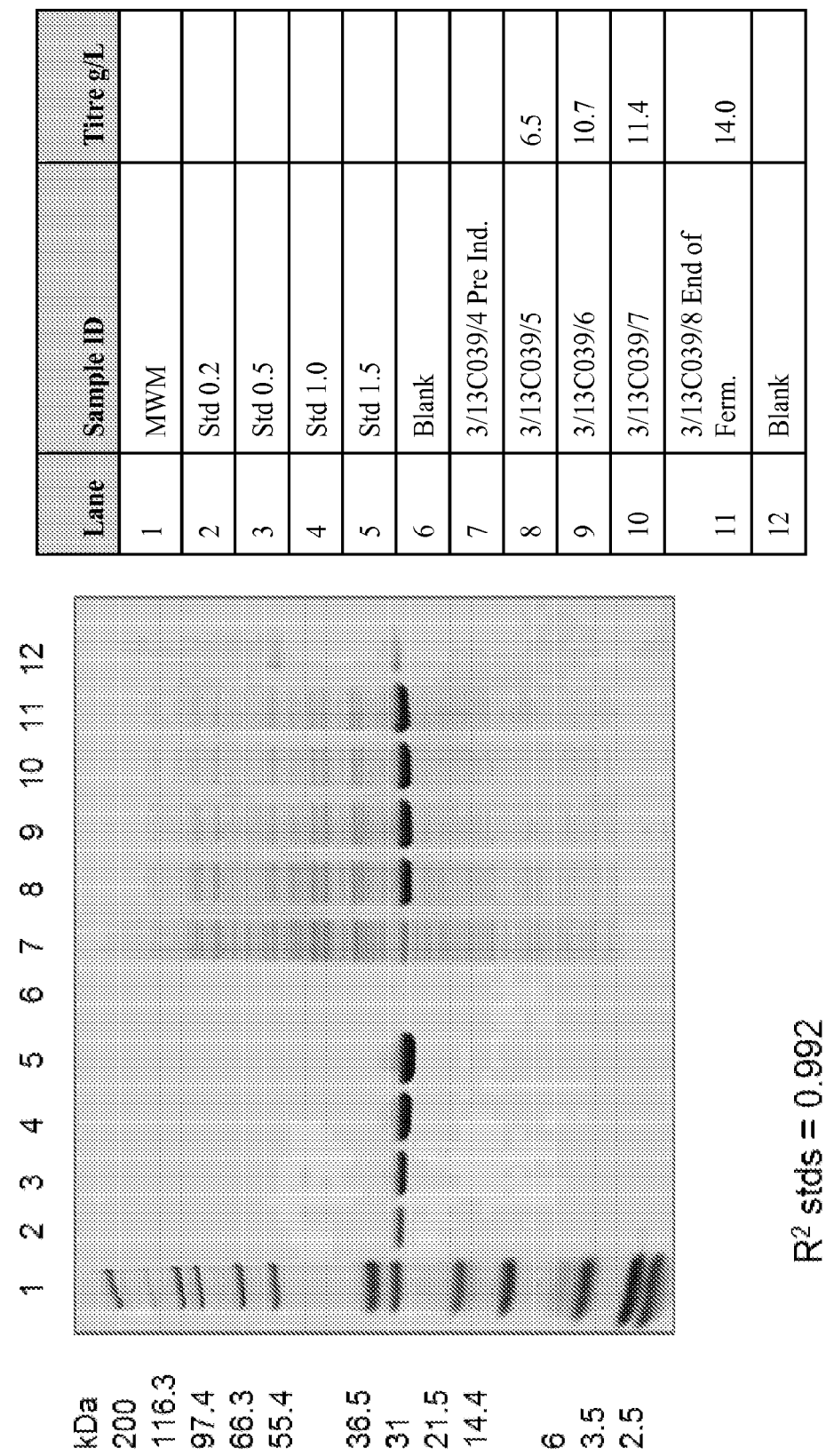
FIG. 6 shows SDS PAGE analysis of CLD977 (3/13C039) time course samples from pre-induction to the end of fermentation compared to control standards.
Figure 7:
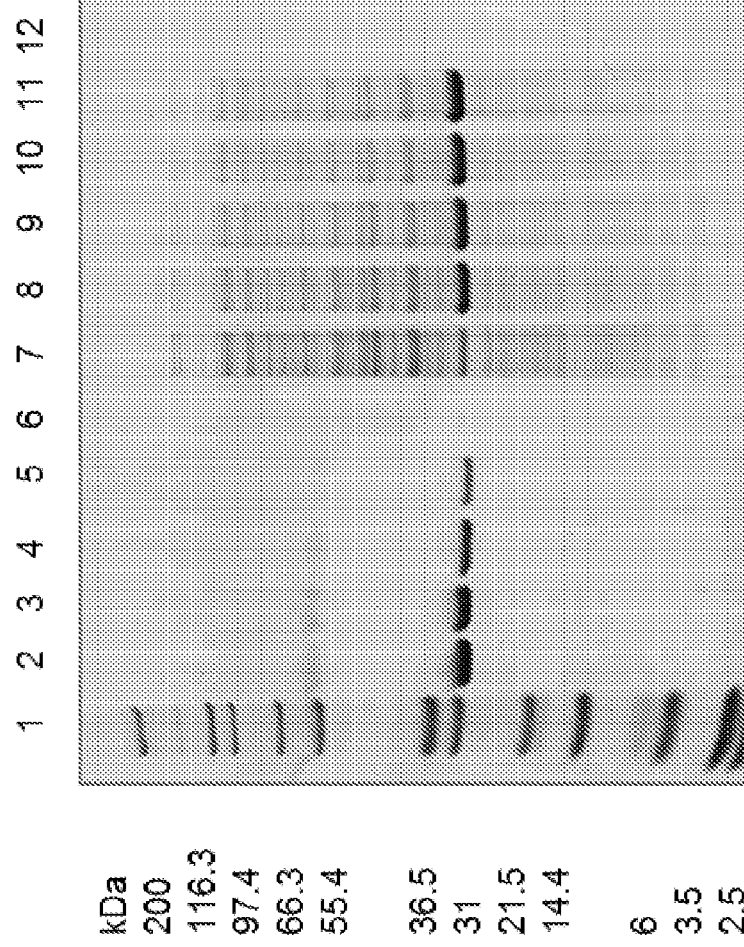
FIG. 7 shows SDS PAGE analysis of CLD990 (4/13C040) time course samples from pre-induction to the end of fermentation compared to control standards.
Figure 8:
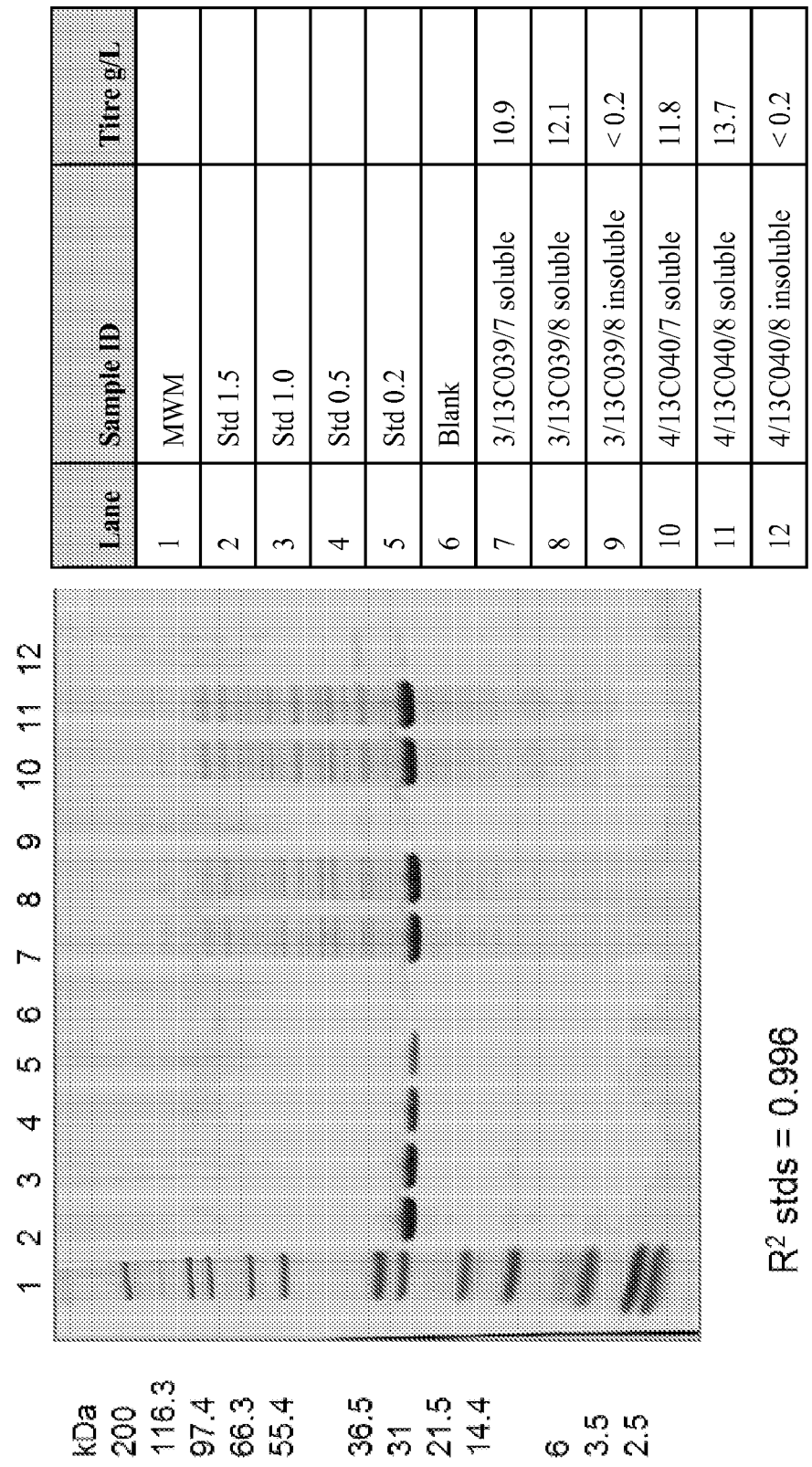
FIG. 8 shows SDS PAGE analysis of sonicated samples from CLD977 (3/13C039) and CLD990 (4/13C040) compared to control standards. CLD977 and CLD990 yielded mostly soluble protein. Only faint product bands are seen for the insoluble fraction.

Following fermentation, selected time course samples from pre-induction to the end of fermentation were analyzed using SDS-PAGE (see FIGS. 6-8) after samples were lysed, spun down, and resuspended.

As evidenced by the SDS-PAGE results, protein product levels in both strains were in excess of 10 g/L (see FIGS. 6 and 7): CLD977 SDS PAGE indicated 12.1-14.0 g/L whereas CLD990 SDS PAGE indicated 13.2-13.7 g/L. Additionally, the CLD977 and CLD990 total protein products (after sonication) were mostly soluble (see FIG. 8). Compared to previous systems used to express β-lactamase (that yielded about 0.5 to 1 g/L), the methods of the present invention utilizing intracellular expression of β-lactamase in *E. coli* strains proved to be far superior. Contrary to prior studies which show periplasmic β-lactamase expression, attempts to express β-lactamase in the periplasmic domain were unsuccessful and led to biologically inactive β-lactamase (see Example 3).

Example 4: β-lactamase Activity of Fermentation Samples by the CENTA Method

P3A β-lactamase activity of the previously described fermentation samples (see Example 2) was analyzed using the CENTA method, which is described below. Throughout this method, different standards were used and are referred to as: Reference material (32 mg/mL); Standard curve: Reference standard material diluted ×1000 (standards used were 0.6 mg/l, 0.8 mg/l, 1.0 mg/l, 1.5 mg/l, 2.0 mg/l and 4.0 mg/l made up from the ×1000 stock); Control standard: Reference standard diluted to 1 mg/l and ran as a control; 1 mM CENTA stock solution: 25 mg CENTA lactamase substrate dissolved in 50 ml of 50 mM Sodium dihydrogen phosphate (stored at −20° C.); and CENTA working solution: 3.34 ml of CENTA stock solution dissolved in 25 ml of Sodium dihydrogen phosphate.

The CENTA method employs a chromogenic cephalosporin that is readily hydrolyzed by β-lactamases and allows for kinetic studies and detection of the enzymes in crude extracts and chromatographic fractions (Bebrone, C. et al., (2001) Antimicrobial Agents and Chemotherapy, 45 (6) 1868-1871). This method is also useful since CENTA can be prepared from the commercially available drug, cephalothin. For this study, β-lactamase sample activity was monitored using a FFDB plate reader in the presence of a CENTA working solution. First, β-lactamase samples were diluted to 1 mg/l (Bradford assays were used to determine the concentration). Then, 50 μL of each sample was loaded onto the plate and incubated for 20 min. at 25° C. Finally, 200 μL of the CENTA working solution was added to each sample and the sample was read as follows: Plate reader settings: Temperature of measurement=25° C.; Shaking=slow; Time of shaking=2 seconds; Time of measurement=60 seconds; Number of readings=Every 3 seconds; and Wavelength=405 nm.

The hydrolysis of CENTA was monitored by continuously recording the absorbance variation at 405 nm (appearance of the expulsed chromophore). Results from this assay are presented in FIGS. 9-19 and summarized in Tables 2-4.

The CENTA experiments were split into 3 assay plates. Assay plate 1 corresponded to: CLD981 12 h, 24 h, 48 h, osmotic shock buffer 1 (OS1) 24 h, and osmotic shock buffer 2 (OS2) 24 h post induction, as well as CLD982 12 h, 24 h, 48 h, OS1 24 h, and OS2 24 h post induction. Assay plate 2 corresponded to: CLD981 OS1 48 h and OS2 48 h post induction, as well as CLD982 OS1 48 h and OS2 48 h post induction. Assay plate 3 corresponded to CLD977 and CLD990 for both the second to last and last time point post induction (sonication) as well as the last time point post induction (Bug buster). OS1 contains 20% sucrose. Following preparation of the OS1 fraction, the cell pellet went on to preparation of OS2, which contains $MgSO_4$.

Figure 9:
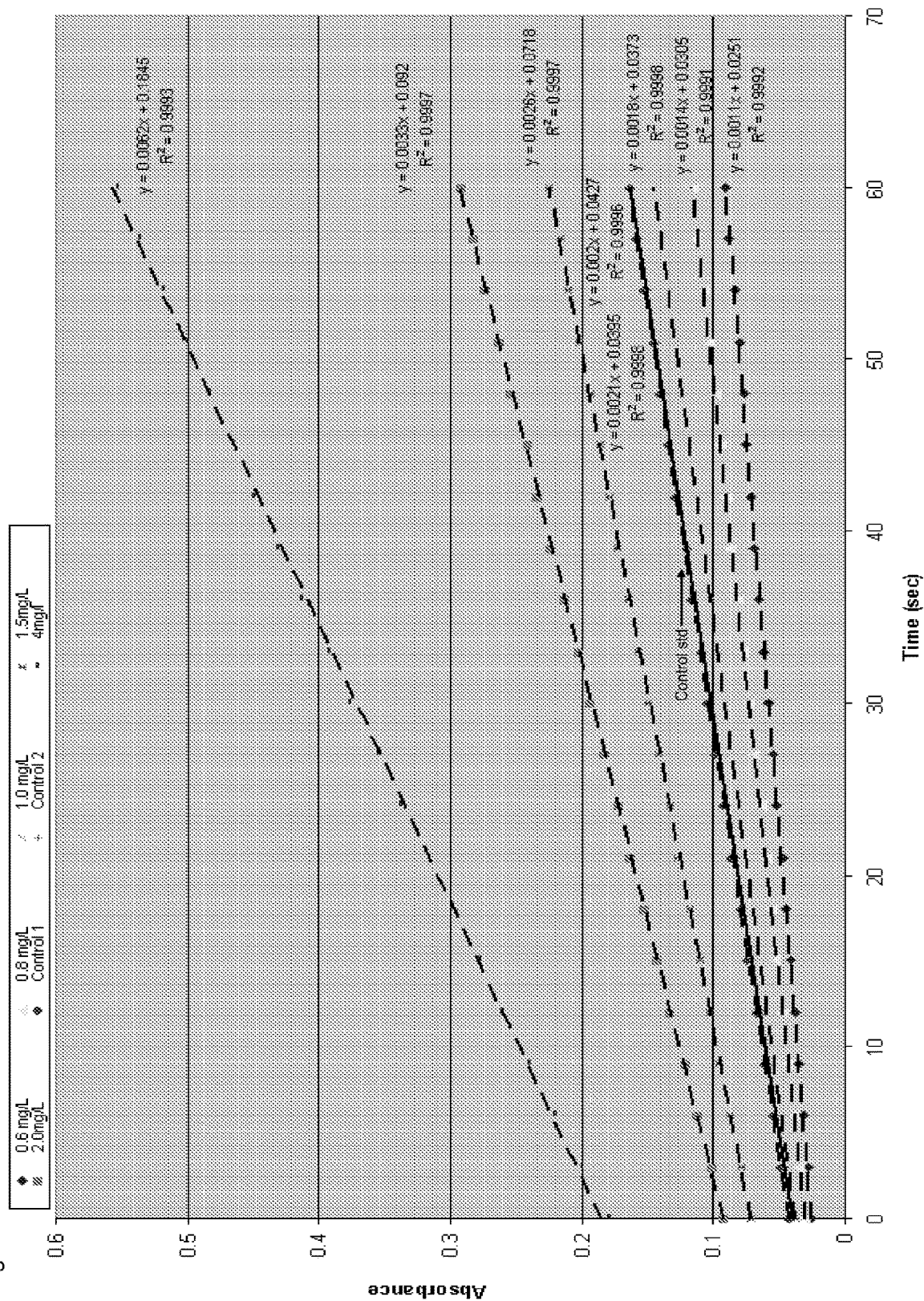
FIG. 9 shows a standard curve of Time (sec) vs. Absorbance for Controls 1 and 2 as well as reference standard dilutions of 0.6, 0.8, 1.0, 1.5, 2.0, and 4 mg/L. Controls 1 and 2 were preset dilutions of 1.0 μg/mL ran as duplicates.
Figure 10:
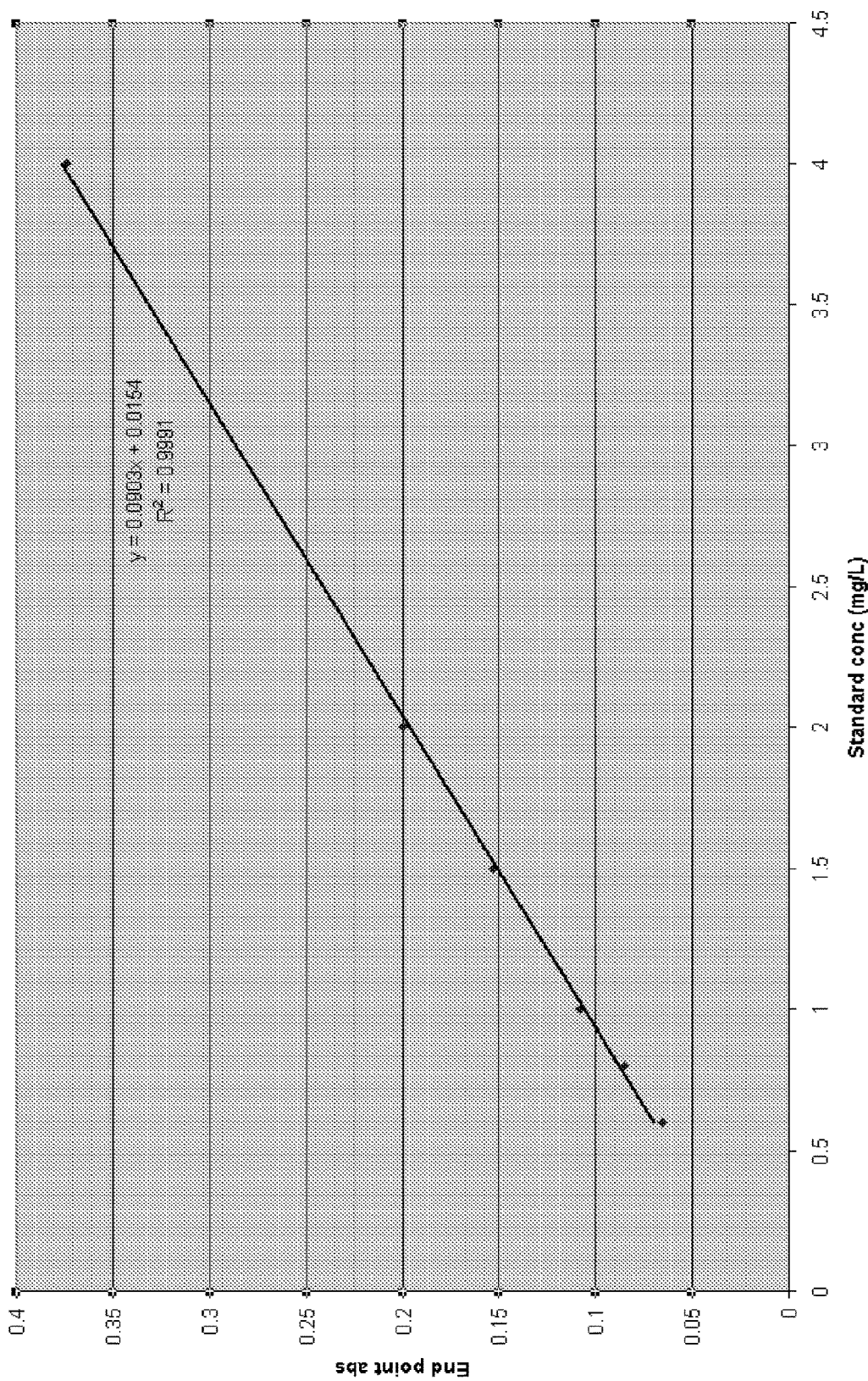
FIG. 10 shows a standard end point curve of Standard Concentration (mg/L) vs. End Point Absorbance. Standard absorbance was measured at time=60 sec minus standard absorbance at time=0 sec. Specifically, enzymatic reaction was measured at time=60 sec. The absorbance was measured at time=0 sec which was then subtracted from the 60 sec measurement. Several dilutions of the reference standard were tested to generate a standard curve.

Results for assay plate 1 results are shown in FIGS. 9-13 and Table 2. Specifically, FIG. 9 shows a standard curve of Time (sec) vs. Absorbance for Controls 1 and 2 (combined into control standard) as well as reference standard material dilutions of 0.6, 0.8, 1.0, 1.5, 2.0, and 4 mg/L. Controls 1 and 2 were preset dilutions of 1.0 μg/mL ran as duplicates. FIG.

Figure 11:
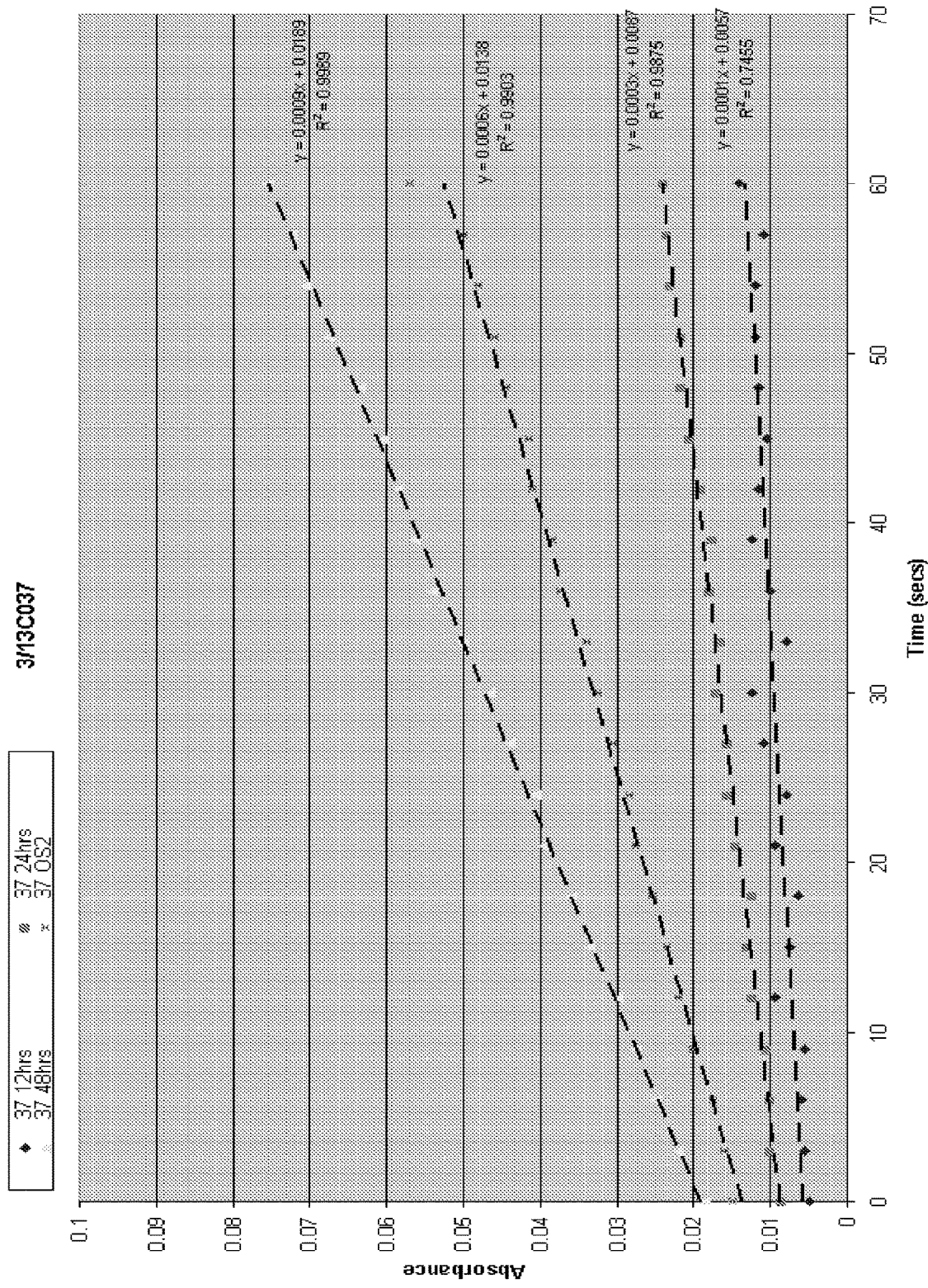
FIG. 11 shows a standard curve of Time (sec) vs. Absorbance for CLD981 (3/13C037 (also referred to as 37)) at 12 hours, 24 hours, 48 hours, as well as the periplasmic osmotic shock fraction (OS2). Specifically, OS2 is the second buffer fraction prepared from an E. coli pellet and represents the periplasmic space fraction.
Figure 12:
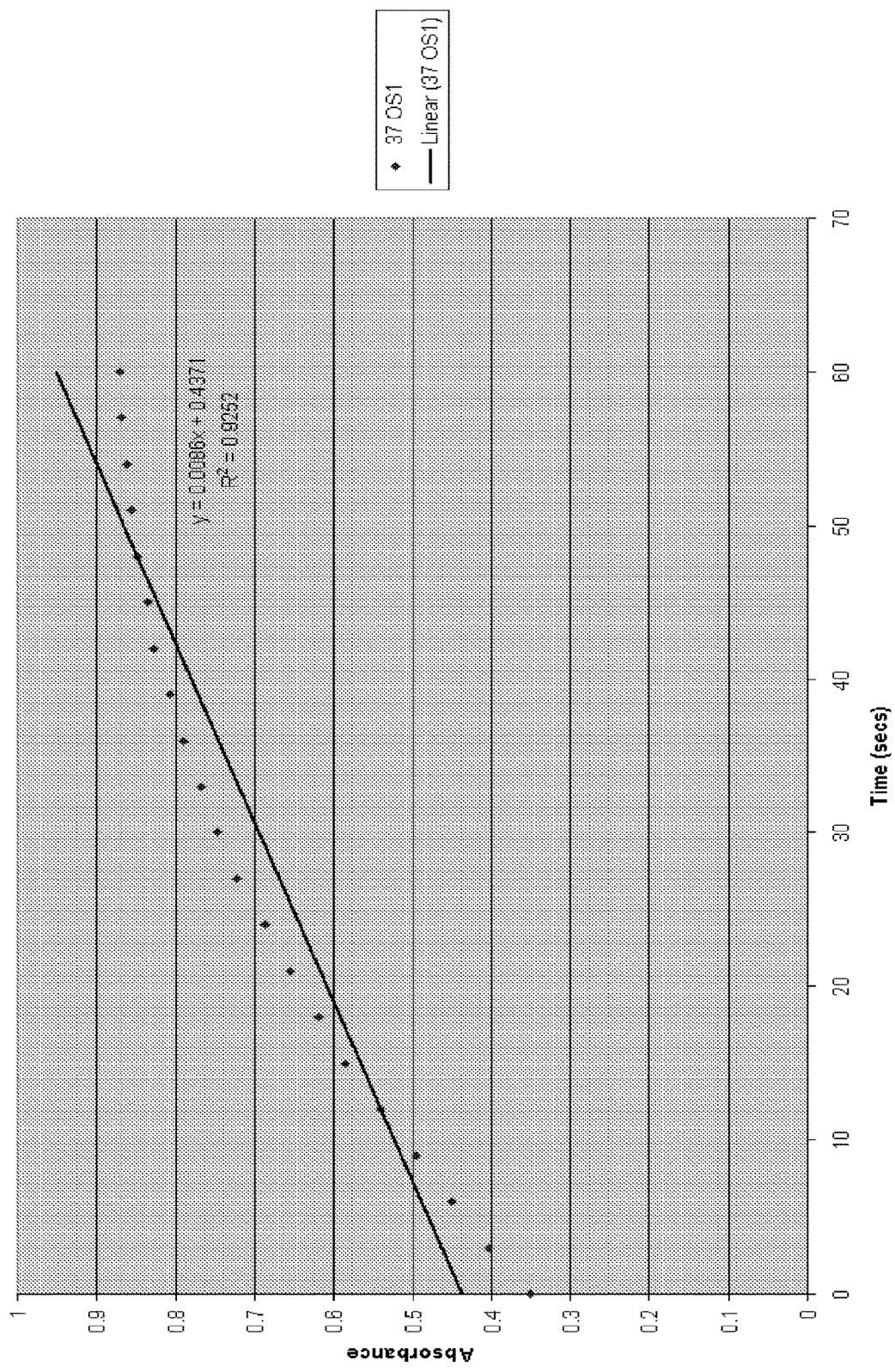
FIG. 12 shows a standard end point curve of Time (sec) vs. Absorbance for CLD981 (3/13C037) OS1 samples.
Figure 13:
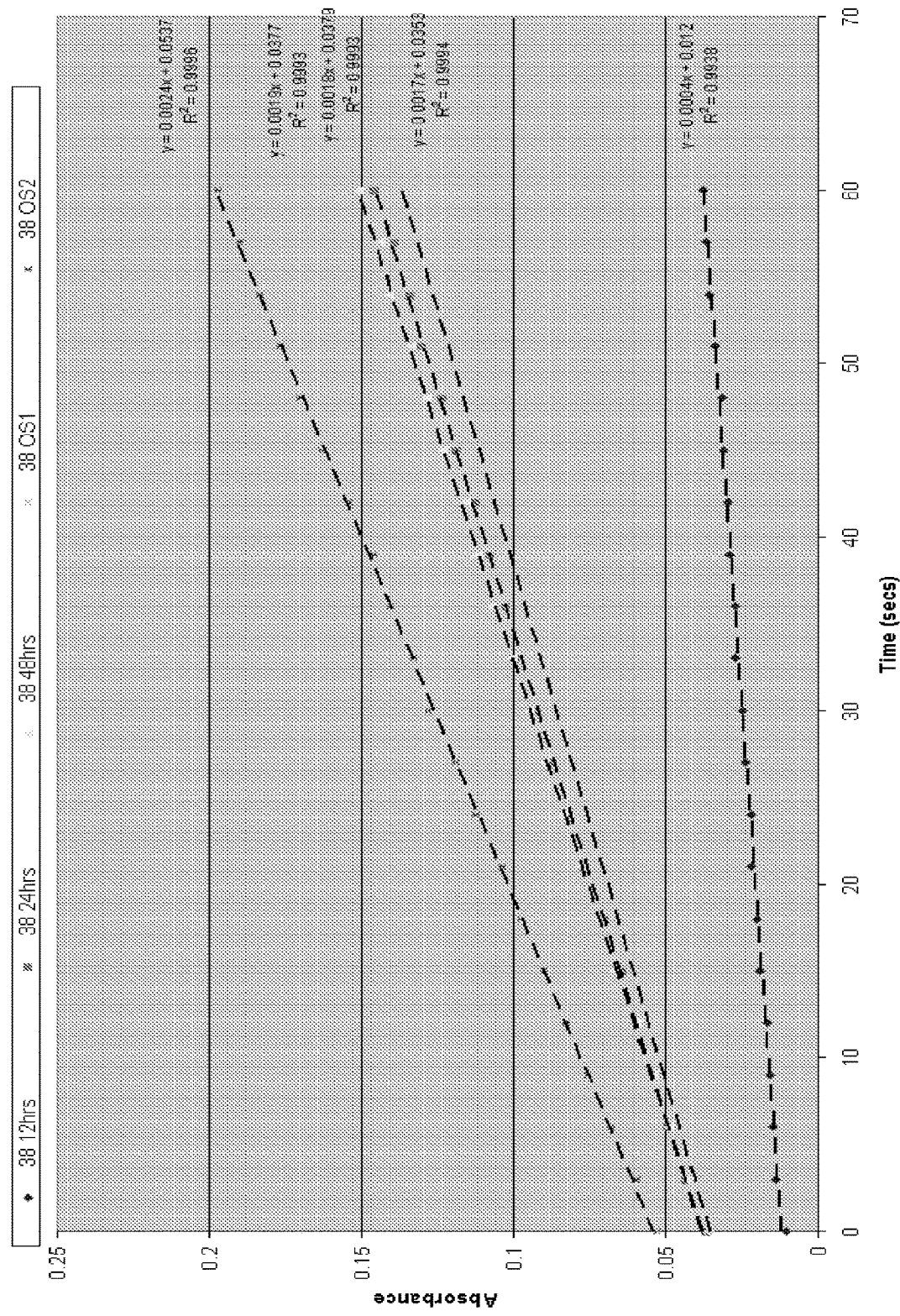
FIG. 13 shows a standard curve of Time (sec) vs. Absorbance for CLD982 (4/13C038 (also referred to as 38)) 12 h, 24 h, 48 h, and OS1 and OS2 48 h post induction.

10 shows a standard end point curve of Standard Concentration (mg/L) vs. End Point Absorbance. Standard absorbance was measured at time=60 sec minus standard absorbance at time=0 sec. Specifically, endpoint analysis was carried out in which a reaction was measured at t=0 and at the end of a specified time interval, and the t=0 absorbance value was subtracted. For analysis of beta-lactamase, the reaction was measured at time=60 sec. The absorbance was measured at time=0 sec which was then subtracted from the 60 sec measurement. Several dilutions of the reference standard were tested to generate a standard curve. FIG. 11 shows a standard curve of Time (sec) vs. Absorbance for CLD981 (3/13C037) 12 h, 24 h, 48 h, and OS2 48 h post induction. FIG. 12 shows a standard end point curve of Time (sec) vs. Absorbance for CLD981 OS1 samples. FIG. 13 shows a standard curve of Time (sec) vs. Absorbance for CLD982 (4/13C038) 12 h, 24 h, 48 h, and OS1 and OS2 48 h post induction. Table 2 shows a summary of assay plate 1 activity and titre results for CLD981 and CLD982 (secretion strains 37 and 38, respectively) along with controls 1 and 2.

Figure 14:
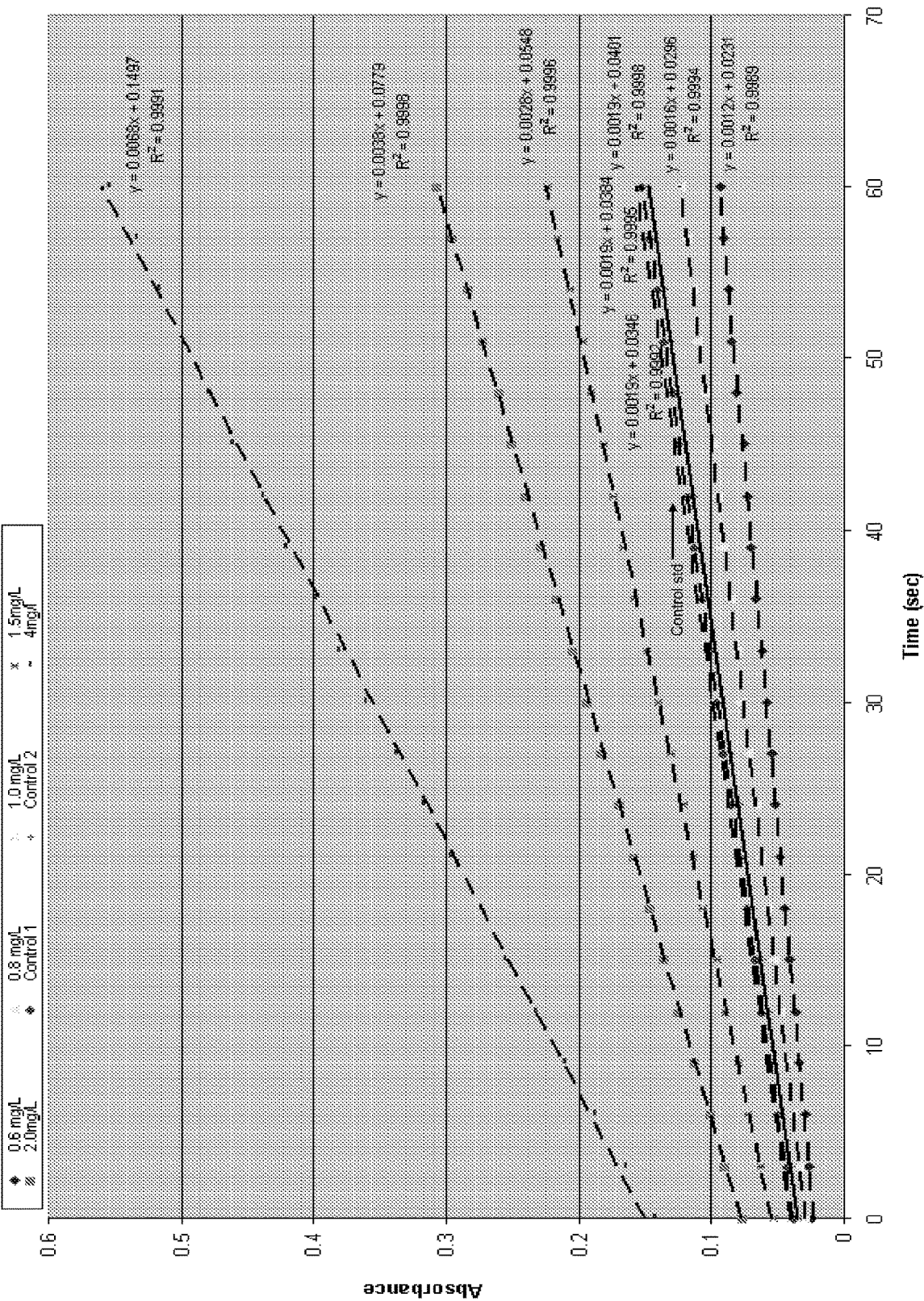
FIG. 14 shows a standard curve of Time (sec) vs. Absorbance for Control 1 and 2 (combined into control standard) as well as reference standard material dilutions of 0.6, 0.8, 1.0, 1.5, 2.0, and 4 mg/L.
Figure 15:
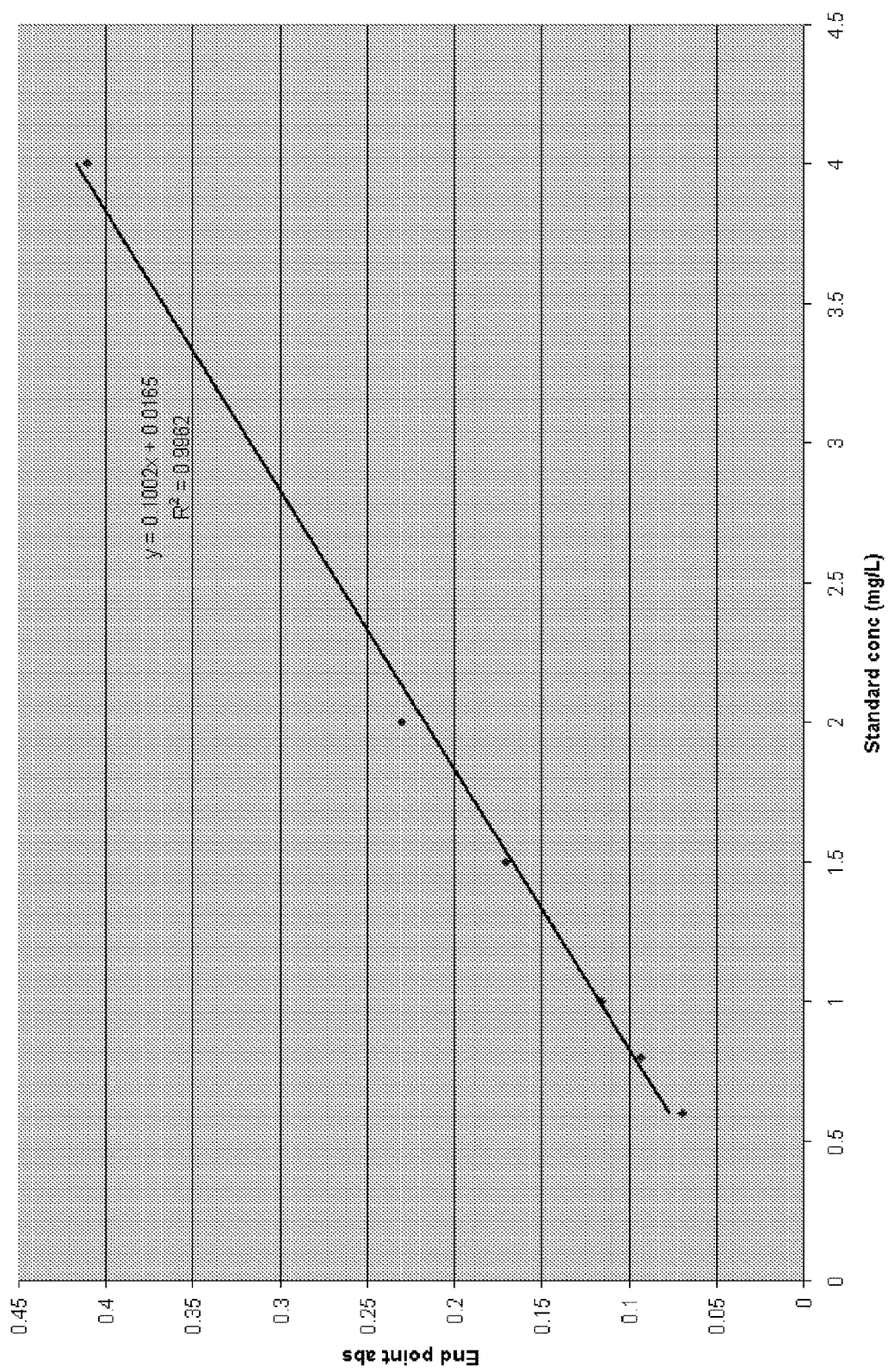
FIG. 15 shows a standard end point curve of Standard Concentration (mg/L) vs. End Point Absorbance. Standard absorbance was measured at time=60 sec minus standard absorbance at time=0 sec.
Figure 16:
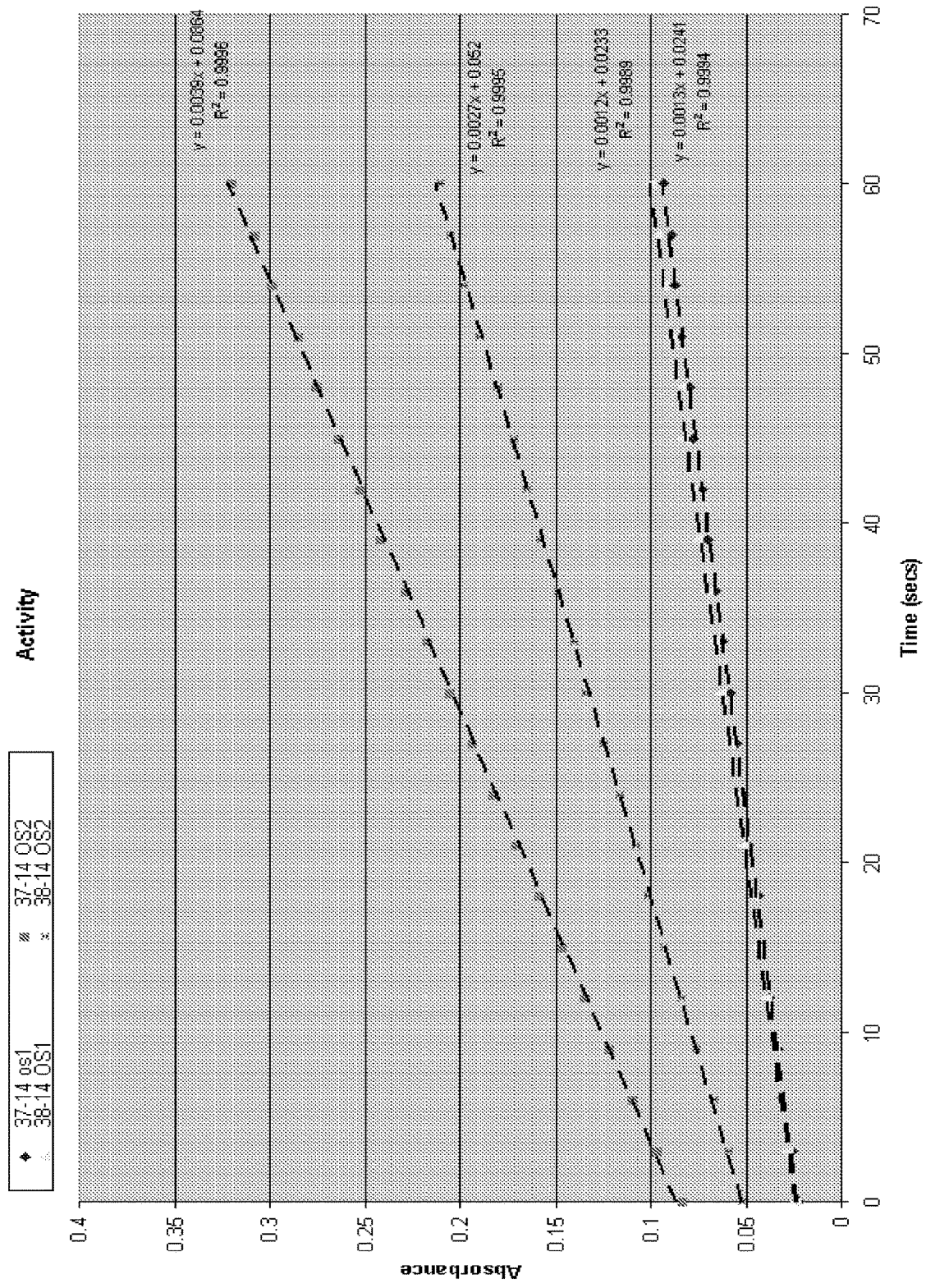
FIG. 16 shows a standard curve of Time (sec) vs. Absorbance for CLD981 (37) and CLD982 (38) OS1 and OS2 48 h post induction. Table 3 is a summary of assay plate 2 activity and titer results for CLD981 and CLD982 OS1 and OS2 along with controls 1 and 2.

Assay plate 2 results are shown in FIGS. 14-16 and Table 3. Specifically, FIG. 14 shows a standard curve of Time (sec) vs. Absorbance for Control 1 and 2 (combined into control standard) as well as reference standard material dilutions of 0.6, 0.8, 1.0, 1.5, 2.0, and 4 mg/L. FIG. 15 shows a standard end point curve of Standard Concentration (mg/L) vs. End Point Absorbance. Standard absorbance was measured at time=60 sec minus standard absorbance at time=0 sec. FIG. 16 shows a standard curve of Time (sec) vs. Absorbance for CLD981 (37) and CLD982 (38) OS1 and OS2 48 h post induction. Table 3 shows a summary of assay plate 2 activity and titre results for CLD981 and CLD982 OS1 and OS2 along with controls 1 and 2.

Figure 17:
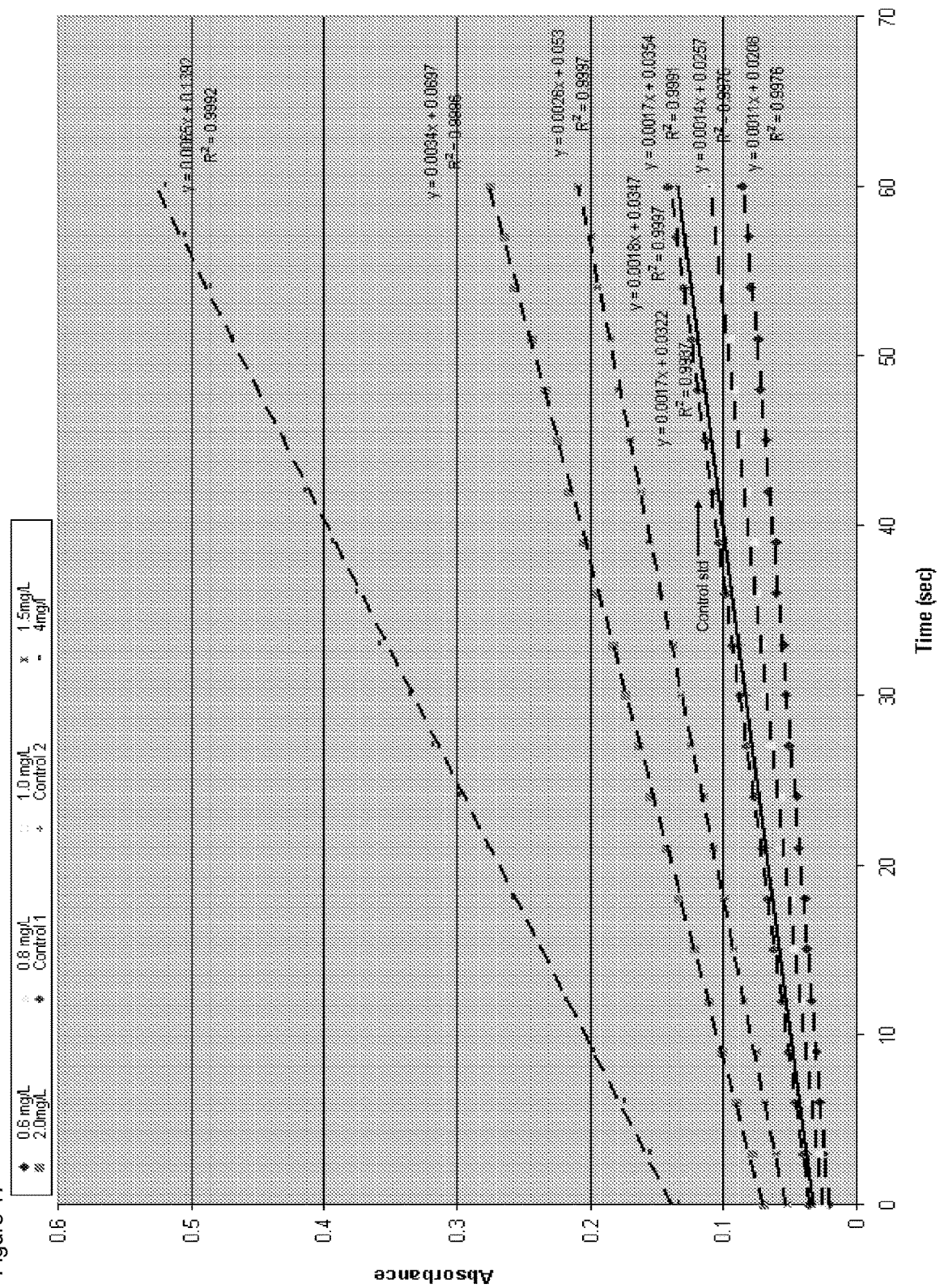
FIG. 17 shows a standard curve of Time (sec) vs. Absorbance for Control 1 and 2 (combined as control standard) as well as reference standard material dilutions of 0.6, 0.8, 1.0, 1.5, 2.0, and 4 mg/L.
Figure 18:
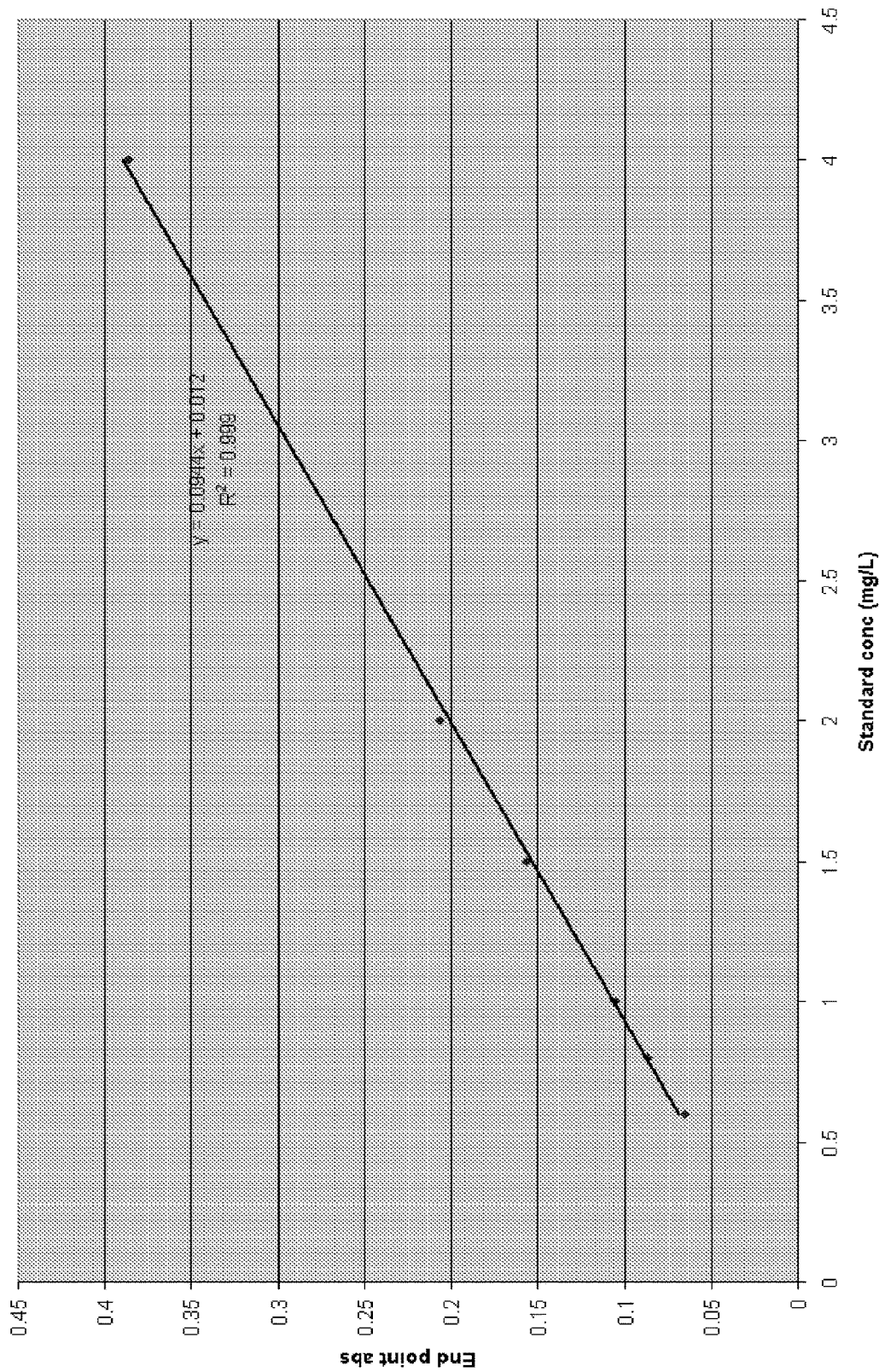
FIG. 18 shows a standard end point curve of Standard Concentration (mg/L) vs. End Point Absorbance. Standard absorbance was measured at time=60 sec minus standard absorbance at time=0 sec.
Figure 19:
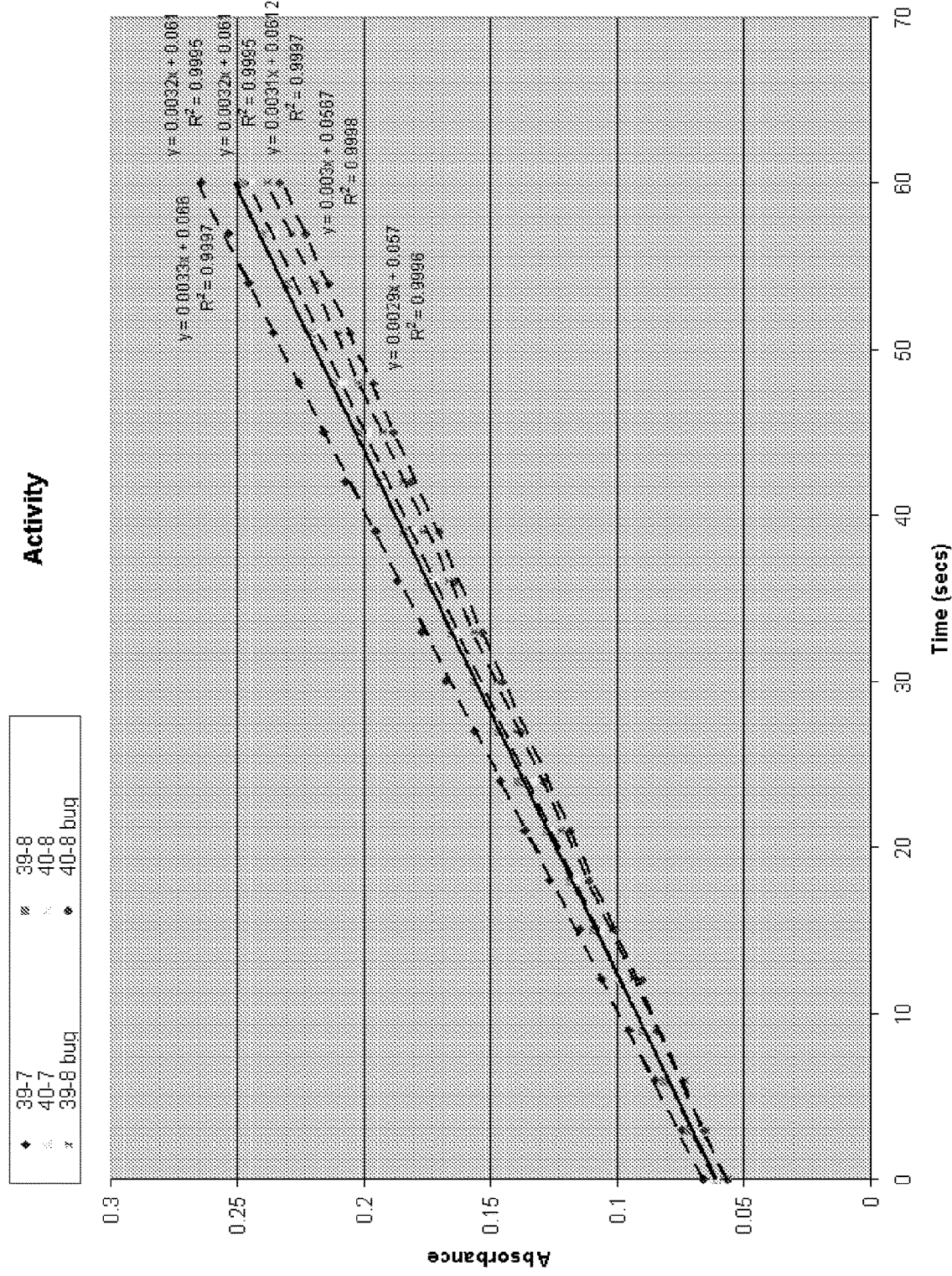
FIG. 19 shows a standard curve of Time (sec) vs. Absorbance for CLD977 (39) and CLD 990 (40) for both the second to last and last time point post induction (unlabeled=sonication) as well as the last time point post induction (Bug buster).

Assay plate 3 results are shown in FIGS. 17-19 and Table 4. Specifically, FIG. 17 shows a standard curve of Time (sec) vs. Absorbance for Control 1 and 2 (combined as control standard) as well as reference standard material dilutions of 0.6, 0.8, 1.0, 1.5, 2.0, and 4 mg/L. FIG. 18 shows a standard end point curve of Standard Concentration (mg/L) vs. End Point Absorbance. Standard absorbance was measured at time=60 sec minus standard absorbance at time=0 sec. FIG. 19 shows a standard curve of Time (sec) vs. Absorbance for CLD977 and CLD 990 (intracellular strains 39 and 40, respectively) for both the second to last and last time point post induction (unlabelled=sonication) as well as the last time point post induction (Bug buster). Table 4 shows a summary of assay plate 3 activity and titre results for CLD977 and CLD990 along with controls 1 and 2.

Tables 2-4 specifically show CLD981, CLD982, CLD977, and CLD990 end point OD, activity concentration (mg/L), assay dilution, concentration×dilution (g/L), whole cell weight (WCW (g/L)), periplasmic dilution factor, g/L P1A activity WB titre, estimated g/L P1A WB by SDS PAGE, SDS PAGE P, and SDS PAGE soluble (if applicable) compared to control 1 and 2.

TABLE 2

Results from the CENTA method for the periplasmic strains CLD981 (37) and CLD982 (38) at different time points compared to controls 1 and 2.

| Sample | End Point OD | Activity concentration (mg/L) | Assay dilution | Concentration × dilution (g/L) | WCW g/L | Periplasmic dilution factor | g/L P1A activity WB titre | Estimated g/L P1A WB by SDS PAGE |
|---|---|---|---|---|---|---|---|---|
| 37 12 hrs SN | 0.0090 | −0.0710 | 217 | 0.00 | 119.0 | | 0 | >0 |
| 37 24 hrs SN | 0.0155 | 0.0010 | 357 | 0.00 | 122.8 | | 0.00 | >0 |
| 37 48 hrs SN | 0.0570 | 0.4608 | 714 | 0.33 | 161.4 | | 0.28 | 0.05 |
| 37 OS1 24 h | 0.5195 | 5.5850 | 250 | 1.40 | | 0.862 | 1.62 | >0 |
| 37 OS2 24 h | 0.0420 | 0.2946 | 1250 | 0.37 | | 0.862 | 0.43 | 0.8 |
| 38 12 hrs SN | 0.0270 | 0.1285 | 357 | 0.05 | 123.9 | | 0.04 | >0 |
| 38 24 hrs SN | 0.1090 | 1.0369 | 2083 | 2.16 | 125.1 | | 1.89 | 0.35 |
| 38 48 hrs SN | 0.1150 | 1.1034 | 5155 | 5.69 | 122.1 | | 4.99 | 0.8 |
| 38 OS1 24 h | 0.1025 | 0.9649 | 4587 | 4.43 | | 1.06 | 4.18 | 0.8 |
| 38 OS2 24 h | 0.1440 | 1.4247 | 1613 | 2.30 | | 10.6 | 2.17 | 0.4 |
| Assay control 1 | 0.1210 | 1.1699 | 32000 | 37.44 | | | | |
| Assay control 2 | 0.1245 | 1.2087 | 32000 | 38.68 | | | | |

TABLE 3

Results from the CENTA method for the periplasmic strains CLD981 (37) and CLD982 (38) at different time points compared to controls 1 and 2.

| Sample | End Point OD | Activity concentration (mg/L) | Assay dilution | Concentration × dilution (g/L) | Periplasmic dilution factor | g/L P1A activity WB titre | SDS PAGE g/L WB |
|---|---|---|---|---|---|---|---|
| 37-14 OS1 | 0.0420 | 0.2946 | 417 | 0.12 | 0.71 | 0.17 | 0.05 |
| 37-14 OS2 | 0.0270 | 0.1285 | 1786 | 0.23 | 0.71 | 0.32 | 1.3 |
| 38-14 OS1 | 0.1090 | 1.0369 | 2294 | 2.38 | 1.44 | 1.65 | 0.4 |
| 38-14 OS2 | 0.1150 | 1.1034 | 1250 | 1.38 | 1.44 | 0.96 | 0.3 |
| Assay control 1 | 0.1140 | 0.9730 | 32000 | 31.14 | | | |
| Assay control 2 | 0.1145 | 0.9780 | 32000 | 31.30 | | | |

TABLE 4

Results from the CENTA method for the intracellular strains CLD977 (39) and CLD990 (40) at different time points compared to controls 1 and 2.

| Sample | End Point OD | Activity concentration (mg/L) | Assay dilution | Activity concentration × dilution (g/L) | g/L P1A activity WB titre | SDS PAGE P | SDS PAGE soluble |
|---|---|---|---|---|---|---|---|
| 39-7 (Sonication) | 0.1980 | 1.9705 | 20830 | 41.05 | 41.05 | 11.4 | 10.9 |
| 39-8 (Sonication) | 0.1875 | 1.8593 | 25000 | 46.48 | 46.48 | 14.0 | 12.1 |
| 40-7 (Sonication) | 0.1835 | 1.8169 | 25000 | 45.42 | 45.42 | 11.5 | 11.8 |
| 40-8 (Sonication) | 0.1865 | 1.8487 | 27780 | 51.36 | 51.36 | 13.2 | 13.7 |
| 39-8 (Bug buster) | 0.1820 | 1.8010 | 25000 | 45.03 | 45.03 | 14.0 | 12.1 |
| 40-8 (Bug buster) | 0.1770 | 1.7480 | 27780 | 48.56 | 48.56 | 13.2 | 13.7 |
| Assay control 1 | 0.1060 | 0.9957 | 32000 | 31.86 | | | |
| Assay control 2 | 0.1040 | 0.9745 | 32000 | 31.18 | | | |

As seen above, for the intracellular strains, there was a marginally greater activity in strain CLD990 compared to strain CLD977. For the periplasmic strains, the best secretion fraction for CLD981 (gene 1 leader) was OS2 fraction at 1.3 g/L (by SDS-PAGE), whereas the best secretion fraction for CLD982 (gene 7 leader) was SN fraction at 1.0 g/L (which included the non-processed form). Finally, for intracellular strains, it was observed that applying either Bug buster or sonication produced similar activity and SDS-PAGE results for these preparations.

Overall, intracellular activity and SDS PAGE results were more than 10× greater compared to secretion (periplasmic) fractions. This was a surprising result as typically, expressed proteins are collected from the periplasm. Additionally, the intracellular expression yielded β-lactamase in the soluble fraction as opposed to inclusion bodies.

Example 5: Large Scale P3A (SYN-004) Production cGMP manufacturing of P3A (SYN-004) was undertaken. The initial 750-liter cGMP production run used the pAVEway™ platform (FUJIFILM Diosynth Biotechnologies UK). Yields were 5.5 kilograms of >95% pure SYN-004 active pharmaceutical ingredient (API) drug substance. The GMP manufacturing process was initiated after a successful evaluation that produced high yielding cell lines that exhibited consistent biological activity of P3A (SYN-004). P3A (SYN-004) expression titers were improved by greater than about 15-fold (14 grams of P3A (SYN-004) per liter of *E. coli* culture broth), compared to the *Bacillus* platform previously employed for SYN-004's first-generation predecessor (roughly 1 gram of PIA per liter of *Bacillus subtilis* culture broth, see Example 1). A single chromatography column purification process reproducibly yielded 40-50% P3A (SYN-004) drug substance recovery at purity levels greater than 95%, another marked manufacturing improvement over the previous purification process.

Definitions

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g. inventive β-lactamases and/or pharmaceutical compositions (and/or additional agents) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from a GI tract disorder (e.g. ODD provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. In certain embodiments, the effect will result in a quantifiable change of two-fold, or three-fold, or four-fold, or five-fold, or ten-fold. Therapeutic benefit also includes halting or slowing the progression of the underlying disease or disorder or reduction in toxicity, regardless of whether improvement is realized.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for the production of a beta-lactamase polypeptide in *Escherichia coli* (*E. coli*), comprising:
    (a) providing a host *E. coli* cell transformed with an expression vector comprising a sequence encoding the beta-lactamase polypeptide;
    (b) culturing the *E. coli* cell to induce expression of the beta-lactamase polypeptide in the cytoplasm; and
    (c) recovering the beta-lactamase polypeptide from a cytoplasmic soluble fraction prepared from the *E. coli* cell; and
    wherein the method yields more than 10 grams of the beta-lactamase polypeptide per liter of culture,
    wherein the beta-lactamase polypeptide is not recovered or purified from a periplasmic fraction, a cell envelope fraction, a cytoplasmic insoluble fraction, an inclusion body, or an extracellular fraction of the *E. coli* cell.

2. The method of claim 1, wherein the method yields more than 15 grams of the beta-lactamase polypeptide per liter of culture.

3. The method of claim 1, wherein the *E. coli* cell is selected from BL21(DE3) or W3110.

4. The method of claim 1, wherein expression of the beta-lactamase polypeptide in the cytoplasm is induced by adding isopropylthiogalactoside (IPTG) to the culture.

5. The method of claim 1, wherein the beta-lactamase polypeptide comprises an amino acid sequence having at least 95% identity with SEQ ID NO: 1 (P1A).

6. The method of claim 1, wherein the beta-lactamase polypeptide comprises an amino acid sequence having at least 95% identity with SEQ ID NO: 10 (P2A).

7. The method of claim 1, wherein the beta-lactamase polypeptide comprises an amino acid sequence having at least 95% identity with SEQ ID NO: 5 (P3A).

8. The method of claim 1, wherein the beta-lactamase polypeptide comprises an amino acid sequence having at least 95% identity with SEQ ID NO: 7 (P4A).

9. The method of claim 7, wherein the beta-lactamase polypeptide comprises the amino acid sequence of SEQ ID NO: 5 (P3A).

10. The method of claim 6, wherein the beta-lactamase polypeptide comprises the amino acid sequence of SEQ ID NO: 10 (P2A).

11. The method of claim 1, wherein the expression vector comprises palindromic DNA looping.

12. The method of claim 1, wherein the expression vector is capable of tightly controlled gene expression.

13. The method of claim 1, wherein the production further comprises purifying said beta-lactamase with a single chromatography column step.

14. A method for the production of a beta-lactamase polypeptide in *Escherichia coli* (*E. coli*), comprising:
    (a) providing a host *E. coli* cell transformed with an expression vector comprising a sequence encoding the beta-lactamase polypeptide;
    (b) culturing the *E. coli* cell to induce expression of the beta-lactamase polypeptide in the cytoplasm; and
    (c) recovering the beta-lactamase polypeptide from a soluble fraction prepared from the *E. coli* cell;
wherein:
    the method yields more than 15 grams of the beta-lactamase polypeptide per liter of culture;
    wherein the beta-lactamase polypeptide is not recovered or purified from a periplasmic fraction, a cell envelope fraction, a cytoplasmic insoluble fraction, an inclusion body, or an extracellular fraction of the *E. coli* cell.

* * * * *

```
                        SEQUENCE LISTING

<160> NUMBER OF SEQ ID NOS: 12

<210> SEQ ID NO 1
<211> LENGTH: 263
<212> TYPE: PRT
<213> ORGANISM: Bacillus licheniformis

<400> SEQUENCE: 1

Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Tyr Thr Arg Asp Asp Leu Val Asn Tyr Asn Pro Ile Thr Glu
65                  70                  75                  80

Lys His Val Asp Thr Gly Met Thr Leu Lys Glu Leu Ala Asp Ala Ser
                85                  90                  95

Leu Arg Tyr Ser Asp Asn Ala Ala Gln Asn Leu Ile Leu Lys Gln Ile
            100                 105                 110
```

Gly Gly Pro Glu Ser Leu Lys Lys Glu Leu Arg Lys Ile Gly Asp Glu
            115                 120                 125

Val Thr Asn Pro Glu Arg Phe Glu Pro Glu Leu Asn Glu Val Asn Pro
        130                 135                 140

Gly Glu Thr Gln Asp Thr Ser Thr Ala Arg Ala Leu Val Thr Ser Leu
145                 150                 155                 160

Arg Ala Phe Ala Leu Glu Asp Lys Leu Pro Ser Glu Lys Arg Glu Leu
                165                 170                 175

Leu Ile Asp Trp Met Lys Arg Asn Thr Thr Gly Asp Ala Leu Ile Arg
            180                 185                 190

Ala Gly Val Pro Asp Gly Trp Glu Val Ala Asp Lys Thr Gly Ala Ala
        195                 200                 205

Ser Tyr Gly Thr Arg Asn Asp Ile Ala Ile Ile Trp Pro Pro Lys Gly
    210                 215                 220

Asp Pro Val Val Leu Ala Val Leu Ser Ser Arg Asp Lys Lys Asp Ala
225                 230                 235                 240

Lys Tyr Asp Asp Lys Leu Ile Ala Glu Ala Thr Lys Val Val Met Lys
                245                 250                 255

Ala Leu Asn Met Asn Gly Lys
            260

<210> SEQ ID NO 2
<211> LENGTH: 792
<212> TYPE: DNA
<213> ORGANISM: Bacillus licheniformis

<400> SEQUENCE: 2
gagatgaaag atgattttgc aaaacttgag gaacaatttg atgcaaaact cgggatcttt        60
gcattggata caggtacaaa ccggacggta gcgtatcggc cggatgagcg ttttgctttt       120
gcttcgacga ttaaggcttt aactgtaggc gtgcttttgc aacagaaatc aatagaagat       180
ctgaaccaga gaataacata tacacgtgat gatcttgtaa actacaaccc gattacggaa       240
aagcacgttg atacgggaat gacgctcaaa gagcttgcgg atgcttcgct tcgatatagt       300
gacaatgcgg cacagaatct cattcttaaa caaattggcg gacctgaaag tttgaaaaag       360
gaactgagga agattggtga tgaggttaca aatcccgaac gattcgaacc agagttaaat       420
gaagtgaatc cgggtgaaac tcaggatacc agtacagcaa gagcacttgt cacaagcctt       480
cgagcctttg ctcttgaaga taaacttcca agtgaaaaac gcgagctttt aatcgattgg       540
atgaaacgaa ataccactgg agacgcctta atccgtgccg gtgtgccgga cggttgggaa       600
gtggctgata aaactggagc ggcatcatat ggaacccgga atgacattgc catcatttgg       660
ccgccaaaag gagatcctgt cgttcttgca gtattatcca gcagggataa aaaggacgcc       720
aagtatgatg ataaacttat tgcagaggca acaaaggtgg taatgaaagc cttaaacatg       780
aacggcaaat aa                                                          792

<210> SEQ ID NO 3
<211> LENGTH: 299
<212> TYPE: PRT
<213> ORGANISM: Bacillus licheniformis

<400> SEQUENCE: 3

Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

```
Ala Ser Lys Thr Glu Met Lys Asp Asp Phe Ala Lys Leu Glu Glu Gln
         35                  40                  45

Phe Asp Ala Lys Leu Gly Ile Phe Ala Leu Asp Thr Gly Thr Asn Arg
 50                  55                  60

Thr Val Ala Tyr Arg Pro Asp Glu Arg Phe Ala Phe Ala Ser Thr Ile
 65                  70                  75                  80

Lys Ala Leu Thr Val Gly Val Leu Leu Gln Gln Lys Ser Ile Glu Asp
                 85                  90                  95

Leu Asn Gln Arg Ile Thr Tyr Thr Arg Asp Asp Leu Val Asn Tyr Asn
                100                 105                 110

Pro Ile Thr Glu Lys His Val Asp Thr Gly Met Thr Leu Lys Glu Leu
                115                 120                 125

Ala Asp Ala Ser Leu Arg Tyr Ser Asp Asn Ala Ala Gln Asn Leu Ile
130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
                165                 170                 175

Glu Val Asn Pro Gly Glu Thr Gln Asp Thr Ser Thr Ala Arg Ala Leu
                180                 185                 190

Val Thr Ser Leu Arg Ala Phe Ala Leu Glu Asp Lys Leu Pro Ser Glu
                195                 200                 205

Lys Arg Glu Leu Leu Ile Asp Trp Met Lys Arg Asn Thr Thr Gly Asp
210                 215                 220

Ala Leu Ile Arg Ala Gly Val Pro Asp Gly Trp Glu Val Ala Asp Lys
225                 230                 235                 240

Thr Gly Ala Ala Ser Tyr Gly Thr Arg Asn Asp Ile Ala Ile Ile Trp
                245                 250                 255

Pro Pro Lys Gly Asp Pro Val Val Leu Ala Val Leu Ser Ser Arg Asp
                260                 265                 270

Lys Lys Asp Ala Lys Tyr Asp Asp Lys Leu Ile Ala Glu Ala Thr Lys
                275                 280                 285

Val Val Met Lys Ala Leu Asn Met Asn Gly Lys
                290                 295

<210> SEQ ID NO 4
<211> LENGTH: 900
<212> TYPE: DNA
<213> ORGANISM: Bacillus licheniformis

<400> SEQUENCE: 4
atgattcaaa aacgaaagcg gacagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg gatctttgc attggataca      180 ggtacaaacc ggacggtagc gtatcggccg gatgagcgtt ttgctttgc ttcgacgatt      240 aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480
attggtgatg aggttacaaa tcccgaacga ttcgaaccag agttaaatga agtgaatccg     540
ggtgaaactc aggataccag tacagcaaga gcacttgtca caagccttcg agcctttgct     600
```
cttgaagata aacttccaag tgaaaaacgc gagcttttaa tcgattggat gaaacgaaat        660
accactggag acgccttaat ccgtgccggt gtgccggacg gttgggaagt ggctgataaa        720
actggagcgg catcatatgg aacccggaat gacattgcca tcatttggcc gccaaaagga        780
gatcctgtcg ttcttgcagt attatccagc agggataaaa aggacgccaa gtatgatgat        840
aaacttattg cagaggcaac aaaggtggta atgaaagcct taaacatgaa cggcaaataa        900

<210> SEQ ID NO 5
<211> LENGTH: 264
<212> TYPE: PRT
<213> ORGANISM: Bacillus licheniformis

<400> SEQUENCE: 5

Thr Glu Met Lys Asp Asp Phe Ala Lys Leu Glu Glu Gln Phe Asp Ala
1               5                   10                  15

Lys Leu Gly Ile Phe Ala Leu Asp Thr Gly Thr Asn Arg Thr Val Ala
            20                  25                  30

Tyr Arg Pro Asp Glu Arg Phe Ala Phe Ala Ser Thr Ile Lys Ala Leu
        35                  40                  45

Thr Val Gly Val Leu Leu Gln Gln Lys Ser Ile Glu Asp Leu Asn Gln
    50                  55                  60

Arg Ile Thr Tyr Thr Arg Asp Asp Leu Val Asn Tyr Asn Pro Ile Thr
65                  70                  75                  80

Glu Lys His Val Asp Thr Gly Met Thr Leu Lys Glu Leu Ala Asp Ala
                85                  90                  95

Ser Leu Arg Tyr Ser Asp Asn Ala Ala Gln Asn Leu Ile Leu Lys Gln
            100                 105                 110

Ile Gly Gly Pro Glu Ser Leu Lys Lys Glu Leu Arg Lys Ile Gly Asp
        115                 120                 125

Glu Val Thr Asn Pro Glu Arg Phe Glu Pro Glu Leu Asn Glu Val Asn
    130                 135                 140

Pro Gly Glu Thr Gln Asp Thr Ser Thr Ala Arg Ala Leu Val Thr Ser
145                 150                 155                 160

Leu Arg Ala Phe Ala Leu Glu Asp Lys Leu Pro Ser Glu Lys Arg Glu
                165                 170                 175

Leu Leu Ile Asp Trp Met Lys Arg Asn Thr Thr Gly Asp Ala Leu Ile
            180                 185                 190

Arg Ala Gly Val Pro Asp Gly Trp Glu Val Ala Asp Lys Thr Gly Ala
        195                 200                 205

Ala Ser Tyr Gly Thr Arg Asn Asp Ile Ala Ile Ile Trp Pro Pro Lys
    210                 215                 220

Gly Asp Pro Val Val Leu Ala Val Leu Ser Ser Arg Asp Lys Lys Asp
225                 230                 235                 240

Ala Lys Tyr Asp Asn Lys Leu Ile Ala Glu Ala Thr Lys Val Val Met
                245                 250                 255

Lys Ala Leu Asn Met Asn Gly Lys
            260

<210> SEQ ID NO 6
<211> LENGTH: 795
<212> TYPE: DNA
<213> ORGANISM: Bacillus licheniformis

<400> SEQUENCE: 6
atgactgaga tgaaagatga ttttgcgaag ctggaagaac agtttgacgc aaaattgggc        60

```
attttcgcgt tggacacggg tacgaatcgt acggttgcct accgtccgga cgagcgcttc      120
gccttcgcga gcacgatcaa agccctgacc gtcggcgtgc tgctccagca aaagagcatc      180
gaggacctga accagcgcat tacctacacc cgtgatgatc tggtgaacta taatccgatc      240
accgagaaac acgttgatac cggtatgacc ctgaaagaac tggcagatgc aagcctgcgc      300
tacagcgata cgcggctca gaatctgatt ctgaagcaaa tcggtggtcc ggagagcttg       360
aagaaagaac tgcgtaaaat cggcgatgaa gtcactaatc cggagcgttt tgagccggag      420
ctgaacgaag tgaatccggg tgaaacgcaa gacacgagca ccgcgcgtgc gcttgtcacc      480
tccctgcgcg ctttcgcact ggaagataag ctgccgtcgg agaaacgcga gctgctgatc      540
gactggatga agcgcaatac gaccggcgac gcgctgattc gtgcgggcgt tccggacggt      600
tgggaagtgg ctgacaagac cggtgcggcg agctacggca cccgtaacga tatcgcgatc      660
atttggccac ctaaaggtga cccggtcgtg ctggccgtac tgagcagccg tgacaagaaa      720
gacgcaaagt atgataacaa gctgattgca gaggcgacca agttgttat gaaggcactg       780 aacatgaatg gtaag                                                        795
```

<210> SEQ ID NO 7
<211> LENGTH: 262
<212> TYPE: PRT
<213> ORGANISM: Bacillus licheniformis

<400> SEQUENCE: 7

```
Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Thr Arg Asp Asp Leu Val Asn Tyr Asn Pro Ile Thr Glu Lys
65                  70                  75                  80

His Val Asp Thr Gly Met Thr Leu Lys Glu Leu Ala Asp Ala Ser Leu
                85                  90                  95

Arg Tyr Ser Asp Asn Ala Ala Gln Asn Leu Ile Leu Lys Gln Ile Gly
            100                 105                 110

Gly Pro Glu Ser Leu Lys Lys Glu Leu Arg Lys Ile Gly Asp Glu Val
        115                 120                 125

Thr Asn Pro Glu Arg Phe Glu Pro Glu Leu Asn Glu Val Asn Pro Gly
    130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Val Pro Asp Gly Trp Glu Val Gly Asp Lys Thr Gly Ser Gly Asp
        195                 200                 205

Tyr Gly Thr Arg Asn Asp Ile Ala Ile Ile Trp Pro Pro Lys Gly Asp
    210                 215                 220

Pro Val Val Leu Ala Val Leu Ser Ser Arg Asp Lys Lys Asp Ala Lys
225                 230                 235                 240
```

Tyr Asp Asn Lys Leu Ile Ala Glu Ala Thr Lys Val Val Met Lys Ala
                245                 250                 255

Leu Asn Met Asn Gly Lys
            260

<210> SEQ ID NO 8
<211> LENGTH: 299
<212> TYPE: PRT
<213> ORGANISM: Bacillus licheniformis

<400> SEQUENCE: 8

Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

Ala Ser Lys Thr Glu Met Lys Asp Asp Phe Ala Lys Leu Glu Glu Gln
        35                  40                  45

Phe Asp Ala Lys Leu Gly Ile Phe Ala Leu Asp Thr Gly Thr Asn Arg
    50                  55                  60

Thr Val Ala Tyr Arg Pro Asp Glu Arg Phe Ala Phe Ala Ser Thr Ile
65                  70                  75                  80

Lys Ala Leu Thr Val Gly Val Leu Leu Gln Gln Lys Ser Ile Glu Asp
                85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
        115                 120                 125

Ala Asp Ala Ser Leu Arg Tyr Ser Asp Asn Ala Ala Gln Asn Leu Ile
    130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
                165                 170                 175

Glu Val Asn Pro Gly Glu Thr Gln Asp Thr Ser Thr Ala Arg Ala Leu
            180                 185                 190

Val Thr Ser Leu Arg Ala Phe Ala Leu Glu Asp Lys Leu Pro Ser Glu
        195                 200                 205

Lys Arg Glu Leu Leu Ile Asp Trp Met Lys Arg Asn Thr Thr Gly Asp
    210                 215                 220

Ala Leu Ile Arg Ala Gly Val Pro Asp Gly Trp Glu Val Gly Asp Lys
225                 230                 235                 240

Thr Gly Ser Gly Asp Tyr Gly Thr Arg Asn Asp Ile Ala Ile Ile Trp
                245                 250                 255

Pro Pro Lys Gly Asp Pro Val Val Leu Ala Val Leu Ser Ser Arg Asp
            260                 265                 270

Lys Lys Asp Ala Lys Tyr Asp Asn Lys Leu Ile Ala Glu Ala Thr Lys
        275                 280                 285

Val Val Met Lys Ala Leu Asn Met Asn Gly Lys
    290                 295

<210> SEQ ID NO 9
<211> LENGTH: 900
<212> TYPE: DNA
<213> ORGANISM: Bacillus licheniformis

<400> SEQUENCE: 9

-continued

```
atgattcaaa aacgaaagcg gacagtttcg ttcagacttg tgcttatgtg cacgctgtta    60
tttgtcagtt tgccgattac aaaaacatca gcgcaagctt ccaagacgga gatgaaagat   120
gattttgcaa aacttgagga acaatttgat gcaaaactcg ggatctttgc attggataca   180
ggtacaaacc ggacggtagc gtatcggccg gatgagcgtt ttgctttttgc ttcgacgatt   240
aaggctttaa ctgtaggcgt gcttttgcaa cagaaatcaa tagaagatct gaaccagaga   300
ataacatata cacgtgatga tcttgtaaac tacaacccga ttacggaaaa gcacgttgat   360
acgggaatga cgctcaaaga gcttgcggat gcttcgcttc gatatagtga caatgcggca   420
cagaatctca ttcttaaaca aattggcgga cctgaaagtt tgaaaaagga actgaggaag   480
attggtgatg aggttacaaa tcccgaacga ttcgaaccag agttaaatga agtgaatccg   540
ggtgaaactc aggataccag tacagcaaga gcacttgtca caagccttcg agcctttgct   600
cttgaagata aacttccaag tgaaaaacgc gagcttttaa tcgattggat gaaacgaaat   660
accactggag acgccttaat ccgtgccggt gtgccggacg ttgggaagt gggtgataaa   720
actggaagcg gagattatgg aacccggaat gacattgcca tcatttggcc gccaaaagga   780
gatcctgtcg ttcttgcagt attatccagc agggataaaa aggacgccaa gtatgataat   840
aaacttattg cagaggcaac aaaggtggta atgaaagcct taaacatgaa cggcaaataa   900
```

<210> SEQ ID NO 10
<211> LENGTH: 216
<212> TYPE: PRT
<213> ORGANISM: Bacillus licheniformis

<400> SEQUENCE: 10

```
Glu Thr Gly Thr Ile Ser Ile Ser Gln Leu Asn Lys Asn Val Trp Val
1               5                   10                  15

His Thr Glu Leu Gly Tyr Phe Asn Gly Glu Ala Val Pro Ser Asn Gly
            20                  25                  30

Leu Val Leu Asn Thr Ser Lys Gly Leu Val Leu Val Asp Ser Ser Trp
        35                  40                  45

Asp Asn Lys Leu Thr Lys Glu Leu Ile Glu Met Val Glu Lys Lys Phe
    50                  55                  60

Gln Lys Arg Val Thr Asp Val Ile Ile Thr His Ala His Ala Asp Arg
65                  70                  75                  80

Ile Gly Gly Ile Thr Ala Leu Lys Glu Arg Gly Ile Lys Ala His Ser
                85                  90                  95

Thr Ala Leu Thr Ala Glu Leu Ala Lys Asn Ser Gly Tyr Glu Glu Pro
            100                 105                 110

Leu Gly Asp Leu Gln Thr Ile Thr Ser Leu Lys Phe Gly Asn Thr Lys
        115                 120                 125

Val Glu Thr Phe Tyr Pro Gly Lys Gly His Thr Glu Asp Asn Ile Val
    130                 135                 140

Val Trp Leu Pro Gln Tyr Gln Ile Leu Ala Gly Gly Cys Leu Val Lys
145                 150                 155                 160

Ser Ala Glu Ala Lys Asp Leu Gly Asn Val Ala Asp Ala Tyr Val Asn
                165                 170                 175

Glu Trp Ser Thr Ser Ile Glu Asn Val Leu Lys Arg Tyr Gly Asn Ile
            180                 185                 190

Asn Ser Val Val Pro Gly His Gly Glu Val Gly Asp Lys Gly Leu Leu
        195                 200                 205

Leu His Thr Leu Asp Leu Leu Lys
```

```
                  210               215

<210> SEQ ID NO 11
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 11

Gln Ala Ser Lys Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide.

<400> SEQUENCE: 12

Gln Ala Lys Ser Thr
1               5
```